US012731685B2

(12) United States Patent
Mason et al.

(10) Patent No.: US 12,731,685 B2
(45) **Date of Patent: *Sep. 8, 2026**

(54) SYSTEM AND METHOD TO ENABLE REMOTE ADJUSTMENT OF A DEVICE DURING A TELEMEDICINE SESSION

(71) Applicant: ROM TECHNOLOGIES, INC., Brookfield, CT (US)

(72) Inventors: Steven Mason, Brookfield, CT (US); Daniel Posnack, Brookfield, CT (US); Peter Arn, Brookfield, CT (US); Wendy Para, Brookfield, CT (US); S. Adam Hacking, Brookfield, CT (US); Micheal Mueller, Brookfield, CT (US); Joseph Guaneri, Brookfield, CT (US); Jonathan Greene, Brookfield, CT (US)

(73) Assignee: ROM Technologies, Inc., Brookfield, CT (US)

( * ) Notice: Subject to any disclaimer, the term of this patent is extended or adjusted under 35 U.S.C. 154(b) by 933 days.

This patent is subject to a terminal disclaimer.

(21) Appl. No.: 17/147,514

(22) Filed: Jan. 13, 2021

(65) Prior Publication Data

US 2021/0134458 A1 May 6, 2021

Related U.S. Application Data

(63) Continuation-in-part of application No. 17/021,895, filed on Sep. 15, 2020, now Pat. No. 11,071,597.

(Continued)

(51) Int. Cl.
*G16H 40/67* (2018.01)
*G16H 20/30* (2018.01)
(Continued)

(52) U.S. Cl.
CPC ............ *G16H 40/67* (2018.01); *G16H 20/30* (2018.01); *G16H 80/00* (2018.01); *H04L 67/025* (2013.01)

(58) Field of Classification Search
CPC ........ G16H 40/67; G16H 20/30; G16H 40/63; G16H 50/20; G16H 40/60; G16H 10/60;
(Continued)

(56) References Cited

U.S. PATENT DOCUMENTS

| | | | |
|---|---|---|---|
| 59,915 | A | 11/1866 | Lallement |
| 363,522 | A | 5/1887 | Knous |

(Continued)

FOREIGN PATENT DOCUMENTS

| | | |
|---|---|---|
| CA | 2698078 A1 | 3/2010 |
| CA | 3193419 A1 | 3/2022 |

(Continued)

OTHER PUBLICATIONS

Malloy, Online Article "AI-enabled EKGs find difference between numerical age and biological age significantly affects health, longevity", Website: https://newsnetwork.mayoclinic.org/discussion/ai-enabled-ekgs-find-difference-between-numerical-age-and-biological-age-significantly-affects-health-longevity/, Mayo Clinic News Network, May 20, 2021, retrieved: Jan. 23, 2023, p. 1-4.

(Continued)

*Primary Examiner* — Darrin D Dunn
(74) *Attorney, Agent, or Firm* — Dickinson Wright PLLC; Jonathan H. Harder; Stephen A. Mason

(57) ABSTRACT

A computer-implemented system comprising a treatment device, a patient interface, and a processing device is disclosed. The treatment device is configured to be manipulated by a user while the user performs a treatment plan. The patient interface comprises an output device configured to present telemedicine information associated with a tele- (Continued)

medicine session. The processing device is configured to receive a treatment plan for a patient; during the telemedicine session, use the treatment plan to generate at least one parameter; and responsive to at least one trigger condition occurring, control at least one operation of the device.

24 Claims, 13 Drawing Sheets

Related U.S. Application Data

(60) Provisional application No. 63/029,896, filed on May 26, 2020, provisional application No. 62/910,232, filed on Oct. 3, 2019.

(51) Int. Cl.
*G16H 80/00* (2018.01)
*H04L 67/025* (2022.01)

(58) Field of Classification Search
CPC ..... A61B 5/74; A61B 5/7475; A61B 2505/09; A61B 5/0022; A61B 5/4528; A61B 5/486; A61B 5/024; A61B 5/4851; A61B 5/6831; A61B 5/4836; A61B 5/7465; A61B 5/7435; A61M 2205/3553; A61M 2205/3592; G05B 2219/25428; G05B 15/02; G05B 19/0426; G05B 19/4183; G05B 19/4185; G05B 2219/23298; G05B 2219/23299; G05B 2219/24058; G05B 2219/31104; G05B 2219/31121
See application file for complete search history.

(56) References Cited

U.S. PATENT DOCUMENTS 446,671 A 2/1891 Elliott
610,157 A 8/1898 Campbell
631,276 A 8/1899 Bulova
823,712 A 6/1906 Uhlmann
1,149,029 A 8/1915 Clark
1,227,743 A 5/1917 Burgedorfp
1,784,230 A 12/1930 Freeman
3,081,645 A 3/1963 Bergfors
3,100,640 A 8/1963 Weitzel
3,137,014 A 6/1964 Meucci
3,143,316 A 8/1964 Shapiro
3,713,438 A 1/1973 Knutsen
3,744,480 A 7/1973 Gause et al.
3,888,136 A 6/1975 Lapeyre
4,079,957 A 3/1978 Blease
4,408,613 A 10/1983 Relyea
4,436,097 A 3/1984 Cunningham
4,446,753 A 5/1984 Nagano
4,477,072 A 10/1984 DeCloux
4,499,900 A 2/1985 Petrofsky et al.
4,509,742 A 4/1985 Cones
4,606,241 A 8/1986 Fredriksson
4,611,807 A 9/1986 Castillo
4,616,823 A 10/1986 Yang
4,648,287 A 3/1987 Preskitt
4,673,178 A 6/1987 Dwight
4,822,032 A 4/1989 Whitmore et al.
4,824,104 A 4/1989 Bloch
4,850,245 A 7/1989 Feamster et al.
4,858,942 A 8/1989 Rodriguez
4,860,763 A 8/1989 Schminke
4,869,497 A 9/1989 Stewart et al.
4,915,374 A 4/1990 Watkins
4,930,768 A 6/1990 Lapcevic
4,932,650 A 6/1990 Bingham et al.
4,961,570 A 10/1990 Chang
5,137,501 A 8/1992 Mertesdorf
5,161,430 A 11/1992 Febey
5,202,794 A 4/1993 Schnee et al.
5,240,417 A 8/1993 Smithson et al.
5,247,853 A 9/1993 Dalebout
5,256,117 A 10/1993 Potts et al.
5,282,748 A 2/1994 Little
5,284,131 A 2/1994 Gray
5,316,532 A 5/1994 Butler
5,318,487 A 6/1994 Golen
5,324,241 A 6/1994 Artigues et al.
5,336,147 A 8/1994 Sweeney, III
5,338,272 A 8/1994 Sweeney, III
5,356,356 A 10/1994 Hildebrandt
5,361,649 A 11/1994 Slocum, Jr.
D359,777 S 6/1995 Hildebrandt
5,429,140 A 7/1995 Burdea et al.
5,458,022 A 10/1995 Mattfeld et al.
5,487,713 A 1/1996 Butler
5,566,589 A 10/1996 Buck
5,580,338 A 12/1996 Scelta et al.
5,676,349 A 10/1997 Wilson
5,685,804 A 11/1997 Whan-Tong et al.
5,738,636 A 4/1998 Saringer et al.
5,860,941 A 1/1999 Saringer et al.
5,950,813 A 9/1999 Hoskins et al.
6,007,459 A 12/1999 Burgess
D421,075 S 2/2000 Hildebrandt
6,053,847 A 4/2000 Stearns et al.
6,077,201 A 6/2000 Cheng
6,102,834 A 8/2000 Chen
6,110,130 A 8/2000 Kramer
6,155,958 A 12/2000 Goldberg
6,162,189 A 12/2000 Girone et al.
6,182,029 B1 1/2001 Friedman
6,253,638 B1 7/2001 Bermudez
6,267,735 B1 7/2001 Blanchard et al.
6,273,863 B1 8/2001 Avni et al.
6,371,891 B1 4/2002 Speas
6,413,190 B1 7/2002 Wood et al.
6,430,436 B1 8/2002 Richter
6,436,058 B1 8/2002 Krahner et al.
6,450,923 B1 9/2002 Vatti
6,474,193 B1 11/2002 Farney
6,491,649 B1 12/2002 Ombrellaro
6,514,085 B2 2/2003 Slattery et al.
6,535,861 B1 3/2003 OConnor et al.
6,543,309 B2 4/2003 Heim
6,589,139 B1 7/2003 Butterworth
6,601,016 B1 7/2003 Brown et al.
6,602,191 B2 8/2003 Quy
6,613,000 B1 9/2003 Reinkensmeyer et al.
6,626,800 B1 9/2003 Casler
6,626,805 B1 9/2003 Lightbody
6,640,122 B2 10/2003 Manoli
6,640,662 B1 11/2003 Baxter
6,652,425 B1 11/2003 Martin et al.
6,659,946 B1 12/2003 Batchelor et al.
6,820,517 B1 11/2004 Farney
6,865,969 B2 3/2005 Stevens
6,890,312 B1 5/2005 Priester et al.
6,895,834 B1 5/2005 Baatz
6,902,513 B1 6/2005 McClure
7,058,453 B2 6/2006 Nelson et al.
7,063,643 B2 6/2006 Arai
7,156,665 B1 1/2007 OConnor et al.
7,156,780 B1 1/2007 Fuchs et al.
7,169,085 B1 1/2007 Killin et al.
7,204,788 B2 4/2007 Andrews
7,209,886 B2 4/2007 Kimmel
7,226,394 B2 6/2007 Johnson
RE39,904 E 10/2007 Lee
7,507,188 B2 3/2009 Nurre
7,594,879 B2 9/2009 Johnson
7,628,730 B1 12/2009 Watterson et al.
D610,635 S 2/2010 Hildebrandt
7,778,851 B2 8/2010 Schoenberg et al.
7,809,601 B2 10/2010 Shaya et al.
7,815,551 B2 10/2010 Merli
7,833,135 B2 11/2010 Radow et al.

(56) References Cited

U.S. PATENT DOCUMENTS 7,837,472 B1 11/2010 Elsmore et al.
7,890,342 B1 2/2011 Yruko
7,955,219 B2 6/2011 Birrell et al.
7,969,315 B1 6/2011 Ross et al.
7,974,689 B2 7/2011 Volpe et al.
7,988,599 B2 8/2011 Ainsworth et al.
8,012,107 B2 9/2011 Einav et al.
8,021,270 B2 9/2011 D'Eredita
8,038,578 B2 10/2011 Olrik et al.
8,079,937 B2 12/2011 Bedell et al.
8,113,991 B2 2/2012 Kutliroff
8,172,724 B2 5/2012 Solomon
8,177,732 B2 5/2012 Einav et al.
8,287,434 B2 10/2012 Zavadsky et al.
8,298,123 B2 10/2012 Hickman
8,371,990 B2 2/2013 Shea
8,419,593 B2 4/2013 Ainsworth et al.
8,465,398 B2 6/2013 Lee et al.
8,503,086 B2 8/2013 French
8,506,458 B2 8/2013 Dugan
8,515,777 B1 8/2013 Rajasenan
8,540,515 B2 9/2013 Williams et al.
8,540,516 B2 9/2013 Williams et al.
8,556,778 B1 10/2013 Dugan
8,607,465 B1 12/2013 Edwards
8,613,689 B2 12/2013 Dyer et al.
8,615,529 B2 12/2013 Reiner
8,672,812 B2 3/2014 Dugan
8,751,264 B2 6/2014 Beraja et al.
8,784,273 B2 7/2014 Dugan
8,818,496 B2 8/2014 Dziubinski et al.
8,823,448 B1 9/2014 Shen
8,845,493 B2 9/2014 Watterson et al.
8,849,681 B2 9/2014 Hargrove et al.
8,864,628 B2 10/2014 Boyette et al.
8,893,287 B2 11/2014 Gjonej et al.
8,911,327 B1 12/2014 Boyette
8,979,711 B2 3/2015 Dugan
9,004,598 B2 4/2015 Weber
9,167,281 B2 10/2015 Petrov et al.
9,248,071 B1 2/2016 Benda et al.
9,256,711 B2 2/2016 Horseman
9,272,091 B2 3/2016 Skelton
9,272,185 B2 3/2016 Dugan
9,283,434 B1 3/2016 Wu
9,295,878 B2 3/2016 Corbalis et al.
9,311,789 B1 4/2016 Gwin
9,367,668 B2 6/2016 Flynt et al.
9,409,054 B2 8/2016 Dugan
9,443,205 B2 9/2016 Wall
9,474,935 B2 10/2016 Abbondanza et al.
9,480,873 B2 11/2016 Chuang
9,481,428 B2 11/2016 Gros et al.
9,514,277 B2 12/2016 Hassing et al.
9,566,472 B2 2/2017 Dugan
9,579,056 B2 2/2017 Rosenbek et al.
9,629,558 B2 4/2017 Yuen et al.
9,640,057 B1 5/2017 Ross
9,707,147 B2 7/2017 Levital et al.
D794,142 S 8/2017 Zhou
9,717,947 B2 8/2017 Lin
9,737,761 B1 8/2017 Govindarajan
9,757,612 B2 9/2017 Weber
9,773,330 B1 9/2017 Douglas
9,782,621 B2 10/2017 Chiang et al.
9,802,076 B2 10/2017 Murray et al.
9,802,081 B2 10/2017 Ridgel et al.
9,813,239 B2 11/2017 Chee et al.
9,827,445 B2 11/2017 Marcos et al.
9,849,337 B2 12/2017 Roman et al.
9,868,028 B2 1/2018 Shin
9,872,087 B2 1/2018 DelloStritto et al.
9,872,637 B2 1/2018 Kording et al.
9,914,053 B2 3/2018 Dugan
9,919,198 B2 3/2018 Romeo et al.
9,937,382 B2 4/2018 Dugan
9,939,784 B1 4/2018 Berardinelli
9,974,478 B1 5/2018 Brokaw
9,977,587 B2 5/2018 Mountain
9,993,181 B2 6/2018 Ross
9,997,082 B2 6/2018 Kaleal
10,004,946 B2 6/2018 Ross
10,026,052 B2 7/2018 Brown et al.
D826,349 S 8/2018 Oblamski
10,055,550 B2 8/2018 Goetz
10,058,473 B2 8/2018 Oshima et al.
10,074,148 B2 9/2018 Cashman et al.
10,089,443 B2 10/2018 Miller et al.
10,111,643 B2 10/2018 Shulhauser et al.
10,130,298 B2 11/2018 Mokaya et al.
10,130,311 B1 11/2018 De Sapio et al.
10,137,328 B2 11/2018 Baudhuin
10,143,395 B2 12/2018 Chakravarthy et al.
10,155,134 B2 12/2018 Dugan
10,159,872 B2 12/2018 Sasaki et al.
10,173,094 B2 1/2019 Gomberg et al.
10,173,095 B2 1/2019 Gomberg et al.
10,173,096 B2 1/2019 Gomberg et al.
10,173,097 B2 1/2019 Gomberg et al.
10,198,928 B1 2/2019 Ross et al.
10,226,663 B2 3/2019 Gomberg et al.
10,231,664 B2 3/2019 Ganesh
10,244,990 B2 4/2019 Hu et al.
10,258,823 B2 4/2019 Cole
10,322,315 B2 6/2019 Foley et al.
10,325,070 B2 6/2019 Beale et al.
10,327,697 B1 6/2019 Stein et al.
10,362,940 B2 7/2019 Tran
10,369,021 B2 8/2019 Zoss et al.
10,380,866 B1 8/2019 Ross et al.
10,413,222 B1 9/2019 Kayyali
10,413,238 B1 9/2019 Cooper
10,424,033 B2 9/2019 Romeo
10,430,552 B2 10/2019 Mihai
D866,957 S 11/2019 Ross et al.
10,468,131 B2 11/2019 Macoviak et al.
10,475,323 B1 11/2019 Ross
10,475,537 B2 11/2019 Purdie et al.
10,492,977 B2 12/2019 Kapure et al.
10,507,358 B2 12/2019 Kinnunen et al.
10,542,914 B2 1/2020 Forth et al.
10,546,467 B1 1/2020 Luciano, Jr. et al.
10,569,122 B2 2/2020 Johnson
10,572,626 B2 2/2020 Balram
10,576,331 B2 3/2020 Kuo
10,581,896 B2 3/2020 Nachenberg
10,625,114 B2 4/2020 Ercanbrack
10,646,746 B1 5/2020 Gomberg et al.
10,660,534 B2 5/2020 Lee et al.
10,678,890 B2 6/2020 Bitran et al.
10,685,092 B2 6/2020 Paparella et al.
10,741,285 B2 8/2020 Moturu
10,777,200 B2 9/2020 Will et al.
D899,605 S 10/2020 Ross et al.
10,792,495 B2 10/2020 Izvorski et al.
10,814,170 B2 10/2020 Wang et al.
10,857,426 B1 12/2020 Neumann
10,867,695 B2 12/2020 Neagle
10,874,905 B2 12/2020 Belson et al.
D907,143 S 1/2021 Ach et al.
10,881,911 B2 1/2021 Kwon et al.
10,918,332 B2 2/2021 Belson et al.
10,931,643 B1 2/2021 Neumann
10,987,176 B2 4/2021 Poltaretskyi et al.
10,991,463 B2 4/2021 Kutzko et al.
11,000,735 B2 5/2021 Orady et al.
11,045,709 B2 6/2021 Putnam
11,065,170 B2 7/2021 Yang et al.
11,065,527 B2 7/2021 Putnam
11,069,436 B2 7/2021 Mason et al.
11,071,597 B2 7/2021 Posnack et al.
11,075,000 B2 7/2021 Mason et al.
D928,635 S 8/2021 Hacking et al.
11,087,865 B2 8/2021 Mason et al.

(56) References Cited

U.S. PATENT DOCUMENTS 11,094,400 B2 8/2021 Riley et al.
11,101,028 B2 8/2021 Mason et al.
11,107,591 B1 8/2021 Mason
11,139,060 B2 10/2021 Mason et al.
11,185,735 B2 11/2021 Arn et al.
11,185,738 B1 11/2021 McKirdy et al.
D939,096 S 12/2021 Lee
D939,644 S 12/2021 Ach et al.
D940,797 S 1/2022 Ach et al.
D940,891 S 1/2022 Lee
11,229,727 B2 1/2022 Tatonetti
11,229,788 B1 1/2022 John
11,265,234 B2 3/2022 Guaneri et al.
11,270,795 B2 3/2022 Mason et al.
11,272,879 B2 3/2022 Wiedenhoefer et al.
11,278,766 B2 3/2022 Lee
11,282,599 B2 3/2022 Mason et al.
11,282,604 B2 3/2022 Mason et al.
11,282,608 B2 3/2022 Mason et al.
11,284,797 B2 3/2022 Mason et al.
D948,639 S 4/2022 Ach et al.
11,295,848 B2 4/2022 Mason et al.
11,298,284 B2 4/2022 Bayerlein
11,309,085 B2 4/2022 Mason et al.
11,317,975 B2 5/2022 Mason et al.
11,325,005 B2 5/2022 Mason et al.
11,328,807 B2 5/2022 Mason et al.
11,337,648 B2 5/2022 Mason
11,347,829 B1 5/2022 Sclar et al.
11,348,683 B2 5/2022 Guaneri et al.
11,370,328 B2 6/2022 Main
11,376,470 B2 7/2022 Weldemariam
11,404,150 B2 8/2022 Guaneri et al.
11,410,768 B2 8/2022 Mason et al.
11,422,841 B2 8/2022 Jeong
11,437,137 B1 9/2022 Harris
11,495,355 B2 11/2022 McNutt et al.
11,508,258 B2 11/2022 Nakashima et al.
11,508,482 B2 11/2022 Mason et al.
11,515,021 B2 11/2022 Mason
11,515,028 B2 11/2022 Mason
11,524,210 B2 12/2022 Kim et al.
11,527,326 B2 12/2022 McNair et al.
11,532,402 B2 12/2022 Farley et al.
11,534,654 B2 12/2022 Silcock et al.
D976,339 S 1/2023 Li
11,541,274 B2 1/2023 Hacking
11,553,969 B1 1/2023 Lang et al.
11,621,067 B1 4/2023 Nolan
11,636,944 B2 4/2023 Hanrahan et al.
11,654,327 B2 5/2023 Phillips et al.
11,663,673 B2 5/2023 Pyles
11,673,024 B2 6/2023 Omid-Zohoor
11,701,548 B2 7/2023 Posnack et al.
11,776,676 B2 10/2023 Savolainen
11,944,579 B2 4/2024 Sankai
11,957,960 B2 4/2024 Bissonnette et al.
12,004,871 B1 6/2024 Fazeli
12,057,210 B2 8/2024 Akinola et al.
12,205,704 B2 1/2025 Hosoi et al.
2001/0044573 A1 11/2001 Manoli
2002/0010596 A1 1/2002 Matory
2002/0072452 A1 6/2002 Torkelson
2002/0143279 A1 10/2002 Porter et al.
2002/0160883 A1 10/2002 Dugan
2002/0183599 A1 12/2002 Castellanos
2003/0013072 A1 1/2003 Thomas
2003/0036683 A1 2/2003 Kehr et al.
2003/0064860 A1 4/2003 Yamashita et al.
2003/0064863 A1 4/2003 Chen
2003/0083596 A1 5/2003 Kramer et al.
2003/0092536 A1 5/2003 Romanelli et al.
2003/0109814 A1 6/2003 Rummerfield
2003/0181832 A1 9/2003 Carnahan et al.
2004/0072652 A1 4/2004 Alessandri et al.
2004/0102931 A1 5/2004 Ellis et al.
2004/0106502 A1 6/2004 Sher
2004/0147969 A1 7/2004 Mann et al.
2004/0172093 A1 9/2004 Rummerfield
2004/0194572 A1 10/2004 Kim
2004/0197727 A1 10/2004 Sachdeva et al.
2004/0204959 A1 10/2004 Moreano et al.
2005/0020411 A1 1/2005 Andrews
2005/0043153 A1 2/2005 Krietzman
2005/0049122 A1 3/2005 Vallone et al.
2005/0085346 A1 4/2005 Johnson
2005/0085353 A1 4/2005 Johnson
2005/0115561 A1 6/2005 Stahmann
2005/0143641 A1 6/2005 Tashiro
2005/0274220 A1 12/2005 Reboullet
2006/0003871 A1 1/2006 Houghton
2006/0046905 A1 3/2006 Doody, Jr. et al.
2006/0058648 A1 3/2006 Meier
2006/0064136 A1 3/2006 Wang
2006/0064329 A1 3/2006 Abolfathi et al.
2006/0129432 A1 6/2006 Choi et al.
2006/0199700 A1 9/2006 LaStayo et al.
2006/0247095 A1 11/2006 Rummerfield
2006/0277074 A1 12/2006 Einav
2007/0042868 A1 2/2007 Fisher et al.
2007/0118389 A1 5/2007 Shipon
2007/0118406 A1 5/2007 Killin et al.
2007/0137307 A1 6/2007 Gruben et al.
2007/0173392 A1 7/2007 Stanford
2007/0184414 A1 8/2007 Perez
2007/0194939 A1 8/2007 Alvarez et al.
2007/0219059 A1 9/2007 Schwartz
2007/0271065 A1 11/2007 Gupta et al.
2007/0287597 A1 12/2007 Cameron
2008/0021834 A1 1/2008 Holla et al.
2008/0077619 A1 3/2008 Gilley et al.
2008/0082356 A1 4/2008 Friedlander et al.
2008/0096726 A1 4/2008 Riley et al.
2008/0103023 A1 5/2008 Chung
2008/0153592 A1 6/2008 James-Herbert
2008/0161166 A1 7/2008 Lo
2008/0161733 A1 7/2008 Einav et al.
2008/0183500 A1 7/2008 Banigan
2008/0281633 A1 11/2008 Burdea et al.
2008/0300914 A1 12/2008 Karkanias et al.
2008/0312040 A1 12/2008 Ochi
2009/0011907 A1 1/2009 Radow et al.
2009/0037334 A1 2/2009 Hsu
2009/0058635 A1 3/2009 LaLonde et al.
2009/0070138 A1 3/2009 Langheier et al.
2009/0157617 A1 6/2009 Herlocker
2009/0211395 A1 8/2009 Mul'e
2009/0270227 A1 10/2009 Ashby et al.
2009/0287503 A1 11/2009 Angell et al.
2009/0299766 A1 12/2009 Friedlander et al.
2010/0048358 A1 2/2010 Tchao et al.
2010/0062818 A1 3/2010 Haughay, Jr
2010/0076786 A1 3/2010 Dalton et al.
2010/0121160 A1 5/2010 Stark et al.
2010/0173747 A1 7/2010 Chen et al.
2010/0216168 A1 8/2010 Heinzman et al.
2010/0234184 A1 9/2010 Le Page et al.
2010/0248899 A1 9/2010 Bedell et al.
2010/0248905 A1 9/2010 Lu
2010/0262052 A1 10/2010 Lunau et al.
2010/0268304 A1 10/2010 Matos
2010/0293003 A1 11/2010 Abbo
2010/0298102 A1 11/2010 Bosecker et al.
2010/0326207 A1 12/2010 Topel
2010/0332583 A1 12/2010 Szabo
2011/0010188 A1 1/2011 Yoshikawa et al.
2011/0047108 A1 2/2011 Chakrabarty et al.
2011/0082007 A1 4/2011 Birrell
2011/0087137 A1 4/2011 Hanoun
2011/0119212 A1 5/2011 De Bruin et al.
2011/0172059 A1 7/2011 Watterson et al.
2011/0195819 A1 8/2011 Shaw et al.
2011/0218462 A1 9/2011 Smith
2011/0218814 A1 9/2011 Coats

(56) References Cited

U.S. PATENT DOCUMENTS

2011/0275483 A1 11/2011 Dugan
2011/0281249 A1 11/2011 Gammell et al.
2011/0306846 A1 12/2011 Osorio
2012/0041771 A1 2/2012 Cosentino et al.
2012/0065987 A1 3/2012 Farooq et al.
2012/0116258 A1 5/2012 Lee
2012/0130196 A1 5/2012 Jain et al.
2012/0130197 A1 5/2012 Kugler et al.
2012/0167709 A1 7/2012 Chen et al.
2012/0183939 A1 7/2012 Aragones et al.
2012/0190502 A1 7/2012 Paulus et al.
2012/0232438 A1 9/2012 Cataldi et al.
2012/0253241 A1 10/2012 Levital
2012/0259648 A1* 10/2012 Mallon .................. G16H 10/60 705/2
2012/0259649 A1 10/2012 Mallon et al.
2012/0278759 A1 11/2012 Curl et al.
2012/0295240 A1 11/2012 Walker et al.
2012/0296455 A1 11/2012 Ohnemus et al.
2012/0310667 A1 12/2012 Altman et al.
2013/0066647 A1 3/2013 Andrie
2013/0079925 A1 3/2013 Alaklabi et al.
2013/0083054 A1 4/2013 Bayouk
2013/0108594 A1 5/2013 Martin-Rendon et al.
2013/0110545 A1 5/2013 Smallwood
2013/0123667 A1 5/2013 Komatireddy et al.
2013/0137550 A1 5/2013 Skinner et al.
2013/0137552 A1 5/2013 Kemp et al.
2013/0158368 A1 6/2013 Pacione
2013/0165195 A1 6/2013 Watterson
2013/0178334 A1 7/2013 Brammer
2013/0211281 A1 8/2013 Ross et al.
2013/0211774 A1 8/2013 Bentley
2013/0253943 A1 9/2013 Lee et al.
2013/0274069 A1 10/2013 Watterson et al.
2013/0296987 A1 11/2013 Rogers et al.
2013/0318027 A1 11/2013 Almogy et al.
2013/0332616 A1 12/2013 Landwehr
2013/0345025 A1 12/2013 van der Merwe
2014/0006042 A1 1/2014 Keefe et al.
2014/0011640 A1 1/2014 Dugan
2014/0031174 A1 1/2014 Huang
2014/0038781 A1 2/2014 Foley et al.
2014/0062900 A1 3/2014 Kaula et al.
2014/0074179 A1 3/2014 Heldman et al.
2014/0089836 A1 3/2014 Damani et al.
2014/0108035 A1 4/2014 Akbay
2014/0113261 A1 4/2014 Akiba
2014/0113768 A1 4/2014 Lin et al.
2014/0135173 A1 5/2014 Watterson
2014/0149129 A1 5/2014 Getchius
2014/0155129 A1 6/2014 Dugan
2014/0163439 A1 6/2014 Uryash et al.
2014/0172442 A1 6/2014 Broderick
2014/0172460 A1 6/2014 Kohli
2014/0172514 A1 6/2014 Schumann et al.
2014/0188009 A1 7/2014 Lange et al.
2014/0194250 A1* 7/2014 Reich ................. A63B 24/0084 482/5
2014/0194251 A1 7/2014 Reich et al.
2014/0200414 A1 7/2014 Osorio
2014/0207264 A1 7/2014 Quy
2014/0207486 A1 7/2014 Carty et al.
2014/0228649 A1 8/2014 Rayner et al.
2014/0246499 A1 9/2014 Proud et al.
2014/0256511 A1 9/2014 Smith
2014/0257837 A1 9/2014 Walker et al.
2014/0274565 A1 9/2014 Boyette et al.
2014/0274622 A1 9/2014 Leonhard
2014/0275816 A1 9/2014 Sandmore
2014/0303540 A1* 10/2014 Baym ................... A61F 5/0102 602/23
2014/0309083 A1 10/2014 Dugan
2014/0315689 A1 10/2014 Vauquelin et al.
2014/0322686 A1 10/2014 Kang
2014/0347265 A1 11/2014 Aimone et al.
2014/0371816 A1* 12/2014 Matos .................... G16H 20/30 607/59
2014/0372133 A1 12/2014 Austrum et al.
2015/0025816 A1 1/2015 Ross
2015/0045700 A1 2/2015 Cavanagh et al.
2015/0046192 A1 2/2015 Raduchel
2015/0051721 A1 2/2015 Cheng
2015/0065213 A1 3/2015 Dugan
2015/0073814 A1 3/2015 Linebaugh
2015/0088544 A1 3/2015 Goldberg
2015/0094192 A1 4/2015 Skwortsow et al.
2015/0099458 A1 4/2015 Weisner et al.
2015/0099952 A1 4/2015 Lain et al.
2015/0111644 A1 4/2015 Larson
2015/0112230 A1 4/2015 Iglesias
2015/0112702 A1 4/2015 Joao et al.
2015/0130830 A1 5/2015 Nagasaki
2015/0141200 A1 5/2015 Murray et al.
2015/0142142 A1 5/2015 Aguilera et al.
2015/0149217 A1 5/2015 Kaburagi
2015/0151162 A1 6/2015 Dugan
2015/0157938 A1 6/2015 Domansky et al.
2015/0158549 A1 6/2015 Gros et al.
2015/0161331 A1 6/2015 Oleynik
2015/0161876 A1 6/2015 Castillo
2015/0174446 A1 6/2015 Chiang
2015/0196804 A1 7/2015 Koduri
2015/0196805 A1 7/2015 Koduri
2015/0199494 A1 7/2015 Koduri
2015/0217056 A1 8/2015 Kadavy et al.
2015/0251074 A1 9/2015 Ahmed et al.
2015/0257679 A1 9/2015 Ross
2015/0265209 A1 9/2015 Zhang
2015/0290061 A1 10/2015 Stafford et al.
2015/0331997 A1 11/2015 Joao
2015/0335950 A1 11/2015 Eder
2015/0335951 A1 11/2015 Eder
2015/0339442 A1 11/2015 Oleynik
2015/0341812 A1 11/2015 Dion et al.
2015/0351664 A1 12/2015 Ross
2015/0351665 A1 12/2015 Ross
2015/0360069 A1 12/2015 Marti et al.
2015/0379232 A1 12/2015 Mainwaring et al.
2015/0379430 A1 12/2015 Dirac et al.
2016/0004820 A1 1/2016 Moore
2016/0007885 A1 1/2016 Basta et al.
2016/0015995 A1 1/2016 Leung et al.
2016/0023081 A1 1/2016 Popa-Simil
2016/0045170 A1 2/2016 Migita
2016/0081594 A1 3/2016 Gaddipati
2016/0086500 A1 3/2016 Kaleal, III
2016/0096073 A1 4/2016 Rahman et al.
2016/0117471 A1 4/2016 Belt et al.
2016/0132643 A1 5/2016 Radhakrishna et al.
2016/0140319 A1 5/2016 Stark
2016/0143593 A1 5/2016 Fu et al.
2016/0151670 A1 6/2016 Dugan
2016/0158534 A1 6/2016 Guarraia et al.
2016/0166833 A1 6/2016 Bum
2016/0166881 A1 6/2016 Ridgel et al.
2016/0193306 A1 7/2016 Rabovsky et al.
2016/0197918 A1 7/2016 Turgeman et al.
2016/0213924 A1* 7/2016 Coleman .............. A61N 1/0484
2016/0250519 A1 9/2016 Watterson
2016/0275259 A1 9/2016 Nolan et al.
2016/0287166 A1 10/2016 Tran
2016/0302666 A1 10/2016 Shaya
2016/0302721 A1 10/2016 Wiedenhoefer et al.
2016/0317869 A1 11/2016 Dugan
2016/0322078 A1 11/2016 Bose et al.
2016/0325140 A1 11/2016 Wu
2016/0332028 A1 11/2016 Melnik
2016/0345841 A1 12/2016 Jang et al.
2016/0354636 A1 12/2016 Jang
2016/0361025 A1 12/2016 Reicher et al.
2016/0361597 A1 12/2016 Cole et al.
2016/0373477 A1 12/2016 Moyle
2017/0004260 A1 1/2017 Moturu et al.

(56) References Cited

U.S. PATENT DOCUMENTS

2017/0011179 A1 1/2017 Arshad et al.
2017/0017760 A1 1/2017 Freese et al.
2017/0032092 A1 2/2017 Mink et al.
2017/0033375 A1 2/2017 Ohmori et al.
2017/0042467 A1 2/2017 Herr et al.
2017/0043160 A1 2/2017 Goodall et al.
2017/0046488 A1 2/2017 Pereira
2017/0065851 A1 3/2017 Deluca et al.
2017/0069223 A1 3/2017 Cramer et al.
2017/0080320 A1 3/2017 Smith
2017/0091422 A1 3/2017 Kumar et al.
2017/0095670 A1 4/2017 Ghaffari et al.
2017/0095692 A1 4/2017 Chang et al.
2017/0095693 A1 4/2017 Chang et al.
2017/0100637 A1 4/2017 Princen et al.
2017/0106242 A1 4/2017 Dugan
2017/0113092 A1 4/2017 Johnson
2017/0128769 A1 5/2017 Long et al.
2017/0132947 A1 5/2017 Maeda et al.
2017/0136296 A1 5/2017 Barrera et al.
2017/0136298 A1 5/2017 Bae
2017/0143261 A1 5/2017 Wiedenhoefer et al.
2017/0147752 A1 5/2017 Toru
2017/0147789 A1 5/2017 Wiedenhoefer et al.
2017/0148297 A1 5/2017 Ross
2017/0168555 A1 6/2017 Munoz et al.
2017/0169177 A1 6/2017 Beale
2017/0173391 A1 6/2017 Wiebe
2017/0181698 A1 6/2017 Wiedenhoefer et al.
2017/0190052 A1 7/2017 Jaekel et al.
2017/0202724 A1* 7/2017 De Rossi ............. A61B 5/6811
2017/0209766 A1 7/2017 Riley et al.
2017/0220751 A1 8/2017 Davis
2017/0228517 A1 8/2017 Saliman et al.
2017/0235882 A1 8/2017 Orlov et al.
2017/0235906 A1 8/2017 Dorris et al.
2017/0243028 A1 8/2017 LaFever et al.
2017/0258370 A1 9/2017 Plotnik-Peleg et al.
2017/0262604 A1 9/2017 Francois
2017/0266501 A1 9/2017 Sanders et al.
2017/0270260 A1 9/2017 Shetty
2017/0277841 A1 9/2017 Shankar et al.
2017/0278209 A1 9/2017 Olsen et al.
2017/0282015 A1 10/2017 Wicks et al.
2017/0283508 A1 10/2017 Demopulos et al.
2017/0286621 A1 10/2017 Cox
2017/0296861 A1 10/2017 Burkinshaw
2017/0300654 A1 10/2017 Stein et al.
2017/0304024 A1 10/2017 Nobrega
2017/0312614 A1 11/2017 Tran et al.
2017/0323481 A1 11/2017 Tran et al.
2017/0329917 A1 11/2017 McRaith et al.
2017/0329933 A1 11/2017 Brust
2017/0333755 A1 11/2017 Rider
2017/0337033 A1 11/2017 Duyan et al.
2017/0337334 A1 11/2017 Stanczak
2017/0344726 A1 11/2017 Duffy et al.
2017/0347923 A1 12/2017 Roh
2017/0352157 A1 12/2017 Madabhushi
2017/0360586 A1* 12/2017 Dempers ............... A61F 5/0109
2017/0361165 A1 12/2017 Miller et al.
2017/0367606 A1 12/2017 Lee
2017/0368413 A1 12/2017 Shavit
2018/0017806 A1 1/2018 Wang et al.
2018/0036591 A1 2/2018 King et al.
2018/0036593 A1 2/2018 Ridgel et al.
2018/0052962 A1 2/2018 Van Der Koijk et al.
2018/0052968 A1 2/2018 Hickle et al.
2018/0056104 A1 3/2018 Cromie et al.
2018/0056130 A1 3/2018 Bitran et al.
2018/0060494 A1 3/2018 Dias et al.
2018/0070864 A1 3/2018 Schuster
2018/0071565 A1 3/2018 Gomberg et al.
2018/0071566 A1 3/2018 Gomberg et al.
2018/0071569 A1 3/2018 Gomberg et al.
2018/0071570 A1 3/2018 Gomberg et al.
2018/0071571 A1 3/2018 Gomberg et al.
2018/0071572 A1 3/2018 Gomberg et al.
2018/0071583 A1 3/2018 Paiz
2018/0075205 A1 3/2018 Moturu et al.
2018/0078182 A1 3/2018 Chen
2018/0078843 A1 3/2018 Tran et al.
2018/0085615 A1 3/2018 Astolfi et al.
2018/0085630 A1 3/2018 Capell
2018/0089385 A1* 3/2018 Gupta .................... G16H 70/60
2018/0096111 A1 4/2018 Wells et al.
2018/0099178 A1 4/2018 Schaefer et al.
2018/0102190 A1 4/2018 Hogue et al.
2018/0103859 A1 4/2018 Provenzano
2018/0113985 A1 4/2018 Gandy et al.
2018/0116741 A1 5/2018 Garcia Kilroy et al.
2018/0117417 A1 5/2018 Davis
2018/0130555 A1 5/2018 Chronis et al.
2018/0133551 A1 5/2018 Chang
2018/0140927 A1 5/2018 Kito
2018/0146870 A1 5/2018 Shemesh
2018/0177612 A1 6/2018 Trabish et al.
2018/0178061 A1 6/2018 O'larte et al.
2018/0199855 A1 7/2018 Odame et al.
2018/0200577 A1 7/2018 Dugan
2018/0214729 A1 8/2018 Rubin
2018/0220935 A1 8/2018 Tadano et al.
2018/0228682 A1 8/2018 Bayerlein et al.
2018/0232492 A1 8/2018 Al-Alul et al.
2018/0236307 A1 8/2018 Hyde et al.
2018/0240552 A1 8/2018 Tuyl et al.
2018/0253991 A1 9/2018 Tang et al.
2018/0255110 A1 9/2018 Dowlatkhah et al.
2018/0256079 A1 9/2018 Yang et al.
2018/0263530 A1 9/2018 Jung
2018/0263535 A1 9/2018 Cramer
2018/0263552 A1 9/2018 Graman et al.
2018/0264312 A1 9/2018 Pompile et al.
2018/0271432 A1 9/2018 Auchinleck et al.
2018/0272184 A1 9/2018 Vassilaros et al.
2018/0280784 A1 10/2018 Romeo et al.
2018/0290017 A1 10/2018 Fung
2018/0296143 A1 10/2018 Anderson et al.
2018/0296157 A1 10/2018 Bleich et al.
2018/0318122 A1 11/2018 LeCursi et al.
2018/0326243 A1 11/2018 Badi et al.
2018/0330058 A1 11/2018 Bates
2018/0330810 A1 11/2018 Gamarnik
2018/0330824 A1 11/2018 Athey et al.
2018/0353812 A1 12/2018 Lannon et al.
2018/0360340 A1 12/2018 Rehse et al.
2018/0366225 A1 12/2018 Mansi et al.
2018/0373844 A1 12/2018 Ferrandez-Escamez et al.
2019/0005195 A1 1/2019 Peterson
2019/0009135 A1 1/2019 Wu
2019/0019163 A1 1/2019 Batey et al.
2019/0019573 A1 1/2019 Lake et al.
2019/0019578 A1 1/2019 Vaccaro
2019/0030415 A1 1/2019 Volpe, Jr.
2019/0031284 A1 1/2019 Fuchs
2019/0046794 A1 2/2019 Goodall et al.
2019/0060708 A1 2/2019 Fung
2019/0065970 A1 2/2019 Bonutti et al.
2019/0066832 A1 2/2019 Kang et al.
2019/0076701 A1 3/2019 Dugan
2019/0080802 A1 3/2019 Ziobro et al.
2019/0083846 A1 3/2019 Eder
2019/0088356 A1 3/2019 Oliver et al.
2019/0090744 A1 3/2019 Mahfouz
2019/0096534 A1 3/2019 Joao
2019/0105551 A1 4/2019 Ray
2019/0108912 A1 4/2019 Spurlock, III
2019/0111299 A1 4/2019 Radcliffe et al.
2019/0115097 A1 4/2019 Macoviak et al.
2019/0117128 A1 4/2019 Chen et al.
2019/0117156 A1 4/2019 Howard et al.
2019/0118038 A1 4/2019 Tana et al.
2019/0118066 A1 4/2019 Cardona
2019/0126099 A1 5/2019 Hoang

(56) References Cited

U.S. PATENT DOCUMENTS

2019/0132948 A1 5/2019 Longinotti-Buitoni et al.
2019/0134454 A1 5/2019 Mahoney et al.
2019/0137988 A1 5/2019 Cella et al.
2019/0143191 A1 5/2019 Ran et al.
2019/0143193 A1 5/2019 Kim
2019/0145774 A1 5/2019 Ellis
2019/0163876 A1 5/2019 Remme et al.
2019/0167988 A1 6/2019 Shahriari et al.
2019/0172587 A1 6/2019 Park et al.
2019/0175988 A1 6/2019 Volterrani et al.
2019/0183715 A1 6/2019 Kapure et al.
2019/0200920 A1 7/2019 Tien et al.
2019/0209891 A1 7/2019 Fung
2019/0214119 A1 7/2019 Wachira et al.
2019/0223797 A1 7/2019 Tran
2019/0224528 A1 7/2019 Omid-Zohoor et al.
2019/0228856 A1 7/2019 Leifer
2019/0232108 A1 8/2019 Kovach et al.
2019/0240103 A1 8/2019 Hepler et al.
2019/0240541 A1 8/2019 Denton et al.
2019/0244540 A1 8/2019 Errante et al.
2019/0247718 A1 8/2019 Blevins
2019/0251456 A1 8/2019 Constantin
2019/0261959 A1 8/2019 Frankel
2019/0262084 A1 8/2019 Roh
2019/0269343 A1 9/2019 Ramos Murguialday et al.
2019/0274523 A1 9/2019 Bates et al.
2019/0275368 A1 9/2019 Maroldi
2019/0283247 A1 9/2019 Chang
2019/0290191 A1 9/2019 Leppäluoto et al.
2019/0290964 A1 9/2019 Oren
2019/0304584 A1 10/2019 Savolainen
2019/0307983 A1 10/2019 Goldman
2019/0314681 A1 10/2019 Yang
2019/0344123 A1 11/2019 Rubin et al.
2019/0354632 A1 11/2019 Mital et al.
2019/0362242 A1 11/2019 Pillai et al.
2019/0366146 A1 12/2019 Tong et al.
2019/0371472 A1 12/2019 Blanchard
2019/0374421 A1* 12/2019 Johnson ............... A61B 5/4842
2019/0385199 A1 12/2019 Bender et al.
2019/0388728 A1 12/2019 Wang et al.
2019/0392936 A1 12/2019 Arric et al.
2019/0392939 A1 12/2019 Basta et al.
2020/0005928 A1 1/2020 Daniel
2020/0015736 A1 1/2020 Alhathal
2020/0034665 A1 1/2020 Ghanta
2020/0034707 A1 1/2020 Kivatinos et al.
2020/0038703 A1 2/2020 Cleary et al.
2020/0051446 A1 2/2020 Rubinstein
2020/0054922 A1 2/2020 Azaria
2020/0066390 A1 2/2020 Svendrys et al.
2020/0085300 A1 3/2020 Kwatra et al.
2020/0090802 A1 3/2020 Maron
2020/0093418 A1 3/2020 Kluger et al.
2020/0121987 A1 4/2020 Loh
2020/0129237 A1 4/2020 Erdem
2020/0129808 A1 4/2020 Fomin
2020/0139194 A1 5/2020 Min
2020/0143922 A1 5/2020 Chekroud et al.
2020/0151595 A1 5/2020 Jayalath et al.
2020/0151646 A1 5/2020 De La Fuente Sanchez
2020/0152339 A1 5/2020 Pulitzer et al.
2020/0160198 A1 5/2020 Reeves et al.
2020/0170876 A1 6/2020 Kapure et al.
2020/0176098 A1 6/2020 Lucas et al.
2020/0188774 A1 6/2020 Fung
2020/0197744 A1 6/2020 Schweighofer
2020/0221975 A1 7/2020 Basta et al.
2020/0237291 A1 7/2020 Raja
2020/0237452 A1 7/2020 Wolf et al.
2020/0261763 A1 8/2020 Park
2020/0267487 A1 8/2020 Siva
2020/0275886 A1 9/2020 Mason
2020/0289045 A1 9/2020 Hacking et al.
2020/0289046 A1 9/2020 Hacking et al.
2020/0289879 A1 9/2020 Hacking et al.
2020/0289880 A1 9/2020 Hacking et al.
2020/0289881 A1 9/2020 Hacking et al.
2020/0289889 A1 9/2020 Hacking et al.
2020/0293712 A1 9/2020 Potts et al.
2020/0303063 A1 9/2020 Sharma et al.
2020/0312447 A1 10/2020 Bohn et al.
2020/0320454 A1 10/2020 Almashor
2020/0334972 A1 10/2020 Gopalakrishnan
2020/0346072 A1 11/2020 Shah
2020/0353314 A1 11/2020 Messinger
2020/0357299 A1 11/2020 Patel et al.
2020/0365256 A1 11/2020 Hayashitani et al.
2020/0391080 A1 12/2020 Powers
2020/0395112 A1 12/2020 Ronner
2020/0398083 A1 12/2020 Adelsheim
2020/0401224 A1 12/2020 Cotton
2020/0402662 A1 12/2020 Esmailian et al.
2020/0410374 A1 12/2020 White
2020/0410385 A1 12/2020 Otsuki
2020/0410893 A1 12/2020 Ridington
2020/0411162 A1 12/2020 Lien et al.
2020/0411170 A1 12/2020 Brown
2021/0005224 A1 1/2021 Rothschild et al.
2021/0005319 A1 1/2021 Otsuki et al.
2021/0008413 A1 1/2021 Asikainen et al.
2021/0015560 A1 1/2021 Boddington et al.
2021/0027889 A1 1/2021 Neil et al.
2021/0035674 A1 2/2021 Volosin et al.
2021/0050086 A1 2/2021 Rose et al.
2021/0065855 A1 3/2021 Pepin et al.
2021/0074178 A1 3/2021 Ilan et al.
2021/0076981 A1 3/2021 Hacking et al.
2021/0077860 A1 3/2021 Posnack et al.
2021/0077884 A1 3/2021 De Las Casas Zolezzi et al.
2021/0082554 A1 3/2021 Kalia et al.
2021/0093891 A1 4/2021 Sheng
2021/0098099 A1 4/2021 Neumann
2021/0098129 A1 4/2021 Neumann
2021/0101051 A1 4/2021 Posnack et al.
2021/0106899 A1 4/2021 Willardson
2021/0113890 A1 4/2021 Posnack et al.
2021/0125696 A1 4/2021 Liu et al.
2021/0127974 A1 5/2021 Mason et al.
2021/0128080 A1 5/2021 Mason et al.
2021/0128255 A1 5/2021 Mason et al.
2021/0128978 A1 5/2021 Gilstrom et al.
2021/0134412 A1 5/2021 Guaneri et al.
2021/0134425 A1 5/2021 Mason et al.
2021/0134428 A1 5/2021 Mason
2021/0134429 A1 5/2021 Mason
2021/0134430 A1 5/2021 Mason et al.
2021/0134432 A1 5/2021 Mason et al.
2021/0134456 A1 5/2021 Posnack et al.
2021/0134457 A1 5/2021 Mason et al.
2021/0134463 A1 5/2021 Mason et al.
2021/0138304 A1 5/2021 Mason et al.
2021/0142875 A1 5/2021 Mason et al.
2021/0142893 A1 5/2021 Guaneri et al.
2021/0142898 A1 5/2021 Mason et al.
2021/0142903 A1 5/2021 Mason et al.
2021/0144074 A1 5/2021 Guaneri et al.
2021/0186419 A1 6/2021 Van Ee et al.
2021/0187348 A1 6/2021 Phillips et al.
2021/0202090 A1 7/2021 ODonovan et al.
2021/0202103 A1 7/2021 Bostic et al.
2021/0205660 A1 7/2021 Shavit
2021/0217516 A1 7/2021 Nash
2021/0236020 A1 8/2021 Matijevich et al.
2021/0240853 A1 8/2021 Carlson
2021/0241137 A1 8/2021 Jain et al.
2021/0244998 A1 8/2021 Hacking et al.
2021/0245003 A1 8/2021 Turner
2021/0251562 A1 8/2021 Jain
2021/0272677 A1 9/2021 Barbee
2021/0275386 A1* 9/2021 Ravikumar ............... A61F 5/34
2021/0291010 A1 9/2021 Miller
2021/0338469 A1* 11/2021 Dempers ............... A61F 5/0111

(56) References Cited

U.S. PATENT DOCUMENTS

2021/0343384 A1 11/2021 Purushothaman et al.
2021/0345879 A1 11/2021 Mason et al.
2021/0345975 A1 11/2021 Mason et al.
2021/0350888 A1 11/2021 Guaneri et al.
2021/0350898 A1 11/2021 Mason et al.
2021/0350899 A1 11/2021 Mason et al.
2021/0350901 A1 11/2021 Mason et al.
2021/0350902 A1 11/2021 Mason et al.
2021/0350914 A1 11/2021 Guaneri et al.
2021/0350926 A1 11/2021 Mason et al.
2021/0354002 A1 11/2021 Schaefer
2021/0361514 A1 11/2021 Choi et al.
2021/0366587 A1 11/2021 Mason et al.
2021/0375425 A1 12/2021 Zhang
2021/0383909 A1 12/2021 Mason et al.
2021/0391091 A1 12/2021 Mason
2021/0394011 A1 12/2021 Neuhaus et al.
2021/0398668 A1 12/2021 Chock et al.
2021/0406738 A1 12/2021 O'Donncha et al.
2021/0407670 A1 12/2021 Mason et al.
2021/0407681 A1 12/2021 Mason et al.
2022/0000556 A1 1/2022 Casey et al.
2022/0015838 A1 1/2022 Posnack
2022/0016480 A1 1/2022 Bissonnette et al.
2022/0016482 A1 1/2022 Bissonnette
2022/0016484 A1 1/2022 Bissonnette et al.
2022/0016485 A1 1/2022 Bissonnette
2022/0016486 A1 1/2022 Bissonnette et al.
2022/0020469 A1 1/2022 Tanner
2022/0044806 A1 2/2022 Sanders et al.
2022/0047921 A1* 2/2022 Bissonnette ....... A63B 71/0622
2022/0066548 A1 3/2022 Helot
2022/0079690 A1 3/2022 Mason et al.
2022/0080256 A1 3/2022 Am et al.
2022/0080265 A1 3/2022 Watterson
2022/0096006 A1 3/2022 Wu et al.
2022/0105384 A1 4/2022 Hacking et al.
2022/0105385 A1 4/2022 Hacking et al.
2022/0105390 A1 4/2022 Yuasa
2022/0115133 A1 4/2022 Mason et al.
2022/0117514 A1 4/2022 Kuhn et al.
2022/0118218 A1 4/2022 Bense et al.
2022/0122724 A1 4/2022 Durlach et al.
2022/0126169 A1 4/2022 Mason
2022/0133576 A1 5/2022 Choi et al.
2022/0148725 A1 5/2022 Mason et al.
2022/0158916 A1 5/2022 Mason et al.
2022/0165398 A1 5/2022 Avila-Hernandez et al.
2022/0176039 A1 6/2022 Lintereur et al.
2022/0181004 A1 6/2022 Zilca et al.
2022/0193491 A1 6/2022 Mason
2022/0230729 A1 7/2022 Mason
2022/0238222 A1 7/2022 Neuberg
2022/0238223 A1* 7/2022 Mason .................. G16H 80/00
2022/0258935 A1 8/2022 Kraft
2022/0262483 A1 8/2022 Rosenberg et al.
2022/0262504 A1 8/2022 Bratty et al.
2022/0266094 A1 8/2022 Mason et al.
2022/0270738 A1 8/2022 Mason et al.
2022/0273985 A1 9/2022 Jeong et al.
2022/0273986 A1 9/2022 Mason
2022/0288460 A1 9/2022 Mason
2022/0288461 A1 9/2022 Ashley et al.
2022/0288462 A1 9/2022 Ashley et al.
2022/0293257 A1 9/2022 Guaneri et al.
2022/0300787 A1 9/2022 Wall et al.
2022/0304881 A1 9/2022 Choi et al.
2022/0304882 A1 9/2022 Choi
2022/0305291 A1 9/2022 Hibbard
2022/0305328 A1 9/2022 Choi et al.
2022/0314072 A1 10/2022 Bissonnette et al.
2022/0314075 A1 10/2022 Mason et al.
2022/0323826 A1 10/2022 Khurana
2022/0327714 A1 10/2022 Cook et al.
2022/0327807 A1 10/2022 Cook et al.
2022/0328181 A1 10/2022 Mason et al.
2022/0330823 A1 10/2022 Janssen
2022/0331663 A1 10/2022 Mason
2022/0336077 A1 10/2022 Chen et al.
2022/0338761 A1 10/2022 Maddahi et al.
2022/0339052 A1 10/2022 Kim
2022/0339501 A1 10/2022 Mason et al.
2022/0370851 A1 11/2022 Guidarelli et al.
2022/0384010 A1 12/2022 Kanayama
2022/0384012 A1 12/2022 Mason
2022/0392591 A1 12/2022 Guaneri et al.
2022/0395232 A1 12/2022 Locke
2022/0401783 A1 12/2022 Choi
2022/0415469 A1 12/2022 Mason
2022/0415471 A1 12/2022 Mason
2023/0001268 A1 1/2023 Bissonnette et al.
2023/0013530 A1 1/2023 Mason
2023/0014598 A1 1/2023 Mason et al.
2023/0029639 A1 2/2023 Roy
2023/0047253 A1 2/2023 Gnanasambandam et al.
2023/0048040 A1 2/2023 Hacking et al.
2023/0051751 A1 2/2023 Hacking et al.
2023/0055078 A1 2/2023 Malcolm
2023/0058605 A1 2/2023 Mason
2023/0060039 A1 2/2023 Mason
2023/0072368 A1 3/2023 Mason
2023/0078793 A1 3/2023 Mason
2023/0119461 A1 4/2023 Mason
2023/0190100 A1 6/2023 Stump
2023/0197240 A1 6/2023 Rosenberg
2023/0201656 A1 6/2023 Hacking et al.
2023/0207097 A1 6/2023 Mason
2023/0207124 A1 6/2023 Walsh et al.
2023/0215539 A1 7/2023 Rosenberg et al.
2023/0215552 A1 7/2023 Khotilovich et al.
2023/0218950 A1 7/2023 Belson et al.
2023/0245747 A1 8/2023 Rosenberg et al.
2023/0245748 A1 8/2023 Rosenberg et al.
2023/0245750 A1 8/2023 Rosenberg et al.
2023/0245751 A1 8/2023 Rosenberg et al.
2023/0249599 A1 8/2023 Nicola
2023/0253089 A1 8/2023 Rosenberg et al.
2023/0255555 A1 8/2023 Sundaram et al.
2023/0263428 A1 8/2023 Hull et al.
2023/0274813 A1 8/2023 Rosenberg et al.
2023/0282329 A1 9/2023 Mason et al.
2023/0364472 A1 11/2023 Posnack
2023/0368886 A1 11/2023 Rosenberg
2023/0377710 A1 11/2023 Chen et al.
2023/0377711 A1 11/2023 Rosenberg
2023/0377712 A1 11/2023 Rosenberg
2023/0386639 A1 11/2023 Rosenberg
2023/0390627 A1 12/2023 Bolton
2023/0395231 A1 12/2023 Rosenberg
2023/0395232 A1 12/2023 Rosenberg
2024/0029856 A1 1/2024 Rosenberg
2024/0058651 A1 2/2024 Bissonnette
2024/0177846 A1 5/2024 Gnanasambandam
2024/0203580 A1 6/2024 Mason

FOREIGN PATENT DOCUMENTS

CN 2885238 Y 4/2007
CN 101964151 A 2/2011
CN 201889024 U 7/2011
CN 102670381 A 9/2012
CN 103263336 A 8/2013
CN 103390357 A 11/2013
CN 103473631 A 12/2013
CN 103488880 A 1/2014
CN 103501328 A 1/2014
CN 103721343 A 4/2014
CN 203677851 U 7/2014
CN 104335211 A 2/2015
CN 105263448 A 1/2016
CN 105683977 A 6/2016
CN 103136447 B 8/2016
CN 105894088 A 8/2016
CN 105930668 A 9/2016

(56) References Cited

FOREIGN PATENT DOCUMENTS

| | | | |
|---|---|---|---|
| CN | 205626871 | U | 10/2016 |
| CN | 106127646 | A | 11/2016 |
| CN | 106236502 | A | 12/2016 |
| CN | 106510985 | A | 3/2017 |
| CN | 106621195 | A | 5/2017 |
| CN | 107066819 | A | 8/2017 |
| CN | 107430641 | A | 12/2017 |
| CN | 107551475 | A | 1/2018 |
| CN | 107736982 | A | 2/2018 |
| CN | 107930021 | A | 4/2018 |
| CN | 207220817 | U | 4/2018 |
| CN | 108078737 | A | 5/2018 |
| CN | 208224811 | A | 12/2018 |
| CN | 109191954 | A | 1/2019 |
| CN | 109363887 | A | 2/2019 |
| CN | 208573971 | U | 3/2019 |
| CN | 110148472 | A | 8/2019 |
| CN | 110201358 | A | 9/2019 |
| CN | 110215188 | A | 9/2019 |
| CN | 110322957 | A | 10/2019 |
| CN | 110808092 | A | 2/2020 |
| CN | 110931103 | A | 3/2020 |
| CN | 110993057 | A | 4/2020 |
| CN | 111105859 | A | 5/2020 |
| CN | 111111110 | A | 5/2020 |
| CN | 111370088 | A | 7/2020 |
| CN | 111460305 | A | 7/2020 |
| CN | 111790111 | A | 10/2020 |
| CN | 112071393 | A | 12/2020 |
| CN | 212141371 | U | 12/2020 |
| CN | 112289425 | A | 1/2021 |
| CN | 212624809 | U | 2/2021 |
| CN | 112603295 | A | 4/2021 |
| CN | 213190965 | U | 5/2021 |
| CN | 113384850 | A | 9/2021 |
| CN | 113499572 | A | 10/2021 |
| CN | 215136488 | U | 12/2021 |
| CN | 113885361 | A | 1/2022 |
| CN | 114049961 | A | 2/2022 |
| CN | 114203274 | A | 3/2022 |
| CN | 216258145 | U | 4/2022 |
| CN | 114632302 | A | 6/2022 |
| CN | 114694824 | A | 7/2022 |
| CN | 114898832 | A | 8/2022 |
| CN | 114983760 | A | 9/2022 |
| CN | 217472652 | U | 9/2022 |
| CN | 110270062 | B | 10/2022 |
| CN | 218420859 | U | 2/2023 |
| CN | 115954081 | A | 4/2023 |
| DE | 102018202497 | A1 | 8/2018 |
| DE | 102018211212 | A1 | 1/2019 |
| DE | 102019108425 | B3 | 8/2020 |
| EP | 0383137 | A2 | 8/1990 |
| EP | 0919259 | A1 | 6/1999 |
| EP | 1159989 | A1 | 12/2001 |
| EP | 1391179 | A1 | 2/2004 |
| EP | 1968028 | | 9/2008 |
| EP | 2575064 | A1 | 4/2013 |
| EP | 1909730 | B1 | 4/2014 |
| EP | 2815242 | A4 | 12/2014 |
| EP | 2869805 | A | 5/2015 |
| EP | 2997951 | A1 | 3/2016 |
| EP | 2688472 | B1 | 4/2016 |
| EP | 3323473 | A1 | 5/2018 |
| EP | 3547322 | A1 | 10/2019 |
| EP | 3627514 | A1 | 3/2020 |
| EP | 3671700 | A1 | 6/2020 |
| EP | 3688537 | A1 | 8/2020 |
| EP | 3731733 | A1 | 11/2020 |
| EP | 3984508 | A1 | 4/2022 |
| EP | 3984509 | A1 | 4/2022 |
| EP | 3984510 | A1 | 4/2022 |
| EP | 3984511 | A1 | 4/2022 |
| EP | 3984512 | A1 | 4/2022 |
| EP | 3984513 | A1 | 4/2022 |
| EP | 4054699 | A1 | 9/2022 |
| EP | 4112033 | A1 | 1/2023 |
| FR | 3127393 | A1 | 3/2023 |
| GB | 2512431 | A | 10/2014 |
| GB | 2591542 | B | 3/2022 |
| IN | 201811043670 | A | 7/2018 |
| JP | 2000005339 | A | 1/2000 |
| JP | 2003225875 | A | 8/2003 |
| JP | 2005227928 | A | 8/2005 |
| JP | 2005227928 | A1 | 8/2005 |
| JP | 2009112336 | A | 5/2009 |
| JP | 2013515995 | A | 5/2013 |
| JP | 2014104139 | A | 6/2014 |
| JP | 3193662 | U | 10/2014 |
| JP | 3198173 | U | 6/2015 |
| JP | 5804063 | B2 | 11/2015 |
| JP | 6659831 | B2 | 10/2017 |
| JP | 2018102842 | A | 7/2018 |
| JP | 2019028647 | A | 2/2019 |
| JP | 2019134909 | A | 8/2019 |
| JP | 6573739 | B1 | 9/2019 |
| JP | 2020057082 | A | 4/2020 |
| JP | 6710357 | B1 | 6/2020 |
| JP | 6775757 | B1 | 10/2020 |
| JP | 2021026768 | A | 2/2021 |
| JP | 2021027917 | A | 2/2021 |
| JP | 6871379 | B2 | 5/2021 |
| JP | 2022521378 | A | 4/2022 |
| JP | 3238491 | U | 7/2022 |
| JP | 7198364 | B2 | 12/2022 |
| JP | 7202474 | B2 | 1/2023 |
| JP | 7231750 | B2 | 3/2023 |
| JP | 7231751 | B2 | 3/2023 |
| JP | 7231752 | B2 | 3/2023 |
| KR | 20020009724 | A | 2/2002 |
| KR | 200276919 | Y1 | 5/2002 |
| KR | 20020065253 | A | 8/2002 |
| KR | 100582596 | B1 | 5/2006 |
| KR | 101042258 | B1 | 6/2011 |
| KR | 20110099953 | A | 9/2011 |
| KR | 101258250 | B1 | 4/2013 |
| KR | 101325581 | B1 | 11/2013 |
| KR | 20140128630 | A | 11/2014 |
| KR | 20150017693 | A | 2/2015 |
| KR | 20150078191 | A | 7/2015 |
| KR | 101580071 | B1 | 12/2015 |
| KR | 101647620 | B1 | 8/2016 |
| KR | 20160093990 | A | 8/2016 |
| KR | 20170038837 | A | 4/2017 |
| KR | 20180004928 | A | 1/2018 |
| KR | 20190011885 | A | 2/2019 |
| KR | 20190029175 | A | 3/2019 |
| KR | 101988167 | B1 | 6/2019 |
| KR | 102116664 | B1 | 7/2019 |
| KR | 101969392 | B1 | 8/2019 |
| KR | 102055279 | B1 | 12/2019 |
| KR | 20200019548 | A | 2/2020 |
| KR | 102088333 | B1 | 3/2020 |
| KR | 102116968 | B1 | 3/2020 |
| KR | 20200025290 | A | 3/2020 |
| KR | 20200029180 | A | 3/2020 |
| KR | 102097190 | B1 | 4/2020 |
| KR | 102162522 | B1 | 4/2020 |
| KR | 102142713 | B1 | 5/2020 |
| KR | 20200056233 | A | 5/2020 |
| KR | 102120828 | B1 | 6/2020 |
| KR | 102121586 | B1 | 6/2020 |
| KR | 20200119665 | A | 10/2020 |
| KR | 102173553 | B1 | 11/2020 |
| KR | 102180079 | B1 | 11/2020 |
| KR | 102224618 | B1 | 11/2020 |
| KR | 102188766 | B1 | 12/2020 |
| KR | 102196793 | B1 | 12/2020 |
| KR | 20210006212 | A | 1/2021 |
| KR | 102224188 | B1 | 3/2021 |
| KR | 102246049 | B1 | 4/2021 |
| KR | 102246050 | B1 | 4/2021 |
| KR | 102246051 | B1 | 4/2021 |
| KR | 102246052 | B1 | 4/2021 |

(56) References Cited

FOREIGN PATENT DOCUMENTS

| | | | |
|---|---|---|---|
| KR | 20210052028 | A | 5/2021 |
| KR | 102264498 | B1 | 6/2021 |
| KR | 102352602 | B1 | 1/2022 |
| KR | 102352603 | B1 | 1/2022 |
| KR | 102352604 | B1 | 1/2022 |
| KR | 20220004639 | A | 1/2022 |
| KR | 102387577 | B1 | 4/2022 |
| KR | 102421437 | B1 | 7/2022 |
| KR | 20220102207 | A | 7/2022 |
| KR | 102427545 | B1 | 8/2022 |
| KR | 102467495 | B1 | 11/2022 |
| KR | 102467496 | B1 | 11/2022 |
| KR | 102469723 | B1 | 11/2022 |
| KR | 102471990 | B1 | 11/2022 |
| KR | 20220145989 | A | 11/2022 |
| KR | 20220156134 | A | 11/2022 |
| KR | 102502744 | B1 | 2/2023 |
| KR | 20230019349 | A | 2/2023 |
| KR | 20230019350 | A | 2/2023 |
| KR | 20230026556 | A | 2/2023 |
| KR | 20230026668 | A | 2/2023 |
| KR | 20230040526 | | 3/2023 |
| KR | 20230050506 | A | 4/2023 |
| KR | 20230056118 | A | 4/2023 |
| KR | 102528503 | B1 | 5/2023 |
| KR | 102531930 | B1 | 5/2023 |
| KR | 102532766 | B1 | 5/2023 |
| KR | 102539190 | B1 | 6/2023 |
| RU | 2014131288 | A | 2/2016 |
| RU | 2607953 | C2 | 1/2017 |
| TW | M474545 | U | 3/2014 |
| TW | M638437 | U | 3/2023 |
| WO | 0149235 | A2 | 7/2001 |
| WO | 0151083 | A2 | 7/2001 |
| WO | 2001050387 | A1 | 7/2001 |
| WO | 2001056465 | A1 | 8/2001 |
| WO | 02062211 | A2 | 8/2002 |
| WO | 02093312 | A2 | 11/2002 |
| WO | 2003043494 | | 5/2003 |
| WO | 2005018453 | A1 | 3/2005 |
| WO | 2005074369 | A2 | 8/2005 |
| WO | 2006004430 | A2 | 1/2006 |
| WO | 2007102709 | A1 | 9/2007 |
| WO | 2008114291 | A1 | 9/2008 |
| WO | 2008140780 | A1 | 11/2008 |
| WO | 2009003170 | A1 | 12/2008 |
| WO | 2009008968 | A1 | 1/2009 |
| WO | 2011025322 | A2 | 3/2011 |
| WO | 2012128801 | A1 | 9/2012 |
| WO | 2013002568 | A2 | 1/2013 |
| WO | 2023164292 | A1 | 3/2013 |
| WO | 2013122839 | A1 | 8/2013 |
| WO | 2014011447 | A1 | 1/2014 |
| WO | 2014163976 | A1 | 10/2014 |
| WO | 2015026744 | A1 | 2/2015 |
| WO | 2015065298 | A1 | 5/2015 |
| WO | 2015082555 | A1 | 6/2015 |
| WO | 2016151364 | A1 | 9/2016 |
| WO | 2016154318 | A1 | 9/2016 |
| WO | 2017030781 | A1 | 2/2017 |
| WO | 2017166074 | A1 | 5/2017 |
| WO | 2017091691 | A1 | 6/2017 |
| WO | 2017165238 | A1 | 9/2017 |
| WO | 2018027080 | A1 | 2/2018 |
| WO | 2018081795 | A1 | 5/2018 |
| WO | 2018171853 | A1 | 9/2018 |
| WO | 2019022706 | A1 | 1/2019 |
| WO | 2019204876 | A1 | 4/2019 |
| WO | 2019143940 | A1 | 7/2019 |
| WO | 2020014710 | A2 | 1/2020 |
| WO | 2020185769 | A1 | 3/2020 |
| WO | 2020075190 | A1 | 4/2020 |
| WO | 2020130979 | A1 | 6/2020 |
| WO | 2020149815 | A2 | 7/2020 |
| WO | 2020229705 | A1 | 11/2020 |
| WO | 2020245727 | A1 | 12/2020 |
| WO | 2020249855 | A1 | 12/2020 |
| WO | 2020252599 | A1 | 12/2020 |
| WO | 2020256577 | A1 | 12/2020 |
| WO | 2021021447 | A1 | 2/2021 |
| WO | 2021022003 | A1 | 2/2021 |
| WO | 2021038980 | A1 | 3/2021 |
| WO | 2021055427 | A1 | 3/2021 |
| WO | 2021055491 | A1 | 3/2021 |
| WO | 2021061061 | A1 | 4/2021 |
| WO | 2021081094 | A1 | 4/2021 |
| WO | 2021090267 | A1 | 5/2021 |
| WO | 2021138620 | A1 | 7/2021 |
| WO | 2021216881 | A1 | 10/2021 |
| WO | 2021236542 | A1 | 11/2021 |
| WO | 2021236961 | A1 | 11/2021 |
| WO | 2021262809 | A1 | 12/2021 |
| WO | 2022047006 | A1 | 3/2022 |
| WO | 2022092493 | A1 | 5/2022 |
| WO | 2022092494 | A1 | 5/2022 |
| WO | 2022212883 | A1 | 10/2022 |
| WO | 2022212921 | A1 | 10/2022 |
| WO | 2022216498 | A1 | 10/2022 |
| WO | 2022251420 | A1 | 12/2022 |
| WO | 2023008680 | A1 | 2/2023 |
| WO | 2023008681 | A1 | 2/2023 |
| WO | 2023022319 | A1 | 2/2023 |
| WO | 2023022320 | A1 | 2/2023 |
| WO | 2023052695 | A1 | 4/2023 |
| WO | 2023091496 | A1 | 5/2023 |
| WO | 2023215155 | A1 | 11/2023 |
| WO | 2023230075 | A1 | 11/2023 |
| WO | 2024013267 | A1 | 1/2024 |
| WO | 2024107807 | A1 | 5/2024 |

OTHER PUBLICATIONS

Davenport et al., "The Potential for Artificial Intelligence in Healthcare", 2019, Future Healthcare Journal 2019, vol. 6, No. 2: Year: 2019, pp. 1-5.

Ahmed et al., "Artificial Intelligence With Multi-Functional Machine Learning Platform Development for Better Healthcare and Precision Medicine", 2020, Database (Oxford), 2020:baaa010. doi: 10.1093/database/baaa010 (Year: 2020), pp. 1-35.

Ruiz Ivan et al., "Towards a physical rehabilitation system using a telemedicine approach", Computer Methods in Biomechanics and Biomedical Engineering: Imaging & Visualization, vol. 8, No. 6, Jul. 28, 2020, pp. 671-680, XP055914810.

De Canniere Helene et al., "Wearable Monitoring and Interpretable Machine Learning Can Objectively Track Progression in Patients during Cardiac Rehabilitation", Sensors, vol. 20, No. 12, Jun. 26, 2020, XP055914617, pp. 1-15.

Boulanger Pierre et al., "A Low-cost Virtual Reality Bike for Remote Cardiac Rehabilitation", Dec. 7, 2017, Advances in Biometrics: International Conference, ICB 2007, Seoul, Korea, pp. 155-166.

Yin Chieh et al., "A Virtual Reality-Cycling Training System for Lower Limb Balance Improvement", BioMed Research International, vol. 2016, pp. 1-10.

International Searching Authority, Search Report and Written Opinion for International Application No. PCT/US2021/038617, Mailed Oct. 15, 2021, 12 pages.

Jeong et al., "Computer-assisted upper extremity training using interactive biking exercise (iBikE) platform," Sep. 2012, pp. 1-5, 34th Annual International Conference of the IEEE EMBS.

Alcaraz et al., "Machine Learning as Digital Therapy Assessment for Mobile Gait Rehabilitation," 2018 IEEE 28th International Workshop on Machine Learning for Signal Processing (MLSP), Aalborg, Denmark, 2018, 6 pages.

Androutsou et al., "A Smartphone Application Designed to Engage the Elderly in Home-Based Rehabilitation," Frontiers in Digital Health, Sep. 2020, vol. 2, Article 15, 13 pages.

Silva et al., "SapoFitness: A mobile health application for dietary evaluation," 2011 IEEE 13th International Conference on U e-Health Networking, Applications and Services, Columbia, MO, USA, 2011, 6 pages.

(56) References Cited

OTHER PUBLICATIONS

Wang et al., "Interactive wearable systems for upper body rehabilitation: a systematic review," Journal of NeuroEngineering and Rehabilitation, 2017, 21 pages.
Marzolini et al., "Eligibility, Enrollment, and Completion of Exercise-Based Cardiac Rehabilitation Following Stroke Rehabilitation: What Are the Barriers?," Physical Therapy, vol. 100, No. 1, 2019, 13 pages.
Nijjar et al., "Randomized Trial of Mindfulness-Based Stress Reduction in Cardiac Patients Eligible for Cardiac Rehabilitation," Scientific Reports, 2019, 12 pages.
Lara et al., "Human-Robot Sensor Interface for Cardiac Rehabilitation," IEEE International Conference on Rehabilitation Robotics, Jul. 2017, 8 pages.
Ishraque et al., "Artificial Intelligence-Based Rehabilitation Therapy Exercise Recommendation System," 2018 IEEE MIT Undergraduate Research Technology Conference (URTC), Cambridge, MA, USA, 2018, 5 pages.
Zakari et al., "Are There Limitations to Exercise Benefits in Peripheral Arterial Disease?," Frontiers in Cardiovascular Medicine, Nov. 2018, vol. 5, Article 173, 12 pages.
You et al., "Including Blood Vasculature into a Game-Theoretic Model of Cancer Dynamics," Games 2019, 10, 13, 22 pages.
Jeong et al., "Computer-assisted upper extremity training using interactive biking exercise (iBikE) platform," Sep. 2012, 34th Annual International Conference of the IEEE EMBS, 5 pages.
International Search Report and Written Opinion for PCT/US2023/014137, dated Jun. 9, 2023, 13 pages.
Website for "Esino 2022 Physical Therapy Equipments Arm Fitness Indoor Trainer Leg Spin Cycle Machine Exercise Bike for Elderly," https://www.made-in-china.com/showroom/esinogroup/product-detailYdZlwGhCMKVR/China-Esino-2022-Physical-Therapy-Equipments-Arm-Fitness-Indoor-Trainer-Leg-Spin-Cycle-Machine-Exercise-Bike-for-Elderly.html, retrieved on Aug. 29, 2023, 5 pages.
Abedtash, "An Interoperable Electronic Medical Record-Based Platform for Personalized Predictive Analytics", ProQuest LLC, Jul. 2017, 185 pages.
Barrett et al., "Artificial intelligence supported patient self-care in chronic heart failure: a paradigm shift from reactive to predictive, preventive and personalised care," EPMA Journal (2019), pp. 445-464.
Oerkild et al., "Home-based cardiac rehabilitation is an attractive alternative to no cardiac rehabilitation for elderly patients with coronary heart disease: results from a randomised clinical trial," BMJ Open Accessible Medical Research, Nov. 22, 2012, pp. 1-9.
Bravo-Escobar et al., "Effectiveness and safety of a home-based cardiac rehabilitation programme of mixed surveillance in patients with ischemic heart disease at moderate cardiovascular risk: A randomised, controlled clinical trial," BMC Cardiovascular Disorders, 2017, pp. 1-11, vol. 17:66.
Thomas et al., "Home-Based Cardiac Rehabilitation," Circulation, 2019, pp. e69-e89, vol. 140.
Thomas et al., "Home-Based Cardiac Rehabilitation," Journal of the American College of Cardiology, Nov. 1, 2019, pp. 133-153, vol. 74.
Thomas et al., "Home-Based Cardiac Rehabilitation," HHS Public Access, Oct. 2, 2020, pp. 1-39.
Dittus et al., "Exercise-Based Oncology Rehabilitation: Leveraging the Cardiac Rehabilitation Model," Journal of Cardiopulmonary Rehabilitation and Prevention, 2015, pp. 130-139, vol. 35.
Chen et al., "Home-based cardiac rehabilitation improves quality of life, aerobic capacity, and readmission rates in patients with chronic heart failure," Medicine, 2018, pp. 1-5 vol. 97:4.
Lima de Melo Ghisi et al., "A systematic review of patient education in cardiac patients: Do they increase knowledge and promote health behavior change?," Patient Education and Counseling, 2014, pp. 1-15.
Fang et al., "Use of Outpatient Cardiac Rehabilitation Among Heart Attack Survivors—20 States and the District of Columbia, 2013 and Four States, 2015," Morbidity and Mortality Weekly Report, vol. 66, No. 33, Aug. 25, 2017, pp. 869-873.
Beene et al., "AI and Care Delivery: Emerging Opportunities for Artificial Intelligence to Transform How Care Is Delivered," Nov. 2019, American Hospital Association, pp. 1-12.
Jennifer Bresnick, "What is the Role of Natural Language Processing in Healthcare?", pp. 1-7, published Aug. 18, 2016, retrieved on Feb. 1, 2022 from https://healthitanalytics.com/ featu res/what-is-the-role-of-natural-language-processing-in-healthcare.
Alex Bellec, "Part-of-Speech tagging tutorial with the Keras Deep Learning library," pp. 1-16, published Mar. 27, 2018, retrieved on Feb. 1, 2022 from https://becominghuman.ai/part-of-speech-tagging-tutorial-with-the-keras-deep-learning-library-d7f93fa05537.
Kavita Ganesan, All you need to know about text preprocessing for NLP and Machine Learning, pp. 1-14, published Feb. 23, 2019, retrieved on Feb. 1, 2022 from https:// towardsdatascience.com/all-you-need-to-know-about-text-preprocessing-for-nlp-and-machine-learning-bcl c5765ff67.
Badreesh Shetty, "Natural Language Processing (NPL) for Machine Learning," pp. 1-13, published Nov. 24, 2018, retrieved on Feb. 1, 2022 from https://towardsdatascience. com/natural-language-processing-nlp-for-machine-learning-d44498845d5b.
International Search Report and Written Opinion for International Application No. PCT/US2021/032807, Date of Mailing Sep. 6, 2021, 11 pages.
Gerbild et al., "Physical Activity to Improve Erectile Dysfunction: A Systematic Review of Intervention Studies," Sexual Medicine, 2018, 15 pages.
Website for "Pedal Exerciser", p. 1, retrieved on Sep. 9, 2022 from https://www.vivehealth.com/collections/physical-therapy-equipment/products/pedalexerciser.
Website for "Functional Knee Brace with ROM", p. 1, retrieved on Sep. 9, 2022 from http://medicalbrace.gr/en/product/functional-knee-brace-with-goniometer-mbtelescopicknee/.
Website for "ComfySplints Goniometer Knee", pp. 1-5, retrieved on Sep. 9, 2022 from https://www.comfysplints.com/product/knee-splints/.
Website for "BMI FlexEze Knee Corrective Orthosis (KCO)", pp. 1-4, retrieved on Sep. 9, 2022 from https://orthobmi.com/products/bmi-flexeze%C2%AE-knee-corrective-orthosis-kco.
Website for "Neoprene Knee Brace with goniometer—Patella ROM MB.4070", pp. 1-4, retrieved on Sep. 9, 2022 from https://www.fortuna.com.gr/en/product/neoprene-knee-brace-with-goniometer-patella-rom-mb-4070/.
Kuiken et al., "Computerized Biofeedback Knee Goniometer: Acceptance and Effect on Exercise Behavior in Post-total Knee Arthroplasty Rehabilitation," Biomedical Engineering Faculty Research and Publications, 2004, pp. 1-10.
Ahmed et al., "Artificial intelligence with multi-functional machine learning platform development for better healthcare and precision medicine," Database, 2020, pp. 1-35.
Davenport et al., "The potential for artificial intelligence in healthcare," Digital Technology, Future Healthcare Journal, 2019, pp. 1-5, vol. 6, No. 2.
Website for "OxeFit XS1", pp. 1-3, retrieved on Sep. 9, 2022 from https://www.oxefit.com/xs1.
Website for "Preva Mobile", pp. 1-6, retrieved on Sep. 9, 2022 from https://www.precor.com/en-us/resources/introducing-preva-mobile.
Website for "J-Bike", pp. 1-3, retrieved on Sep. 9, 2022 from https://www.magneticdays.com/en/cycling-for-physical-rehabilitation.
Website for "Excy", pp. 1-12, retrieved on Sep. 9, 2022 from https://excy.com/portable-exercise-rehabilitation-excy-xcs-pro/.
Website for "OxeFit XP1", p. 1, retrieved on Sep. 9, 2022 from https://www.oxefit.com/xp1.
Ahmed et al., "Artificial Intelligence With Multi-Functional Machine Learning Platform Development for Better Healthcare and Precision Medicine," Database (Oxford), 2020, pp. 1-35, vol. 2020.
Davenport et al., "The Potential for Artificial Intelligence in Healthcare," Future Healthcare Journal, 2019, pp. 94-98, vol. 6, No. 2.
Jeong et al., "Remotely controlled biking is associated with improved adherence to prescribed cycling speed," Technology and Health Care 23, 2015, 7 pages.

(56) References Cited

OTHER PUBLICATIONS

Laustsen et al., "Telemonitored exercise-based cardiac rehabilitation improves physical capacity and health-related quality of life," Journal of Telemedicine and Telecare, 2020, DOI: 10.1177/1357633X18792808, 9 pages.

Blasiak et al., "CURATE.AI: Optimizing Personalized Medicine with Artificial Intelligence," SLAS Technology: Translating Life Sciences Innovation, 2020, 11 pages.

Joudaki et al., "Using Data Mining to Detect Health Care Fraud and Abuse: A Review of Literature", Global Journal of Health Science, vol. 7, No. 1, 2015 (Year: 2015).

Marios et al., "The effect of tele-monitoring on exercise training adherence, functional capacity, quality of life and glycemic control in patients with type II diabetes," Journal of Sports Science and Medicine, Mar. 2012, vol. 11, 6 pages.

Fraass et al, "The impact of treatment complexity and computer-control delivery technology on treatment delivery errors," pp. 651-659, Oct. 1, 1998, International Journal of Radiation Oncology Biology Physics, vol. 42, Issue 3, https://doi.org/:10.1016/s0360-3016(98)00244-2. PMID: 9806527.

Marchal-Crespo et al, "Review of control strategies for robotic movement training after neurologic injury," pp. 1-15, Jun. 16, 2009, Journal of NeuroEngineering and Rehabilitation, vol. 6, No. 20, https://doi.org/10.1186/1743-0003-6-20.

Chrif et al, "Control design for a lower-limb paediatric therapy device using linear motor technology," pp. 119-127, Jun. 9, 2017, Biomedical Usignal Processing and Control, vol. 38, https://www.sciencedirect.com/science/article/pii/S1746809417301027.

International Preliminary Report on Patentability of International Application No. PCT/2024/022550, Date of Mailing Sep. 20, 2025, 7 pages.

Shen et al, "Intelligent inverse treatment planning via deep reinforcement learning, a proof-of-principle study in high dose-rate brachytherapy for cervical cancer," pp. 1-17, May 29, 2019, Phys. Med. Biol. vol. 64, No. 115013.

Karboub et al, "A Machine Learning Based Discharge Prediction of Cardiovascular Diseases Patients in Intensive Care Units.," pp. 1-23, May 24, 2022, Healthcare (Basel, Switzerland) MDPI, vol. 10(6), No. 966, https://doi.org/10.3390/healthcare10060966.

Chrif et al., "Control design for a lower-limb paediatric therapy device using linear motor technology," Article, 2017, pp. 119-127, Science Direct, Switzerland.

Robben et al., "Delta Features From Ambient Sensor Data are Good Predictors of Change in Functional Health," Article, 2016, pp. 2168-2194, vol. 21, No. 4, IEEE Journal of Biomedical and Health Informatics.

Kantoch et al., "Recognition of Sedentary Behavior by Machine Learning Analysis of Wearable Sensors during Activities of Daily Living for Telemedical Assessment of Cardiovascular Risk," Article, 2018, 17 pages, Sensors, Poland.

Warburton et al., "International Launch of the PAR-•Q+ and ePARmed-•X+ Validation of the PAR-•Q+ and ePARmed••X+," Health & Fitness Journal of Canada, 2011, 9 pages, vol. 4, No. 2.

Abidi, Samina; A Knowledge-Modeling Approach to Integrate Multiple Clinical Practice Guidelines to Provide Evidence-Based Clinical Decision Support for Managing Comorbid Conditions; Journal of Medical Systems 41.12: 1-19. Springer Nature B.V. (Dec. 2017) (Year: 2017).

Fuller, Carole G.; Diagnosis and treatment considerations with comorbid developmentally disabled populations; Journal of Clinical Psychology 54.1: 1-10. John Wiley and Sons Inc. (Jan. 1998) (Year: 1998).

He, Jianxing et al. The practical implementation of artificial intelligence technologies in medicine. Nature Medicine; New York vol. 25, Iss. 1. Jan. 2019. (Year: 2019).

CG. Acampora, D. J. Cook, P. Rashidi and A. V. Vasilakos, "A Survey on Ambient Intelligence in Healthcare," in Proceedings of the IEEE, vol. 101, No. 12, pp. 2470-2494, Dec. 2013, doi: 10.1109/JPROC.2013.2262913. (Year: 2013).

H. Demirkan, "A Smart Healthcare Systems Framework," in IT Professional, vol. 15, No. 5, pp. 38-45, Sep.-Oct. 2013, doi: 10.1109/MITP.2013.35. (Year: 2013).

W. Rashwan, J. Fowler and A. Arisha, "A Multi-Method Scheduling Framework for Medical Staff," 2018 Winter Simulation Conference (WSC), Gothenburg, Sweden, 2018, pp. 1464-1475, doi: 10.1109/WSC.2018.8632247. (Year: 2018).

* cited by examiner

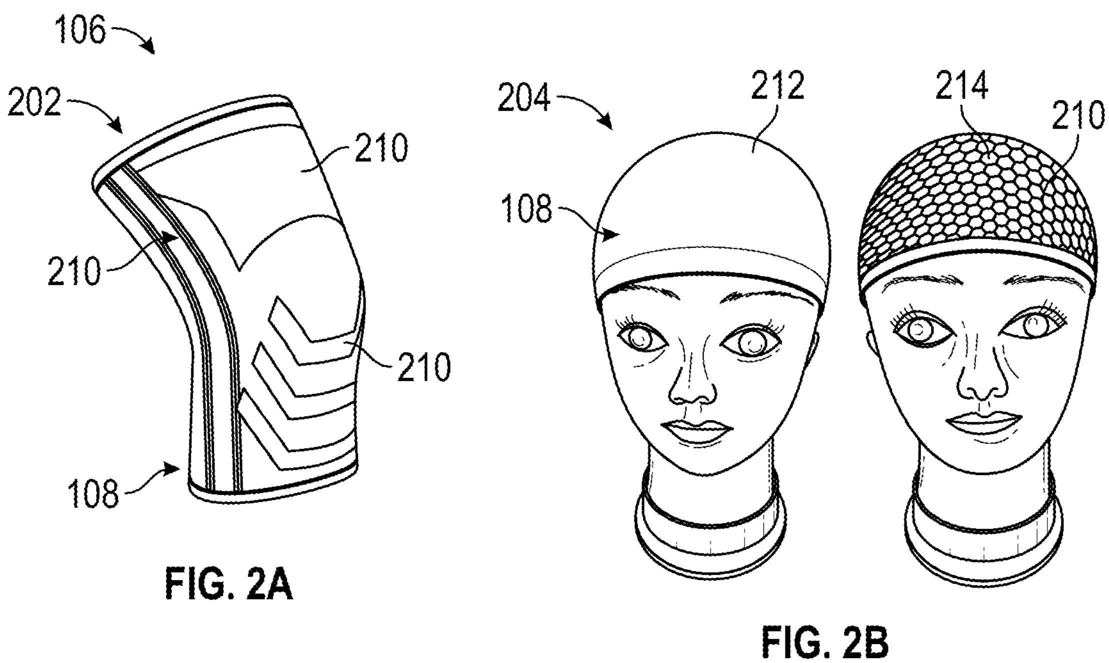
FIG. 2A
FIG. 2B
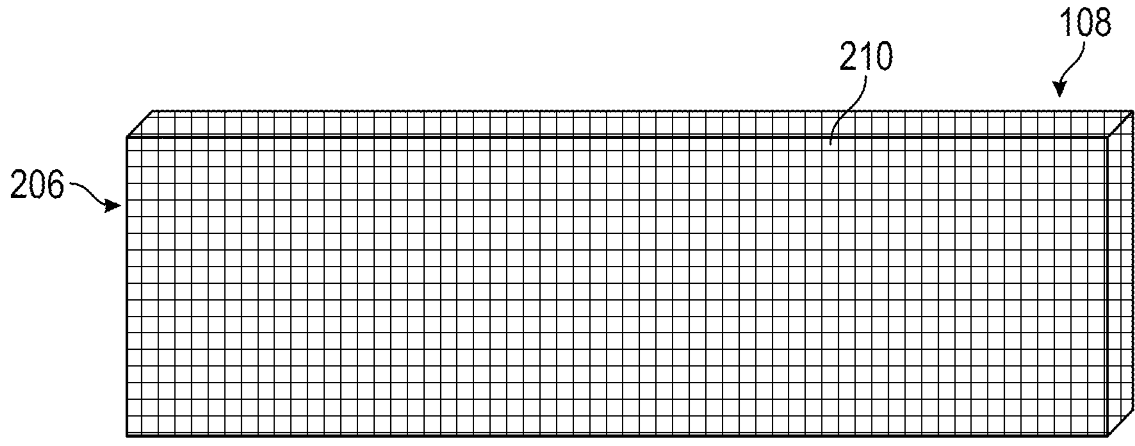
FIG. 2C
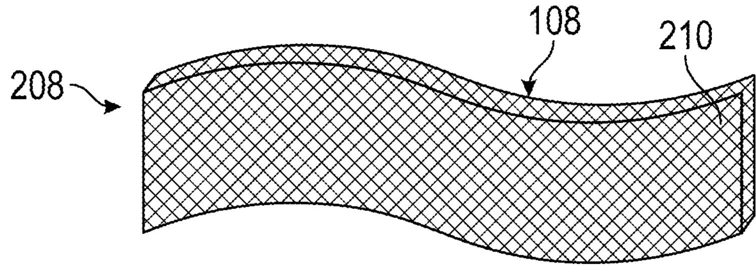
FIG. 2D

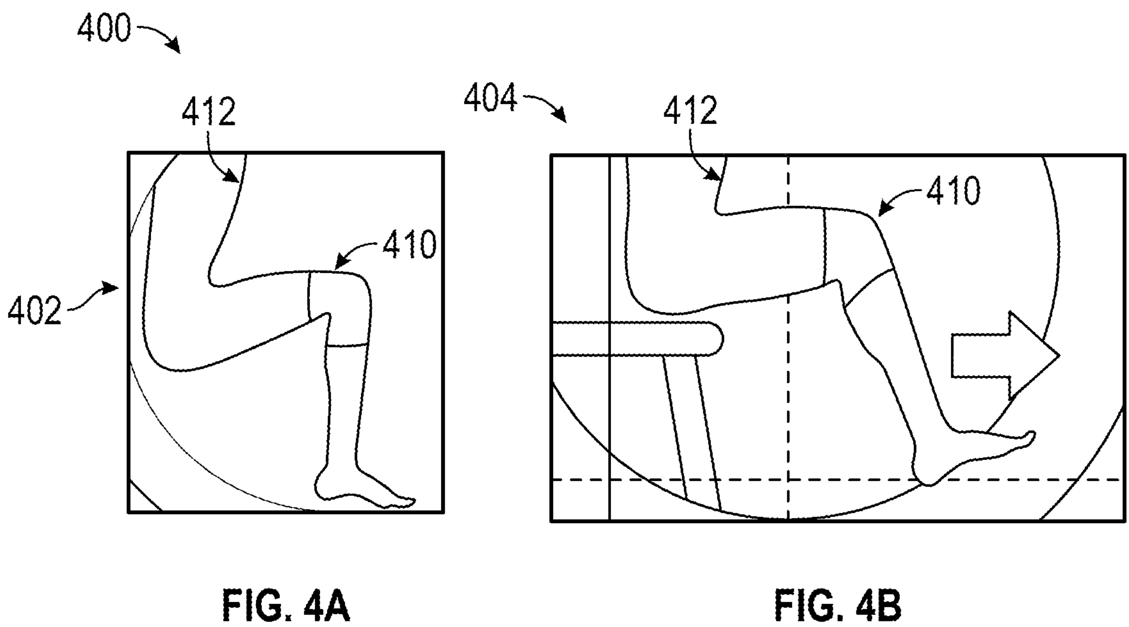
FIG. 4A
FIG. 4B
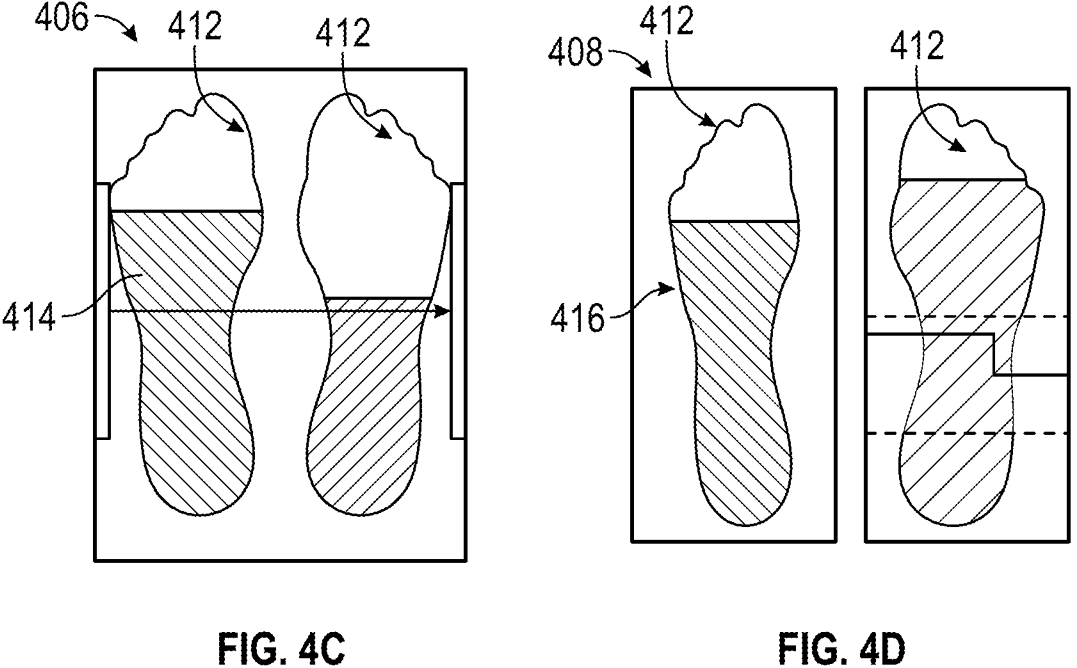
FIG. 4C
FIG. 4D

SYSTEM AND METHOD TO ENABLE REMOTE ADJUSTMENT OF A DEVICE DURING A TELEMEDICINE SESSION

CROSS-REFERENCES TO RELATED APPLICATIONS

This application is a continuation-in-part of U.S. patent application Ser. No. 17/021,895, filed Sep. 15, 2020, titled "Telemedicine for Orthopedic Treatment," which claims priority to and the benefit of U.S. Provisional Patent Application Ser. No. 62/910,232, filed Oct. 3, 2019, titled "Telemedicine for Orthopedic Treatment," the entire disclosures of which are hereby incorporated by reference for all purposes. This application also claims priority to and the benefit of U.S. Provisional Patent Application Ser. No. 63/029,896, filed May 26, 2020, titled "System and Method to Enable Remote Adjustment of a Device During a Telemedicine Session," the entire disclosure of which is hereby incorporated by reference for all purposes.

TECHNICAL FIELD

This disclosure relates generally to a system and a method for enabling a remote adjustment of a device during a telemedicine session.

BACKGROUND

Remote medical assistance, also referred to, inter alia, as remote medicine, telemedicine, telemed, telmed, tel-med, or telehealth, is an at least two-way communication between a healthcare provider or providers, such as a physician or a physical therapist, and a patient using audio and/or audiovisual and/or other sensorial or perceptive (e.g., tactile, gustatory, haptic, pressure-sensing-based or electromagnetic (e.g., neurostimulation) communications (e.g., via a computer, a smartphone, or a tablet). Telemedicine may aid a patient in performing various aspects of a rehabilitation regimen for a body part. The patient may use a patient interface in communication with an assistant interface for receiving the remote medical assistance via audio, visual, audiovisual, or other communications described elsewhere herein. Any reference herein to any particular sensorial modality shall be understood to include and to disclose by implication a different one or more sensory modalities.

Telemedicine is an option for healthcare providers to communicate with patients and provide patient care when the patients do not want to or cannot easily go to the healthcare providers' offices. Telemedicine, however, has substantive limitations as the healthcare providers cannot conduct physical examinations of the patients. Rather, the healthcare providers must rely on verbal communication and/or limited remote observation of the patients.

SUMMARY

In general, the present disclosure provides a system and method for remote examination of patients through augmentation.

An aspect of the disclosed embodiments includes a computer-implemented system comprising a treatment device, a patient interface, and a processing device. The treatment device is configured to be manipulated by a user while the user performs a treatment plan. The patient interface comprises an output device configured to present telemedicine information associated with a telemedicine session. The processing device is configured to receive a treatment plan for a patient; during the telemedicine session, use the treatment plan to generate at least one parameter; and responsive to at least one trigger condition occurring, control at least one operation of the device.

Another aspect of the disclosed embodiments includes a system for enabling a remote adjustment of a device. The system comprises a control system comprising one or more processing devices operatively coupled to the device. The one or more processing devices are configured to receive a treatment plan for a patient; use the treatment plan to generate at least one parameter; and responsive to at least one trigger condition occurring, control at least one operation of the device.

Another aspect of the disclosed embodiments includes a system that includes a processing device and a memory communicatively coupled to the processing device and capable of storing instructions. The processing device executes the instructions to perform any of the methods, operations, or steps described herein.

Another aspect of the disclosed embodiments includes a tangible, non-transitory computer-readable medium storing instructions that, when executed, cause a processing device to perform any of the methods, operations, or steps described herein.

BRIEF DESCRIPTION OF THE DRAWINGS

For a more complete understanding of this disclosure and its advantages, reference is now made to the following description, taken in conjunction with the accompanying drawings. It is emphasized that, according to common practice, the various features of the drawings are not to-scale. On the contrary, the dimensions of the various features are arbitrarily expanded or reduced for clarity.

FIGS. 2A-D generally illustrate example treatment devices according to certain aspects of this disclosure.

FIGS. 4A-D generally illustrate example augmented images according to certain aspects of this disclosure.

NOTATION AND NOMENCLATURE

Figure 1:
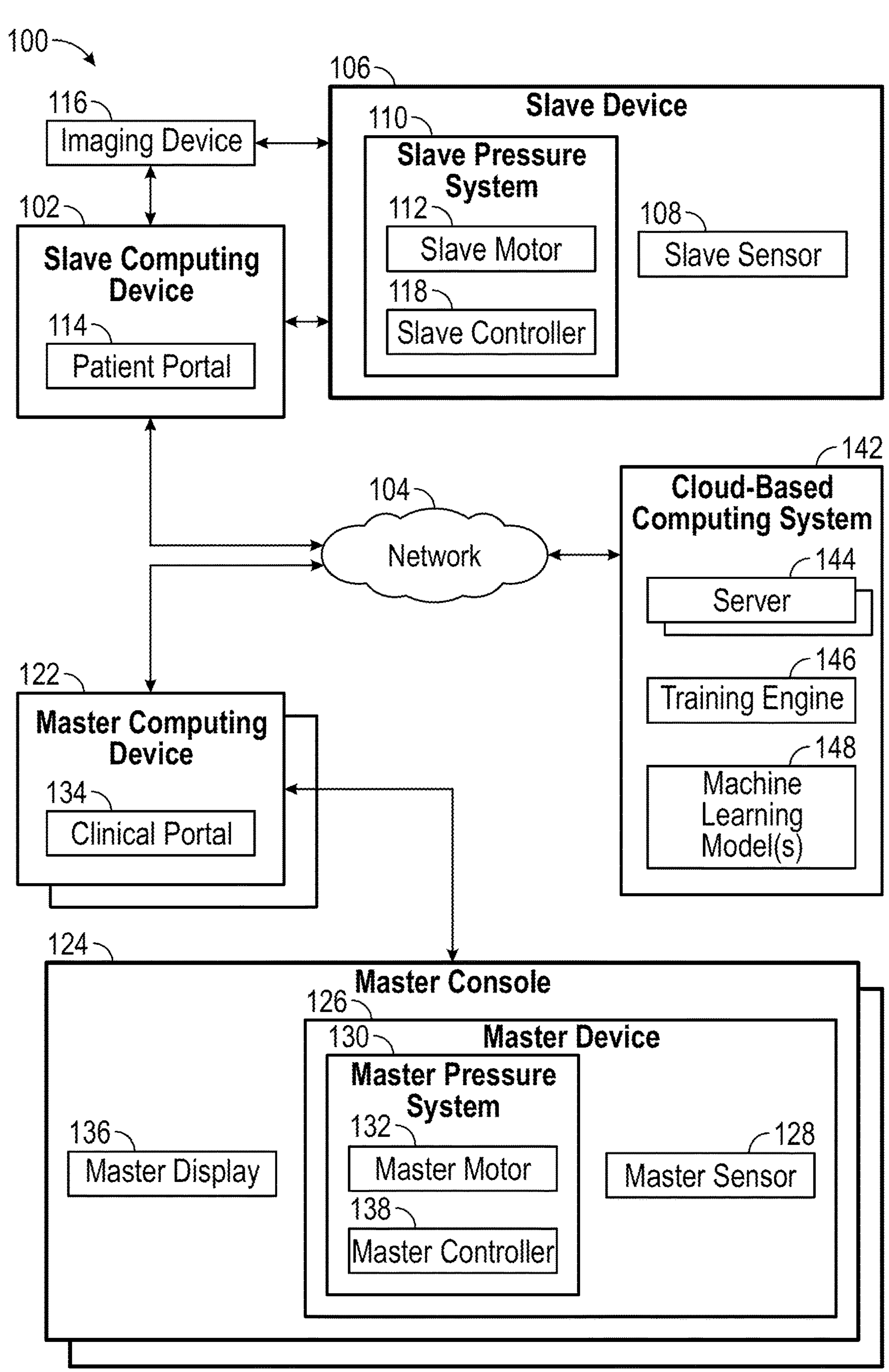
FIG. 1 generally illustrates a high-level component diagram of an illustrative system according to certain aspects of this disclosure.

Various terms are used to refer to particular system components. Different companies may refer to a component by different names—this document does not intend to distinguish between components that differ in name but not function. In the following discussion and in the claims, the terms "including" and "comprising" are used in an open-ended fashion, and thus should be interpreted to mean "including, but not limited to . . . ." Also, the term "couple" or "couples" is intended to mean either an indirect or direct connection. Thus, if a first device couples to a second device, that connection may be through a direct connection or through an indirect connection via other devices and connections.

The terminology used herein is for the purpose of describing particular example embodiments only, and is not intended to be limiting. As used herein, the singular forms "a," "an," and "the" may be intended to include the plural forms as well, unless the context clearly indicates otherwise. The method steps, processes, and operations described herein are not to be construed as necessarily requiring their performance in the particular order discussed or illustrated, unless specifically identified as an order of performance. It is also to be understood that additional or alternative steps may be employed.

The terms first, second, third, etc. may be used herein to describe various elements, components, regions, layers and/or sections; however, these elements, components, regions, layers and/or sections should not be limited by these terms. These terms may be only used to distinguish one element, component, region, layer, or section from another region, layer, or section. Terms such as "first," "second," and other numerical terms, when used herein, do not imply a sequence or order unless clearly indicated by the context. Thus, a first element, component, region, layer, or section discussed below could be termed a second element, component, region, layer, or section without departing from the teachings of the example embodiments. The phrase "at least one of," when used with a list of items, means that different combinations of one or more of the listed items may be used, and only one item in the list may be needed. For example, "at least one of: A, B, and C" includes any of the following combinations: A, B, C, A and B, A and C, B and C, and A and B and C. In another example, the phrase "one or more" when used with a list of items means there may be one item or any suitable number of items exceeding one.

Spatially relative terms, such as "inner," "outer," "beneath," "below," "lower," "above," "upper," "top," "bottom," "inside," "outside," "contained within," "superimposing upon," and the like, may be used herein. These spatially relative terms can be used for ease of description to describe one element's or feature's relationship to another element(s) or feature(s) as illustrated in the figures. The spatially relative terms may also be intended to encompass different orientations of the device in use, or operation, in addition to the orientation depicted in the figures. For example, if the device in the figures is turned over, elements described as "below" or "beneath" other elements or features would then be oriented "above" the other elements or features. Thus, the example term "below" can encompass both an orientation of above and below. The device may be otherwise oriented (rotated 90 degrees or at other orientations) and the spatially relative descriptions used herein interpreted accordingly.

A "treatment plan" may include one or more treatment protocols, and each treatment protocol includes one or more treatment sessions. Each treatment session comprises several session periods, with each session period including a particular exercise for treating the body part of the patient. For example, a treatment plan for post-operative rehabilitation after a knee surgery may include an initial treatment protocol with twice daily stretching sessions for the first 3 days after surgery and a more intensive treatment protocol with active exercise sessions performed 4 times per day starting 4 days after surgery. A treatment plan may also include information pertaining to a medical procedure to perform on the patient, a treatment protocol for the patient using a treatment device, a diet regimen for the patient, a medication regimen for the patient, a sleep regimen for the patient, additional regimens, or some combination thereof.

The terms telemedicine, telehealth, telemed, teletherapeutic, telemedicine, remote medicine, etc. may be used interchangeably herein.

The term "optimal treatment plan" may refer to optimizing a treatment plan based on a certain parameter or factors or combinations of more than one parameter or factor, such as, but not limited to, a measure of benefit which one or more exercise regimens provide to users, one or more probabilities of users complying with one or more exercise regimens, an amount, quality or other measure of sleep associated with the user, information pertaining to a diet of the user, information pertaining to an eating schedule of the user, information pertaining to an age of the user, information pertaining to a sex of the user, information pertaining to a gender of the user, an indication of a mental state of the user, information pertaining to a genetic condition of the user, information pertaining to a disease state of the user, an indication of an energy level of the user, information pertaining to a microbiome from one or more locations on or in the user (e.g., skin, scalp, digestive tract, vascular system, etc.), or some combination thereof.

As used herein, the term healthcare provider may include a medical professional (e.g., such as a doctor, a nurse, a therapist, and the like), an exercise professional (e.g., such as a coach, a trainer, a nutritionist, and the like), or another professional sharing at least one of medical and exercise attributes (e.g., such as an exercise physiologist, a physical therapist, an occupational therapist, and the like). As used herein, and without limiting the foregoing, a "healthcare provider" may be a human being, a robot, a virtual assistant, a virtual assistant in virtual and/or augmented reality, or an artificially intelligent entity, such entity including a software program, integrated software and hardware, or hardware alone.

DETAILED DESCRIPTION

The following discussion is directed to various embodiments of the present disclosure. Although one or more of these embodiments may be preferred, the embodiments disclosed should not be interpreted, or otherwise used, as limiting the scope of the disclosure, including the claims. In addition, one skilled in the art will understand that the following description has broad application, and the discussion of any embodiment is meant only to be exemplary of that embodiment, and not intended to intimate that the scope of the disclosure, including the claims, is limited to that embodiment.

Determining optimal remote examination procedures to create an optimal treatment plan for a patient having certain characteristics (e.g., vital-sign or other measurements; performance; demographic; geographic; psychographic; diagnostic; measurement- or test-based; medically historic; behavioral historic; cognitive; etiologic; cohort-associative; differentially diagnostic; surgical, physically therapeutic, pharmacologic and other treatment(s) recommended; etc.) may be a technically challenging problem. For example, a multitude of information may be considered when determining a treatment plan, which may result in inefficiencies and inaccuracies in the treatment plan selection process. In a rehabilitative setting, some of the multitude of information considered may include characteristics of the patient such as personal information, performance information, and measurement information. The personal information may include, e.g., demographic, psychographic or other information, such as an age, a weight, a gender, a height, a body mass index, a medical condition, a familial medication history, an injury, a medical procedure, a medication prescribed, or some combination thereof. The performance information may include, e.g., an elapsed time of using a treatment device, an amount of force exerted on a portion of the treatment device, a range of motion achieved on the treatment device, a movement speed of a portion of the treatment device, a duration of use of the treatment device, an indication of a plurality of pain levels using the treatment device, or some combination thereof. The measurement information may include, e.g., a vital sign, a respiration rate, a heartrate, a temperature, a blood pressure, a glucose level or other biomarker, or some combination thereof. It may be desirable to process and analyze the characteristics of a multitude of patients, the treatment plans performed for those patients, and the results of the treatment plans for those patients.

Further, another technical problem may involve distally treating, via a computing device during a telemedicine session, a patient from a location different than a location at which the patient is located. An additional technical problem is controlling or enabling, from the different location, the control of a treatment apparatus used by the patient at the patient's location. Oftentimes, when a patient undergoes rehabilitative surgery (e.g., knee surgery), a medical professional may prescribe a treatment apparatus to the patient to use to perform a treatment protocol at their residence or at any mobile location or temporary domicile. A medical professional may refer to a doctor, physician assistant, nurse, chiropractor, dentist, physical therapist, acupuncturist, physical trainer, or the like. A medical professional may refer to any person with a credential, license, degree, or the like in the field of medicine, physical therapy, rehabilitation, or the like.

When the healthcare provider is located in a location different from the patient and the treatment device, it may be technically challenging for the healthcare provider to monitor the patient's actual progress (as opposed to relying on the patient's word about their progress) in using the treatment device, modify the treatment plan according to the patient's progress, adapt the treatment device to the personal characteristics of the patient as the patient performs the treatment plan, and the like. Further, in addition to the information described above, determining optimal examination procedures for a particular ailment (e.g., injury, disease, any applicable medical condition, etc.) may include physically examining the injured body part of a patient. The healthcare provider, such as a physician or a physical therapist, may visually inspect the injured body part (e.g., a knee joint). The inspection may include looking for signs of inflammation or injury (e.g., swelling, redness, and warmth), deformity (e.g., symmetrical joints and abnormal contours and/or appearance), or any other suitable observation. To determine limitations of the injured body part, the healthcare provider may observe the injured body part as the patient attempts to perform normal activity (e.g., bending and extending the knee and gauging any limitations to the range of motion of the injured knee). The healthcare provide may use one or more hands and/or fingers to touch the injured body part. By applying pressure to the injured body part, the healthcare provider can obtain information pertaining to the extent of the injury. For example, the healthcare provider's fingers may palpate the injured body part to determine if there is point tenderness, warmth, weakness, strength, or to make any other suitable observation.

It may be desirable to compare characteristics of the injured body part with characteristics of a corresponding non-injured body part to determine what an optimal treatment plan for the patient may be such that the patient can obtain a desired result. Thus, the healthcare provider may examine a corresponding non-injured body part of the patient. For example, the healthcare provider's fingers may palpate a non-injured body part (e.g., a left knee) to determine a baseline of how the patient's non-injured body part feels and functions. The healthcare provider may use the results of the examination of the non-injured body part to determine the extent of the injury to the corresponding injured body part (e.g., a right knee). Additionally, injured body parts may affect other body parts (e.g., a knee injury may limit the use of the affected leg, leading to atrophy of leg muscles). Thus, the healthcare provider may also examine additional body parts of the patient for evidence of atrophy of or injury to surrounding ligaments, tendons, bones, and muscles, examples of muscles being such as quadriceps, hamstrings, or calf muscle groups of the leg with the knee injury. The healthcare provider may also obtain information as to a pain level that the patient reports or experiences before, during, and/or after the examination.

The healthcare provider can use the information obtained from the examination (e.g., the results of the examination) to determine a proper treatment plan for the patient. If the healthcare provider cannot conduct a physical examination of the one or more body parts of the patient, the healthcare provider may not be able to fully assess the patient's injury and the treatment plan may not be optimal. Accordingly, embodiments of the present disclosure pertain to systems and methods for conducting a remote examination of a patient. The remote examination system provides the healthcare provider with the ability to conduct a remote examination of the patient, not only by communicating with the patient, but by virtually observing and/or feeling the patient's one or more body parts.

In some embodiments, the systems and methods described herein may be configured to use a treatment device configured to be manipulated by an individual while the user performs a treatment plan. The individual may include a user, patient, or other a person using the treatment device to perform various exercises for prehabilitation, rehabilitation, stretch training, and the like. The systems and methods described herein may be configured to use and/or provide a patient interface comprising an output device configured to present telemedicine information associated with a telemedicine session.

In some embodiments, the systems and methods described herein may be configured to receive a treatment plan for a patient; during the telemedicine session, use the treatment plan to generate at least one parameter; and responsive to at least one trigger condition occurring, control at least one operation of the device. Any or all of the methods described may be implemented during a telemedicine session or at any other desired time.

In some embodiments, the treatment devices may be communicatively coupled to a server. Characteristics of the patients, including the treatment data, may be collected before, during, and/or after the patients perform the treatment plans. For example, any or each of the personal information, the performance information, and the measurement information may be collected before, during, and/or after a patient performs the treatment plans. The results (e.g., improved performance or decreased performance) of performing each exercise may be collected from the treatment device throughout the treatment plan and after the treatment plan is performed. The parameters, settings, configurations, etc. (e.g., position of pedal, amount of resistance, etc.) of the treatment device may be collected before, during, and/or after the treatment plan is performed.

Each characteristic of the patient, each result, and each parameter, setting, configuration, etc. may be timestamped and may be correlated with a particular step or set of steps in the treatment plan. Such a technique may enable the determination of which steps in the treatment plan lead to desired results (e.g., improved muscle strength, range of motion, etc.) and which steps lead to diminishing returns (e.g., continuing to exercise after 3 minutes actually delays or harms recovery).

Data may be collected from the treatment devices and/or any suitable computing device (e.g., computing devices where personal information is entered, such as the interface of the computing device described herein, a clinician interface, patient interface, and the like) over time as the patients use the treatment devices to perform the various treatment plans. The data that may be collected may include the characteristics of the patients, the treatment plans performed by the patients, the results of the treatment plans, any of the data described herein, any other suitable data, or a combination thereof.

In some embodiments, the data may be processed to group certain people into cohorts. The people may be grouped by people having certain or selected similar characteristics, treatment plans, and results of performing the treatment plans. For example, athletic people having no medical conditions who perform a treatment plan (e.g., use the treatment device for 30 minutes a day 5 times a week for 3 weeks) and who fully recover may be grouped into a first cohort. Older people who are classified obese and who perform a treatment plan (e.g., use the treatment plan for 10 minutes a day 3 times a week for 4 weeks) and who improve their range of motion by 75 percent may be grouped into a second cohort.

In some embodiments, an artificial intelligence engine may include one or more machine learning models that are trained using the cohorts. In some embodiments, the artificial intelligence engine may be used to identify trends and/or patterns and to define new cohorts based on achieving desired results from the treatment plans and machine learning models associated therewith may be trained to identify such trends and/or patterns and to recommend and rank the desirability of the new cohorts. For example, the one or more machine learning models may be trained to receive an input of characteristics of a new patient and to output a treatment plan for the patient that results in a desired result. The machine learning models may match a pattern between the characteristics of the new patient and at least one patient of the patients included in a particular cohort. When a pattern is matched, the machine learning models may assign the new patient to the particular cohort and select the treatment plan associated with the at least one patient. The artificial intelligence engine may be configured to control, distally and based on the treatment plan, the treatment device while the new patient uses the treatment device to perform the treatment plan.

As may be appreciated, the characteristics of the new patient (e.g., a new user) may change as the new patient uses the treatment device to perform the treatment plan. For example, the performance of the patient may improve quicker than expected for people in the cohort to which the new patient is currently assigned. Accordingly, the machine learning models may be trained to dynamically reassign, based on the changed characteristics, the new patient to a different cohort that includes people having characteristics similar to the now-changed characteristics as the new patient. For example, a clinically obese patient may lose weight and no longer meet the weight criterion for the initial cohort, result in the patient's being reassigned to a different cohort with a different weight criterion.

A different treatment plan may be selected for the new patient, and the treatment device may be controlled, distally (e.g., which may be referred to as remotely) and based on the different treatment plan, while the new patient uses the treatment device to perform the treatment plan. Such techniques may provide the technical solution of distally controlling a treatment device.

Further, the systems and methods described herein may lead to faster recovery times and/or better results for the patients because the treatment plan that most accurately fits their characteristics is selected and implemented, in real-time, at any given moment. "Real-time" may also refer to near real-time, which may be less than 10 seconds or any reasonably proximate difference between two different times. As described herein, the term "results" may refer to medical results or medical outcomes. Results and outcomes may refer to responses to medical actions. The term "medical action(s)" may refer to any suitable action performed by the medical professional, and such action or actions may include diagnoses, prescription of treatment plans, prescription of treatment devices, and the making, composing and/or executing of appointments, telemedicine sessions, prescription of medicines, telephone calls, emails, text messages, and the like.

Depending on what result is desired, the artificial intelligence engine may be trained to output several treatment plans. For example, one result may include recovering to a threshold level (e.g., 75% range of motion) in a fastest amount of time, while another result may include fully recovering (e.g., 100% range of motion) regardless of the amount of time. The data obtained from the patients and sorted into cohorts may indicate that a first treatment plan provides the first result for people with characteristics similar to the patient's, and that a second treatment plan provides the second result for people with characteristics similar to the patient.

Further, the artificial intelligence engine may be trained to output treatment plans that are not optimal i.e., sub-optimal, nonstandard, or otherwise excluded (all referred to, without limitation, as "excluded treatment plans") for the patient. For example, if a patient has high blood pressure, a particular exercise may not be approved or suitable for the patient as it may put the patient at unnecessary risk or even induce a hypertensive crisis and, accordingly, that exercise may be flagged in the excluded treatment plan for the patient. In some embodiments, the artificial intelligence engine may monitor the treatment data received while the patient (e.g., the user) with, for example, high blood pressure, uses the treatment device to perform an appropriate treatment plan and may modify the appropriate treatment plan to include features of an excluded treatment plan that may provide beneficial results for the patient if the treatment data indicates the patient is handling the appropriate treatment plan without aggravating, for example, the high blood pressure condition of the patient. In some embodiments, the artificial intelligence engine may modify the treatment plan if the monitored data shows the plan to be inappropriate or counterproductive for the user.

In some embodiments, the treatment plans and/or excluded treatment plans may be presented, during a telemedicine or telehealth session, to a healthcare provider. The healthcare provider may select a particular treatment plan for the patient to cause that treatment plan to be transmitted to the patient and/or to control, based on the treatment plan, the treatment device. In some embodiments, to facilitate telehealth or telemedicine applications, including remote diagnoses, determination of treatment plans and rehabilitative and/or pharmacologic prescriptions, the artificial intelligence engine may receive and/or operate distally from the patient and the treatment device.

In such cases, the recommended treatment plans and/or excluded treatment plans may be presented simultaneously with a video of the patient in real-time or near real-time during a telemedicine or telehealth session on a user interface of a computing device of a medical professional. The video may also be accompanied by audio, text and other multimedia information and/or other sensorial or perceptive (e.g., tactile, gustatory, haptic, pressure-sensing-based or electromagnetic (e.g., neurostimulation). Real-time may refer to less than or equal to 2 seconds. Near real-time may refer to any interaction of a sufficiently short time to enable two individuals to engage in a dialogue via such user interface, and will generally be less than 10 seconds (or any suitably proximate difference between two different times) but greater than 2 seconds.

Presenting the treatment plans generated by the artificial intelligence engine concurrently with a presentation of the patient video may provide an enhanced user interface because the healthcare provider may continue to visually and/or otherwise communicate with the patient while also reviewing the treatment plans on the same user interface. The enhanced user interface may improve the healthcare provider's experience using the computing device and may encourage the healthcare provider to reuse the user interface. Such a technique may also reduce computing resources (e.g., processing, memory, network) because the healthcare provider does not have to switch to another user interface screen to enter a query for a treatment plan to recommend based on the characteristics of the patient. The artificial intelligence engine may be configured to provide, dynamically on the fly, the treatment plans and excluded treatment plans.

In some embodiments, the treatment device may be adaptive and/or personalized because its properties, configurations, and positions may be adapted to the needs of a particular patient. For example, the pedals may be dynamically adjusted on the fly (e.g., via a telemedicine session or based on programmed configurations in response to certain measurements being detected) to increase or decrease a range of motion to comply with a treatment plan designed for the user. In some embodiments, a healthcare provider may adapt, remotely during a telemedicine session, the treatment device to the needs of the patient by causing a control instruction to be transmitted from a server to treatment device. Such adaptive nature may improve the results of recovery for a patient, furthering the goals of personalized medicine, and enabling personalization of the treatment plan on a per-individual basis.

FIGS. 1-13, discussed below, and the various embodiments used to describe the principles of this disclosure are by way of illustration only and should not be construed in any way to limit the scope of the disclosure.

FIG. 1 illustrates a high-level component diagram of an illustrative remote examination system 100 according to certain embodiments of this disclosure. In some embodiments, the remote examination system 100 may include a slave computing device 102 communicatively coupled to a slave device, such as a treatment device 106. The treatment device can include a slave sensor 108 and a slave pressure system 110. The slave pressure system can include a slave motor 112. The remote examination system may also be communicatively coupled to an imaging device 116. Each of the slave computing device 102, the treatment device 106, and the imaging device 116 may include one or more processing devices, memory devices, and network interface cards. The network interface cards may enable communication via a wireless protocol for transmitting data over short distances, such as Bluetooth, ZigBee, etc. In some embodiments, the slave computing device 102 is communicatively coupled to the treatment device 106 and the imaging device 116 via Bluetooth.

Additionally, the network interface cards may enable communicating data over long distances, and in one example, the slave computing device 102 may communicate with a network 104. The network 104 may be a public network (e.g., connected to the Internet via wired (Ethernet) or wireless (WiFi)), a private network (e.g., a local area network (LAN) or wide area network (WAN)), or a combination thereof. The slave computing device 102 may be communicatively coupled with one or more master computing devices 122 and a cloud-based computing system 142.

The slave computing device 102 may be any suitable computing device, such as a laptop, tablet, smartphone, or computer. The slave computing device 102 may include a display capable of presenting a user interface, such as a patient portal 114. The patient portal 114 may be implemented in computer instructions stored on the one or more memory devices of the slave computing device 102 and executable by the one or more processing devices of the slave computing device 102. The patient portal 114 may present various screens to a patient that enable the patient to view his or her medical records, a treatment plan, or progress during the treatment plan; to initiate a remote examination session; to control parameters of the treatment device 106; to view progress of rehabilitation during the remote examination session; or combination thereof. The slave computing device 102 may also include instructions stored on the one or more memory devices that, when executed by the one or more processing devices of the slave computing device 102, perform operations to control the treatment device 106.

The slave computing device 102 may execute the patient portal 114. The patient portal 114 may be implemented in computer instructions stored on the one or more memory devices of the slave computing device 102 and executable by the one or more processing devices of the slave computing device 102. The patient portal 114 may present various screens to a patient which enable the patient to view a remote examination provided by a healthcare provider, such as a physician or a physical therapist. The patient portal 114 may also provide remote examination information for a patient to view. The examination information can include a summary of the examination and/or results of the examination in real-time or near real-time, such as measured properties (e.g., angles of bend/extension, pressure exerted on the treatment device 106, images of the examined/treated body part, vital signs of the patient, such as heart rate, temperature, etc.) of the patient during the examination. The patient portal 114 may also provide the patient's health information, such as a health history, a treatment plan, and a progress of the patient throughout the treatment plan. So the examination of the patient may begin, the examination information specific to the patient may be transmitted via the network 104 to the cloud-based computing system 142 for storage and/or to the slave computing device 102.

The treatment device 106 may be an examination device for a body part of a patient. As illustrated in FIGS. 2A-D, the treatment device 106 can be configured in alternative arrangements and is not limited to the example embodiments described in this disclosure. Although not illustrated, the treatment device 106 can include a slave motor 112 and a motor controller 118. The treatment device 106 can include a slave pressure system 110. The slave pressure system 110 is any suitable pressure system configured to increase and/or decrease the pressure in the treatment device 106. For example, the slave pressure system 110 can comprise the slave motor 112, the motor controller 118, and a pump. The motor controller 118 can activate the slave motor 112 to cause a pump or any other suitable device to inflate or deflate one or more sections 210 of the treatment device 106. The treatment device 106 can be operatively coupled to one or more slave processing devices. The one or more slave processing devices can be configured to execute instructions in accordance with aspects of this disclosure.

As illustrated in FIG. 2A, the treatment device 106 may comprise a brace 202 (e.g., a knee brace) configured to fit on the patient's body part, such as an arm, a wrist, a neck, a torso, a leg, a knee, an ankle, hips, or any other suitable body part. The brace 202 may include slave sensors 108. The slave sensors 108 can be configured to detect information associated with the patient. For example, the slave sensors 108 can detect a measured level of force exerted from the patient to the treatment device 106, a temperature of the one or more body parts in contact with the patient, a movement of the treatment device 106, any other suitable information, or any combination thereof. The brace 202 may include sections 210. The sections 210 can be formed as one or more chambers. The sections 210 may be configured to be filled with a liquid (e.g., a gel, air, water, etc.). The sections 210 may be configured in one or more shapes, such as, but not limited to rectangles, squares, diamonds circles, trapezoids, any other suitable shape, or combination thereof. The sections 210 may be the same or different sizes. The sections 210 may be positioned throughout the treatment device 106. The sections 210 can be positioned on the brace 202 above a knee portion, below the knee portion, and along the sides of the knee portion. In some embodiments, the brace 202 may include sections 210 positioned adjacent to each other and positioned throughout the brace 202. The sections 210 are not limited to the exemplary illustrations in FIG. 4. The brace 202 may include the one or more materials for the brace 202 and, in some embodiments, straps coupled to the brace 202. The brace 202 be formed from metal, foam, plastic, elastic, or any suitable material or combination of materials. The brace 202 may be formed in any suitable shape, size, or design.

As illustrated in FIG. 2B, the treatment device 106 may comprise a cap 204 that can be configured to fit onto the patient's head. FIG. 2B illustrates exemplary layers of the treatment device 106. The treatment device 106 may include a first layer 212 and a second layer 214. The first layer may be an outer later and the second layer 214 may be an inner layer. The second layer 214 may include the sections 210 and one or more sensors 108. In this example embodiment, the sections 210 are coupled to and/or from portions of the second layer 214. The sections 210 can be configured in a honeycomb pattern. The one or more sensors 108 may be coupled to the first layer 212. The first layer 212 can be coupled to the second layer 214. The first layer 212 can be designed to protect the sections 210 and the sensors 108. The cap 204 may include a strap. The cap 204 and/or the strap be formed from metal, foam, plastic, elastic, or any suitable material or combination of materials. The cap 204 may be formed in any suitable shape, size, or design.

As illustrated in FIG. 2C, the slave may comprise a mat 206. The mat 206 may be configured for a patient to lie or sit down, or to stand upon. The mat 206 may include one or more sensors 108. The mat 206 may include one or more sections 210. The sections 210 in the treatment device 106 can be configured in a square grid pattern. The one or more sensors 108 may be coupled to and/or positioned within the one or more sections 210. The mat 206 can be rectangular, circular, square, or any other suitable configuration. The mat 206 be formed from metal, foam, plastic, elastic, or any suitable material or combination of materials. The mat 206 may include one or more layers, such as a top layer.

As illustrated in FIG. 2D, the slave may comprise a wrap 208. The wrap 208 may be configured to wrap the wrap 208 around one or more portions and/or one or more body parts of the patient. For example, the wrap 208 may be configured to wrap around a person's torso. The wrap 208 may include one or more sensors 108. The wrap 208 may include one or more sections 210. The sections 210 in the treatment device 106 can be configured in a diamond grid pattern. The one or more sensors 108 may be coupled to and/or positioned within the one or more sections 210. The wrap 208 can be rectangular, circular, square, or any other suitable configuration. The wrap 208 may include a strap. The wrap 208 and/or the strap be formed from metal, foam, plastic, elastic, or any suitable material or combination of materials.

The treatment device 106 may include at least one or more motor controllers 118 and one or more motors 112, such as an electric motor. A pump, not illustrated, may be operatively coupled to the motor. The pump may be a hydraulic pump or any other suitable pump. The pump may be configured to increase or decrease pressure within the treatment device 106. The size and speed of the pump may determine the flow rate (i.e., the speed that the load moves) and the load at the slave motor 112 may determine the pressure in one or more sections 210 of the treatment device 106. The pump can be activated to increase or decrease pressure in the one or more sections 210. One or more of the sections 210 may include a sensor 108. The sensor 108 can be a sensor for detecting signals, such as a measured level of force, a temperature, or any other suitable signal. The motor controller 118 may be operatively coupled to the motor 112 and configured to provide commands to the motor 112 to control operation of the motor 112. The motor controller 118 may include any suitable microcontroller including a circuit board having one or more processing devices, one or more memory devices (e.g., read-only memory (ROM) and/or random access memory (RAM)), one or more network interface cards, and/or programmable input/output peripherals. The motor controller 118 may provide control signals or commands to drive the motor 112. The motor 112 may be powered to drive the pump of the treatment device 106. The motor 112 may provide the driving force to the pump to increase or decrease pressure at configurable speeds. Further, the treatment device 106 may include a current shunt to provide resistance to dissipate energy from the motor 112. In some embodiments, the treatment device 106 may comprise a haptic system, a pneumatic system, any other suitable system, or combination thereof. For example, the haptic system can include a virtual touch by applying forces, vibrations, or motions to the patient through the treatment device 106.

The slave computing device 102 may be communicatively connected to the treatment device 106 via a network interface card on the motor controller 118. The slave computing device 102 may transmit commands to the motor controller 118 to control the motor 112. The network interface card of the motor controller 118 may receive the commands and transmit the commands to the motor 112 to drive the motor 112. In this way, the slave computing device 102 is operatively coupled to the motor 112.

The slave computing device 102 and/or the motor controller 118 may be referred to as a control system (e.g., a slave control system) herein. The patient portal 114 may be referred to as a patient user interface of the control system. The control system may control the motor 112 to operate in a number of modes: standby, inflate, and deflate. The standby mode may refer to the motor 112 powering off so it does not provide a driving force to the one or more pumps. For example, if the pump does not receive instructions to inflate or deflate the treatment device 106, the motor 112 may remain turned off. In this mode, the treatment device 106 may not provide additional pressure to the patient's body part(s).

The inflate mode may refer to the motor 112 receiving manipulation instructions comprising measurements of pressure, causing the motor 112 to drive the one or more pumps coupled to the one or more sections of the treatment device 106 to inflate the one or more sections. The manipulation instruction may be configurable by the healthcare provider. For example, as the healthcare provider moves a master device 126, the movement is provided in a manipulation instruction for the motor 112 to drive the pump to inflate one or more sections of the treatment device 106. The manipulation instruction may include a pressure gradient to inflate first and second sections in a right side of a knee brace to first and second measured levels of force and inflate a third section in a left side of the knee brace to a third measured level of force. The first measured level of force correlates with the amount of pressure applied to the master device 126 by the healthcare provider's first finger. The second measured level of force correlates with the amount of pressure applied to the master device 126 by the healthcare provider's second finger. The third measured level of force correlates with the amount of pressure applied to the master device 126 by the healthcare provider's third finger.

The deflation mode may refer to the motor 112 receiving manipulation instructions comprising measurements of pressure, causing the motor 112 to drive the one or more pumps coupled to the one or more sections of the treatment device 106 to deflate the one or more sections. The manipulation instruction may be configurable by the healthcare provider. For example, as the healthcare provider moves the master device 126, the movement is provided in a manipulation instruction for the motor 112 to drive the pump to deflate one or more sections of the treatment device 106. The manipulation instruction may include a pressure gradient to deflate the first and second sections in the right side of the knee brace to fourth and fifth measured levels of force and deflate the third section in the left side of the knee brace to the third measured level of force. The fourth measured level of force correlates with the amount of pressure applied to the master device 126 by the healthcare provider's first finger. The fifth measured level of force correlates with the amount of pressure applied to the master device 126 by the healthcare provider's second finger. The sixth measured level of force correlates with the amount of pressure applied to the master device 126 by the healthcare provider's third finger. In this example, the healthcare provider loosened a grip (e.g., applied less pressure to each of the three fingers) applied to the treatment device 106 virtually via the master device 126.

During one or more of the modes, the one or more slave sensors 108 may measure force (i.e., pressure or weight) exerted by a part of the body of the patient. For example, the each of the one or more sections 310 of the treatment device 106 may contain any suitable sensor (e.g., strain gauge load cell, piezoelectric crystal, hydraulic load cell, etc.) for measuring force exerted on the treatment device 106. Further, the each of the one or more sections 310 of the treatment device 106 may contain any suitable sensor for detecting whether the body part of the patient separates from contact with the treatment device 106. The force detected may be transmitted via the network interface card of the treatment device 106 to the control system (e.g., slave computing device 102 and/or the slave controller 118). As described further below, the control system may modify a parameter of operating the slave motor 112 using the measured force. Further, the control system may perform one or more preventative actions (e.g., locking the slave motor 112 to stop the pump from activating, slowing down the slave motor 112, presenting a notification to the patient such as via the patient portal 114, etc.) when the body part is detected as separated from the treatment device 106, among other things.

In some embodiments, the remote examination system 100 includes the imaging device 116. The imaging device 116 may be configured to capture and/or measure angles of extension and/or bend of body parts and transmit the measured angles to the slave computing device 102 and/or the master computing device 122. The imaging device 116 may be included in an electronic device that includes the one or more processing devices, memory devices, and/or network interface cards. The imaging device 116 may be disposed in a cavity of the treatment device 106 (e.g., in a mechanical brace). The cavity of the mechanical brace may be located near a center of the mechanical brace such that the mechanical brace affords to bend and extend. The mechanical brace may be configured to secure to an upper body part (e.g., leg, arm, etc.) and a lower body part (e.g., leg, arm, etc.) to measure the angles of bend as the body parts are extended away from one another or retracted closer to one another.

The imaging device 116 can be a wearable, such as a wristband 704. The wristband 704 may include a 2-axis accelerometer to track motion in the X, Y, and Z directions, an altimeter for measuring altitude, and/or a gyroscope to measure orientation and rotation. The accelerometer, altimeter, and/or gyroscope may be operatively coupled to a processing device in the wristband 704 and may transmit data to the processing device. The processing device may cause a network interface card to transmit the data to the slave computing device 102 and the slave computing device 102 may use the data representing acceleration, frequency, duration, intensity, and patterns of movement to track measurements taken by the patient over certain time periods (e.g., days, weeks, etc.). Executing a clinical portal 134, the slave computing device 102 may transmit the measurements to the master computing device 122. Additionally, in some embodiments, the processing device of the wristband 704 may determine the measurements taken and transmit the measurements to the slave computing device 102. In some embodiments, the wristband 704 may use photoplethysmography (PPG), which detects an amount of red light or green light on the skin of the wrist, to measure heart rate. For example, blood may absorb green light so that when the heart beats, the blood flow may absorb more green light, thereby enabling the detection of heart rate. The heart rate may be sent to the slave computing device 102 and/or the master computing device 122.

The slave computing device 102 may present the measurements (e.g., measured level of force or temperature) of the body part of the patient taken by the treatment device 106 and/or the heart rate of the patient via a graphical indicator (e.g., a graphical element) on the patient portal 114, as discussed further below. The slave computing device 102 may also use the measurements and/or the heart rate to control a parameter of operating the treatment device 106. For example, if the measured level of force exceeds a target pressure level for an examination session, the slave computing device 102 may control the motor 112 to reduce the pressure being applied to the treatment device 106.

In some embodiments, the remote examination system 100 may include a master computing device 122 communicatively coupled to a master console 124. The master console 124 can include a master device 126. The master device 126 can include a master sensor 128 and a master pressure system 130. The master pressure system can include a master motor 132. The remote examination system may also be communicatively coupled to a master display 136. Each of the master computing device 122, the master device 126, and the master display 136 may include one or more processing devices, memory devices, and network interface cards. The network interface cards may enable communication via a wireless protocol for transmitting data over short distances, such as Bluetooth, ZigBee, Near-Field Communications (NFC), etc. In some embodiments, the master computing device 122 is communicatively coupled to the master device 126 and the master display 136 via Bluetooth.

Additionally, the network interface cards may enable communicating data over long distances, and in one example, the master computing device 122 may communicate with a network 104. The master computing device 122 may be communicatively coupled with the slave computing device 102 and the cloud-based computing system 142.

The master computing device 122 may be any suitable computing device, such as a laptop, tablet, smartphone, or computer. The master computing device 122 may include a display capable of presenting a user interface, such as a clinical portal 134. The clinical portal 134 may be implemented in computer instructions stored on the one or more memory devices of the master computing device 122 and executable by the one or more processing devices of the master computing device 122. The clinical portal 134 may present various screens to a user (e.g., a healthcare provider), the screens configured to enable the user to view a patient's medical records, a treatment plan, or progress during the treatment plan; to initiate a remote examination session; to control parameters of the master device 126; to view progress of rehabilitation during the remote examination session, or combination thereof. The master computing device 122 may also include instructions stored on the one or more memory devices that, when executed by the one or more processing devices of the master computing device 122, perform operations to control the master device 126.

The master computing device 122 may execute the clinical portal 134. The clinical portal 134 may be implemented in computer instructions stored on the one or more memory devices of the master computing device 122 and executable by the one or more processing devices of the master computing device 122. The clinical portal 134 may present various screens to a healthcare provider (e.g., a clinician), the screens configured to enables the clinician to view a remote examination of a patient, such as a patient rehabilitating from a surgery (e.g., knee replacement surgery) or from an injury (e.g., sprained ankle). During a telemedicine session, an augmented image representing one or more body parts of the patient may be presented simultaneously with a video of the patient on the clinical portal 134 in real-time or in near real-time. For example, the clinical portal 134 may, at the same time, present the augmented image 402 of the knee of the patient and portions of the patient's leg extending from the knee and a video of the patient's upper body (e.g., face), so the healthcare provider can engage in more personal communication with the patient (e.g., via a video call). The video may be of the patient's full body, such that, during the telemedicine session, the healthcare provider may view the patient's entire body. The augmented image 402 can be displayed next to the video and/or overlaid onto the respective one or more body parts of the patient. For example, the augmented image 402 may comprise a representation of the treatment device 106 coupled to the patient's knee and leg portions. The clinical portal 134 may display the representation of the treatment device 106 overlaid onto the respective one or more body parts of the patient. Real-time may refer to less than 2 seconds, or any other suitable amount of time. Near real-time may refer to 2 or more seconds. The video may also be accompanied by audio, text, and other multimedia information. The master display 136 may also be configured to present the augmented image and/or the video as described herein.

Presenting the remote examination generated by the artificial intelligence engine concurrently with a presentation of the patient video may provide an enhanced user interface because the healthcare provider, while reviewing the examination on the same user interface, may also continue to visually and/or otherwise communicate with the patient. The enhanced user interface may improve the healthcare provider's experience in using the computing device and may encourage the healthcare provider to reuse the user interface. Such a technique may also reduce computing resources (e.g., processing, memory, network), because the healthcare provider does not have to switch to another user interface screen and, using the characteristics of the patient, enter a query for examination guidelines to recommend. For example, the enhanced user interface may provide the healthcare provider with recommended procedures to conduct during the telemedicine session. The recommended procedures may comprise a guide map, including indicators of locations and measured amounts of pressure to apply on the patient's one or more body parts. The artificial intelligence engine may analyze the examination results (e.g., measured levels of force exerted to and by the patient's one or more body parts, the temperature of the patient, the pain level of the patient, a measured range of motion of the one or more body parts, etc.) and provide, dynamically on the fly, the optimal examination procedures and excluded examination procedures.

The clinical portal 134 may also provide examination information generated during the telemedicine session for the healthcare provider to view. The examination information can include a summary of the examination and/or the results of the examination in real-time or near real-time, such as measured properties of the patient during the examination. Examples of the measured properties may include, but are not limited to, angles of bend/extension, pressure exerted on the master device 126, pressure exerted by the patient on the treatment device 106, images of the examined/treated body part, and vital signs of the patient, such as heart rate and temperature. The clinical portal 134 may also provide the clinician's notes and the patient's health information, such as a health history, a treatment plan, and a progress of the patient throughout the treatment plan. So the healthcare provider may begin the remote examination, the examination information specific to the patient may be transmitted via the network 104 to the cloud-based computing system 142 for storage and/or to the master computing device 122.

In some embodiments, the clinical portal 134 may include a treatment plan that includes one or more examination procedures (e.g., manipulation instructions to manipulate one or more sections 210 of the treatment device 106). For example, a healthcare provider may input, to the clinical portal 134, a treatment plan with pre-determined manipulation instructions for the treatment device 106 to perform during the remote examination. The healthcare provider may input the pre-determined manipulation instructions prior the remote examination. The treatment device 106 can be activated to perform the manipulations in accordance with the pre-determined manipulation instructions. The healthcare provider may observe the remote examination in real-time and make modifications to the pre-determined manipulation instructions during the remote examination. Additionally, the system 100 can store the results of the examination and the healthcare provider can complete the examination using the stored results (e.g., stored slave sensor data) and the master device 126. In other words, the master processing device can use the slave sensor data to manipulate the master device 126. This manipulation of the master device 126 can allow the healthcare provider to virtually feel the patient's one or more body parts and provide the healthcare provider with additional information to determine a personalized treatment plan for the patient.

The master device 126 may be an examination device configured for control by a healthcare provider. The master device 126 may be a joystick, a model treatment device (e.g., a knee brace to fit over a manikin knee), an examination device to fit over a body part of the healthcare provider (e.g., a glove device), any other suitable device, or combination thereof. The joystick may be configured to be used by a healthcare provider to provide manipulation instructions. The joystick may have one or more buttons (e.g., a trigger) to apply more or less pressure to one or more sections of the treatment device 106. The joystick may be configured to control a moveable indicator (e.g., a cursor) displayed at the master display or any other suitable display. The moveable indicator can be moved over an augmented image 400 of the treatment device 106 and/or one or more body parts of the patient. The healthcare provider may be able to provide verbal commands to increase and/or decrease pressure based on where the moveable indicator is positioned relative to the augmented image 400. The joystick may have master sensors 128 within a stick of the joystick. The stick may be configured to provide feedback to the user (e.g., vibrations or pressure exerted by the stick to the user's hand).

The model of the treatment device may be formed similarly to the treatment device 106. For example, if the treatment device 106 is the knee brace 202, the master device can be a model knee brace with similar characteristics of the knee brace 202. The model can be configured for coupling to a manikin or any other suitable device. The model can comprise the master pressure system 130 and master sensors 128 and function as described in this disclosure. The model may be configured for a healthcare provider to manipulate (e.g., touch, move, and/or apply pressure) to one or more sections of the model and to generate master sensor data based on such manipulations. The model can be operatively coupled to the treatment device 106. The master sensor data can be used to inflate and/or deflate one or more corresponding sections of the treatment device 106 (e.g., as the healthcare provider is manipulating the model, the treatment device 106 is being manipulated on the patient). Responsive to receiving the slave sensor data, the master pressure system 130 can active and inflate and/or deflate one or more sections of the model (e.g., the pressure applied to the treatment device 106 by the patient's one or more body parts is similarly applied to the model for the healthcare provider to examine). The healthcare provider can essentially feel, with his or her bare (or appropriately gloved) hands, the patient's one or more body parts (e.g., the knee) while the healthcare provider virtually manipulates the patient body part(s).

In some embodiments, the system 100 may include one or more master computing devices 122 and one or more master consoles 124. For example, a second master console can include a second master device 126 operatively coupled to a second master computing device. The second master device can comprise a second master pressure system 130, and, using the slave force measurements, the one or more processing devices of system 100 can be configured to activate the second master pressure system 130. During and/or after a telemedicine session, one or more healthcare providers can manipulate the treatment device 106 and/or use the slave sensor data to virtually feel the one or more body parts of the patient. For example, a physician and a physical therapist may virtually feel the one or more body parts of the patient at the same time or at different times. The physician may provide the manipulation instructions and the physical therapist may observe (e.g., virtually see and/or feel) how the patient's one or more body parts respond to the manipulations. The physician and the physical therapist may use different examination techniques (e.g., locations of the manipulations and/or measure levels of force applied to the treatment device 106) to obtain information for providing a treatment plan for the patient. Resulting from the physician using the master device 106 and the physical therapist using the second master device, each can provide manipulation instructions to the treatment device 106. The manipulation instructions from the master device 106 and the second master device may be provided at the same time or at a different time (e.g., the physician provides a first manipulation instruction via the master device 126 and the physical therapist provides a second manipulation instruction via the second master device). In another example, the physician may have input a pre-determined manipulation instruction for the remote examination and the physical therapist may use the second master device to adjust the pre-determined manipulation instructions. The physician and the physical therapist may be located remotely from each other (and remotely from the patient) and each can use the system 100 to examine the patient and provide a personalized treatment plan for the patient. The system 100 can allow for collaboration between one or more healthcare providers and provide the healthcare providers with information to make optimal adjustments to the patient's treatment plan.

Figure 3:
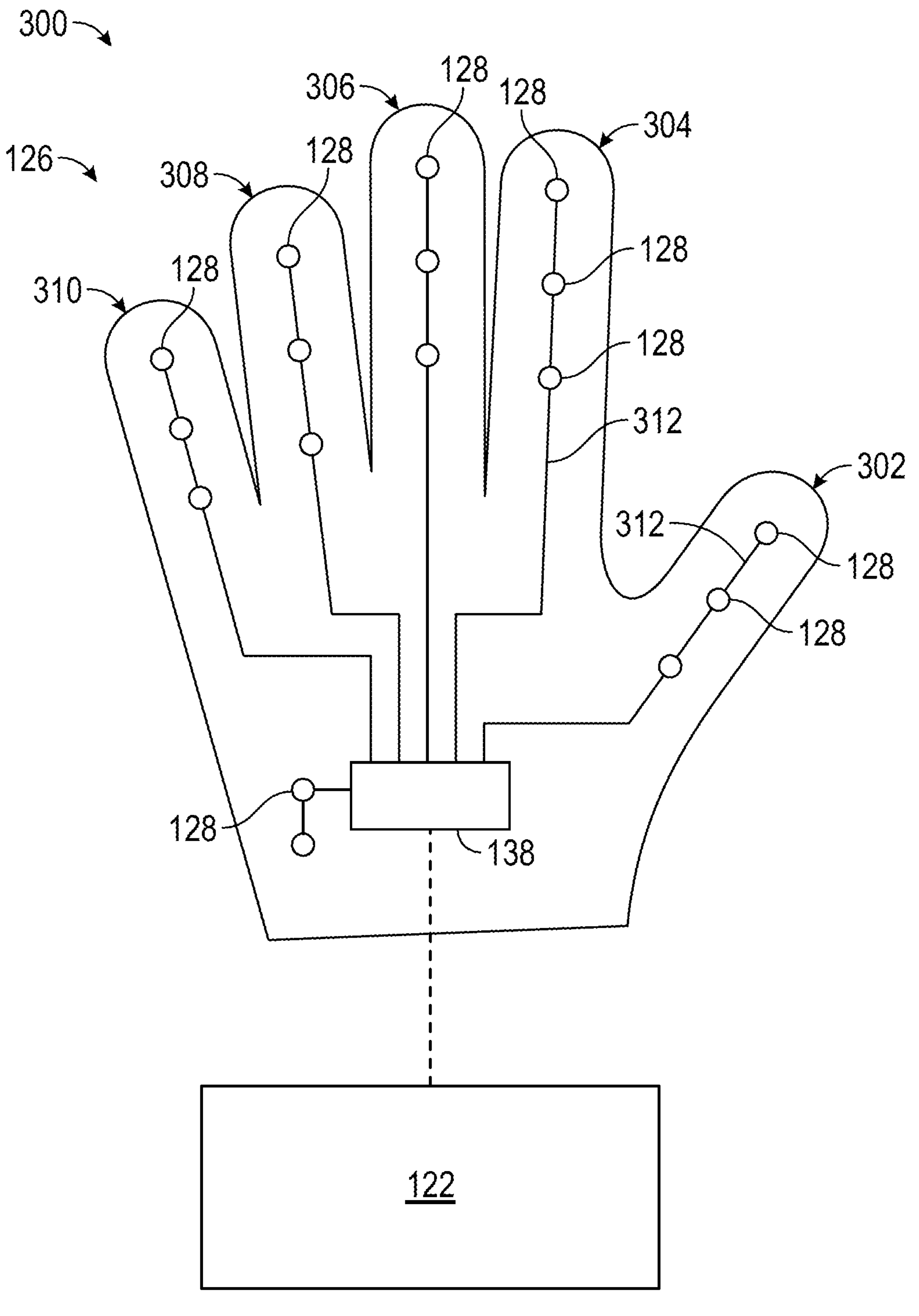
FIG. 3 generally illustrates an example master device according to certain aspects of this disclosure.

As illustrated in FIG. 3, the master device 126 comprises a glove device 300 configured to fit on a healthcare provider's hand. The glove device 300 can include fingers 302. The glove may include one or more sensors (e.g., one or more master sensors 128). The glove device 300 may include the master sensors 128 positioned along the fingers 302, 304, 306, 308, 310 (collectively, fingers 302), throughout the palm of the glove, in any other suitable location, or in any combination thereof. For example, each finger can include a series of master sensors 128 positioned along the fingers 302. Each of the series of master sensors 128 can be operatively coupled to one or more master controllers 138. The master device 126 may include at least one or more master controllers 138 and one or more master motors 132, such as an electric motor (not illustrated).

A pump (not illustrated) may be operatively coupled to the motor. The pump may be configured to increase or decrease pressure within the master device 126. The master device 126 may include one or more sections and the pump can be activated to increase or decrease pressure (e.g., inflating or deflating fluid, such as water, gel, air) in the one or more sections (e.g., one or more fingertips). One or more of the sections may include a master sensor 128. The master sensor 128 can be a sensor for detecting signals, such as pressure, or any other suitable signal. The master controller 138 may be operatively coupled to the master motor 132 and configured to provide commands to the master motor 132 to control operation of the master motor 132. The master controller 138 may include any suitable microcontroller including a circuit board having one or more processing devices, one or more memory devices (e.g., read-only memory (ROM) and/or random access memory (RAM)), one or more network interface cards, and/or programmable input/output peripherals. The master controller 138 may provide control signals or commands to drive the master motor 132. The master motor 132 may be powered to drive the pump of the master device 126. The master motor 132 may provide the driving force to the pump to increase or decrease pressure at configurable speeds. Further, the master device 126 may include a current shunt to provide resistance to dissipate energy from the master motor 132. In some embodiments, the treatment device 106 may comprise a haptic system, a pneumatic system, any other suitable system, or combination thereof. For example, the haptic system can include a virtual touch by applying forces, vibrations, or motions to the healthcare provider through the master device 126.

The master computing device 122 may be communicatively connected to the master device 126 via a network interface card on the master controller 138. The master computing device 122 may transmit commands to the master controller 138 to control the master motor 132. The network interface card of the master controller 138 may receive the commands and transmit the commands to the master controller 138 to drive the master motor 132. In this way, the master computing device 122 is operatively coupled to the master motor 132.

The master computing device 122 and/or the master controller 138 may be referred to as a control system (e.g., a master control system) herein. The clinical portal 134 may be referred to as a clinical user interface of the control system. The master control system may control the master motor 132 to operate in a number of modes, including: standby, inflate, and deflate. The standby mode may refer to the master motor 132 powering off so that it does not provide any driving force to the one or more pumps. For example, when the healthcare provider is not touching an augmented image of the treatment device 106, the pump of the master device 126 may not receive instructions to inflate or deflate one or more sections of the master device 126 and the master motor 132 may remain turned off. In the standby mode, the master device 126 may not apply pressure to the healthcare provider's body part(s) (e.g., to the healthcare provider's finger 304 via the glove device 300) because the healthcare provider is not in virtual contact with the treatment device 106. Furthermore, in standby mode, the master device 126 may not transmit the master sensor data based on manipulations of the master device 126 (e.g., pressure virtually exerted from the healthcare care provider's hand to the master device 126) to the patient via the treatment device 106.

The inflate mode may refer to the master motor 132 receiving slave sensor data comprising measurements of pressure, causing the master motor 132 to drive the one or more pumps coupled to the one or more sections of the master device 126 (e.g., one or more fingers 302, 304, 406, 308, 310) to inflate the one or more sections. The slave sensor data may be provided by the one or more slave sensors 108 of the treatment device 106 via the slave computing device 102. For example, as the healthcare provider manipulates (e.g., moves) the master device 126 to virtually contact one or more body parts of the patient using the treatment device 106 in contact with the patient's one or more body parts, the treatment device 106 is manipulated. The slave sensors 108 are configured to detect the manipulation of the treatment device 106. The detected information may include how the patient's one or more body parts respond to the manipulation. The one or more slave sensors 108 may detect that one area of the patient's body part exerts a first measured level of force and that another area of the patient's body part exerts a second measured level of force (e.g., the one area may be swollen or inconsistent with baseline measurements or expectations as compared to the other area). The master computing device 122 can receive the information from the slave sensor data and instruct the master motor 132 to drive the pump to inflate one or more sections of the master device 126. The level of inflation of the one or more sections of the master device 126 may correlate with one or more measured levels of force detected by the treatment device 106. The slave sensor data may include a pressure gradient. The master computing device 122 may instruct the master pressure system 130 to inflate a first section (e.g., the fingertips of the first finger 302) associated with the first measured level of force exerted from a left side of the knee brace 202. The master computing device 122 may instruct the master pressure system 130 to inflate second and third sections (e.g., the fingertips of second and third fingers 304, 306) associated with second and third measured levels of force exerted from a front side of the knee brace 202. In other words, in response to the master device 126 virtually touching the treatment device 106, the first measured level of force may correlate with the amount of pressure applied to the healthcare provider's first finger through the first finger 302 of the master device 126. Similarly, the second measured level of force may correlate with the amount of measured force applied by the healthcare provider's second finger through the second finger 304 of the master device 126. The third measured level of force may correlate with the amount of measured force applied by the healthcare provider's third finger through the third finger 306 of the master device 126. The glove device 300 can include a fourth finger 308 to provide a fourth measured level of force, a fifth finger 310 to provide a fifth measured level of force, and/or other sections, such as a palm, or any combination thereof configured to provide measured levels of force to the healthcare provider. The sections of the glove device 300 can be inflated or deflated to correlate with the same and/or different levels of measured force exerted on the treatment device 106.

The deflation mode may refer to the master motor 132 receiving slave sensor data comprising measurements of pressure, causing the master motor 132 to drive the one or more pumps coupled to the one or more sections of the master device 126 (e.g., one or more fingers 302) to deflate the one or more sections. The deflation mode of the master pressure system 130 can function similarly as the inflation mode; however, in the deflation mode, the master pressure system 130 deflates, rather than inflates, the one or more sections of the master device 126. For example, the one or more slave sensors 108 may detect that one area of the patient's body part exerts a first measured level of force and that another area of the patient's body part exerts a second measured level of force (e.g., the one area may be less swollen or less inconsistent with baseline measurements or expectations as compared to the other area). The master computing device 122 can receive the information from the slave sensor data and instruct the master motor 132 to drive the pump to deflate one or more sections of the master device 126. The level of deflation of the one or more sections of the master device 126 may correlate with one or more measured levels of force detected by the treatment device 106.

The measured levels of force can be transmitted between the treatment device 106 and the master device 126 in real-time, near real-time, and/or at a later time. Accordingly, the healthcare provider can use the master device 126 to virtually examine the patient's body part by applying the healthcare provider's hand to the master device 126, such that the healthcare provider's hand can, by means of the signals received by the master device 126 from the treatment device 106, virtually feel, palpate or otherwise sense one or more aspects of the patient's body part (e.g., the pressure, etc.). Similarly, the patient can feel the healthcare provider virtually touching his or her body part (e.g., from the pressure exerted by the treatment device 106). During the session, the patient, via the patient portal 114, can communicate to the healthcare provider via the clinical portal 134. For example, during the remote examination, the patient can inform the healthcare provider that the location of the body part that the healthcare provider is virtually touching (e.g., manipulating), is painful. The information can be communicated verbally and/or visually (e.g., input into the patient portal 114 directly by the client and transmitted to the clinical portal 134 and/or the master display 136). The healthcare provider can receive additional information, such as temperature of the patient's body part, vital signs of the patient, any other suitable information, or any combination thereof.

During one or more of the inflation and deflation modes, the one or more master sensors 128 may measure force (i.e., pressure) exerted by the healthcare provider via the master device 126. For example, one or more sections of the master device 126 may contain any suitable sensor (e.g., strain gauge load cell, piezoelectric crystal, hydraulic load cell, etc.) for measuring force exerted on the master device 126. Further, each section 310 of the master device 126 may contain any suitable sensor for detecting whether the body part of the healthcare provider separates from contact with the master device 126. The measured level(s) of force detected may be transmitted via the network interface card of the master device 126 to the control system (e.g., master computing device 122 and/or the master controller 138). As described further below, using the measured level(s) of force, the control system may modify a parameter of operating the master motor 132. Further, the control system may perform one or more preventative actions (e.g., locking the master motor 132 to stop the pump from activating, slowing down the master motor 132, or presenting a notification to the healthcare provider (such as via the clinical portal 134, etc.)) when the body part is detected as being separated from the master device 126, among other things.

In some embodiments, the remote examination system 100 includes the master display 136. The master console 124 and/or the clinical portal 134 may comprise the master display 136. The master display 136 may be configured to display the treatment device 106 and/or one or more body parts of a patient. For example, the slave computing device 102 may be operatively coupled to an imaging device 116 (e.g., a camera or any other suitable audiovisual device) and/or other sensorial or perceptive (e.g., tactile, gustatory, haptic, pressure-sensing-based or electromagnetic (e.g., neurostimulation) communication devices. Any reference herein to any particular sensorial modality shall be understood to include and to disclose by implication a different one or more sensory modalities. The slave computing device 102 can transmit, via the network 104, real images and/or a real live-streaming video of the treatment device 106 and/or the patient, to the master display 136. The real images and/or real video may include angles of extension and/or bend of body parts of the patient, or any other suitable characteristics of the patient. The treatment device 106 may be operatively coupled to a medical device, such as a goniometer 702. The goniometer 702 may detect angles of extension and/or bend of body parts of the patient and transmit the measured angles to the slave computing device 102 and/or the treatment device 106. The slave computing device 102 can transmit the measured angles to the master computing device 122, to the master display 136, or any other suitable device. The master display 136 can display the measured angles in numerical format, as an overlay image on the image of the treatment device 106 and/or the patient's one or more body parts, any other suitable format, or combination thereof. For example, as illustrated in FIG. 4A, body parts (e.g., a leg and a knee) are extended at a first angle. In FIG. 4B, the body parts are illustrated as being extended at a second angle. The master display 136 may be included in an electronic device that includes the one or more processing devices, memory devices, and/or network interface cards.

Depending on what result is desired, the master computing device 122 and/or a training engine 146 may be trained to output a guide map. The guide map may be overlaid on the augmented image 400. The guide map may include one or more indicators. To guide the master device 126, the indicators can be positioned over one or more sections 310 of the augmented image 400 of the treatment device 106. For example, the augmented image 402 may include a first indicator (e.g., dotted lines in the shape of a fingertip) positioned over a top portion of patient's knee and a second indicator positioned over a left side of the patient's knee. The first indicator is a guide for the healthcare provider to place the first finger 302 on the first indicator and the second finger 304 on the second indicator. The guide map may comprise a pressure gradient map. The pressure gradient map can include the current measured levels of force at the location of the indicator and/or a desired measured level of force at the location of the indicator. For example, the first indicator may comprise a first color, a first size, or any other suitable characteristic to indicate a first measured level of force. The second indicator may comprise a second color, a second size, or any other suitable characteristic to indicate a second measured level of force. When the master device 126 reaches the desired measured levels of force, an alert may be provided. The alert may be a visual, audio and/or another alert. For example, the alert may comprise the indicator changing colors when the measured level of force is provided. The guide map may include one or more configurations using characteristics of the injury, the patient, the treatment plan, the recovery results, the examination results, any other suitable factors, or combination thereof. One or more configurations may be displayed during the remote examination portion of a telemedicine session.

The master computing device 122 and/or the training engine 146 may include one or more thresholds, such as pressure thresholds. The one or more pressure thresholds may be based on characteristics of the injury, the patient, the treatment plan, the recovery results, the examination results, the pain level, any other suitable factors, or combination thereof. For example, one pressure threshold pertaining to the pain level of the patient may include a pressure threshold level for the slave pressure system 110 not to inflate a particular section 210 more than a first measured level of force. As the pain level of the patient decreases, the pressure threshold may change such that a second measured level of force may be applied to that particular section 210. In this case, the patient's decreased pain level may, for more optimal examination results (e.g., the second measured level of force is greater than the first measured level of force), allow for the healthcare provider to increase the measured amount of pressure applied to the patient's body part. Similarly, the master computing device 122 and/or the training engine 146 may be configured to adjust any predetermined manipulation instructions. In this way, the manipulation instructions can be adapted to the specific patient.

In other embodiments, the master display 136 can display an augmented image (e.g., exemplary augmented images 400 illustrated in FIG. 4), an augmented live-streaming video, a holographic image, any other suitable transmission, or any combination thereof of the treatment device 106 and/or one or more body parts of the patient. For example, the master display 136 may project an augmented image 402 representing the treatment device 106 (e.g., a knee brace 202). The augmented image 402 can include a representation 410 of the knee brace 202. The augmented image 402 can include a representation 412 of one or more body parts of a patient. Using the master device 126, the healthcare provider can place a hand on the image and manipulate the image (e.g., apply pressure virtually to one or more sections of the patient's knee via the treatment device 106. The one or more processing devices may cause a network interface card to transmit the data to the master computing device 122 and the master computing device 122 may use the data representing pressure, temperature, and patterns of movement to track measurements taken by the patient's recovery over certain time periods (e.g., days, weeks, etc.). In FIG. 4, the augmented images 400 are two dimensional, but the augmented images 400 may be transmitted as three-dimensional images or as any other suitable image dimensionality.

The master display 136 can be configured to display information obtained from a wearable, such as the wristband 704. The information may include motion measurements of the treatment device 106 in the X, Y, and Z directions, altitude measurements, orientation measurements, rotation measurements, any other suitable measurements, or combination thereof. The wristband 704 may be operatively coupled to an accelerometer, an altimeter, and/or a gyroscope. The accelerometer, the altimeter, and/or the gyroscope may be operatively coupled to a processing device in the wristband 704 and may transmit data to the one or more processing devices. The one or more processing devices may cause a network interface card to transmit the data to the master computing device 122 and the master computing device 122 may use the data representing acceleration, frequency, duration, intensity, and patterns of movement to track measurements taken by the patient over certain time periods (e.g., days, weeks, etc.). Executing the clinical portal 134, the master computing device 122 may transmit the measurements to the master display 136. Additionally, in some embodiments, the processing device of the wristband 704 may determine the measurements taken and transmit the measurements to the slave computing device 102. The measurements may be displayed on the patient portal 114. In some embodiments, the wristband 704 may measure heart rate by using photoplethysmography (PPG), which detects an amount of red light or green light on the skin of the wrist. For example, blood may absorb green light so when the heart beats, the blood volume flow may absorb more green light, thereby enabling heart rate detection. In some embodiments, the wristband 704 may be configured to detect temperature of the patient. The heart rate, temperature, any other suitable measurement, or any combination thereof may be sent to the master computing device 122.

The master computing device 122 may present the measurements (e.g., pressure or temperature) of the body part of the patient taken by the treatment device 106 and/or the heart rate of the patient via a graphical indicator (e.g., a graphical element) on the clinical portal 134. The measurements may be presented as a gradient map, such as a pressure gradient map or a temperature gradient map. The map may be overlaid over the image of the treatment device 106 and/or the image of the patient's body part. For example, FIG. 4C illustrates an exemplary augmented image 406 displaying a pressure gradient 414 over the image of the patient's body parts 412 (e.g., feet). FIG. 4D illustrates an exemplary augmented image 408 displaying a temperature gradient 416 over the image of the patient's body parts 412 (e.g., feet).

Referring back to FIG. 1, the remote examination system 100 may include a cloud-based computing system 142. In some embodiments, the cloud-based computing system 142 may include one or more servers 144 that form a distributed computing architecture. Each of the servers 144 may include one or more processing devices, memory devices, data storage devices, and/or network interface cards. The servers 144 may be in communication with one another via any suitable communication protocol. The servers 144 may store profiles for each of the users (e.g., patients) configured to use the treatment device 106. The profiles may include information about the users such as a treatment plan, the affected body part, any procedure the user had had performed on the affected body part, health, age, race, measured data from the imaging device 116, slave sensor data, measured data from the wristband 704, measured data from the goniometer 702, user input received at the patient portal 114 during the telemedicine session, a level of discomfort the user experienced before and after the remote examination, before and after remote examination images of the affected body part(s), and so forth.

In some embodiments, the cloud-based computing system 142 may include a training engine 146 capable of generating one or more machine learning models 148. The machine learning models 148 may be trained to generate treatment plans, procedures for the remote examination, or any other suitable medical procedure for the patient in response to receiving various inputs (e.g., a procedure via a remote examination performed on the patient, an affected body part the procedure was performed on, other health characteristics (age, race, fitness level, etc.)). The one or more machine learning models 148 may be generated by the training engine 146 and may be implemented in computer instructions executable by one or more processing devices of the training engine 146 and/or the servers 144.

To generate the one or more machine learning models 148, the training engine 146 may train the one or more machine learning models 148. The training engine 146 may use a base data set of patient characteristics, results of remote examination(s), treatment plans followed by the patient, and results of the treatment plan followed by the patients. The results may include information indicating whether the remote examination led to an identification of the affected body part and whether the identification led to a partial recovery of the affected body part or lack of recovery of the affected body part. The results may include information indicating the measured levels of force applied to the one or more sections of the treatment device 106.

The training engine 146 may be a rackmount server, a router computer, a personal computer, an Internet of Things (IoT) device, a portable digital assistant, a smartphone, a laptop computer, a tablet computer, a camera, a video camera, a netbook, a desktop computer, a media center, any other desired computing device, or any combination of the above. The training engine 146 may be cloud-based or a real-time software platform, and it may include privacy software or protocols, and/or security software or protocols.

The one or more machine learning models 148 may also be trained to translate characteristics of patients received in real-time (e.g., from an electronic medical records (EMR) system, from the slave sensor data, etc.). The one or more machine learning models 148 may refer to model artifacts that are created by the training engine 146 using training data that includes training inputs and corresponding target outputs. The training engine 146 may find patterns in the training data that map the training input to the target output, and generate the machine learning models 148 that capture these patterns. Although depicted separately from the slave computing device 102, in some embodiments, the training engine 146 and/or the machine learning models 148 may reside on the slave computing device 102 and/or the master computing device 122.

Different machine learning models 148 may be trained to recommend different optimal examination procedures for different desired results. For example, one machine learning model may be trained to recommend optimal pressure maps for most effective examination of a patient, while another machine learning model may be trained to recommend optimal pressure maps using the current pain level and/or pain level tolerance of a patient.

The machine learning models 148 may include one or more of a neural network, such as an image classifier, recurrent neural network, convolutional network, generative adversarial network, a fully connected neural network, or some combination thereof, for example. In some embodiments, the machine learning models 148 may be composed of a single level of linear or non-linear operations or may include multiple levels of non-linear operations. For example, the machine learning model may include numerous layers and/or hidden layers that perform calculations (e.g., dot products) using various neurons.

FIGS. 1-4 are not intended to be limiting: the remote examination system 100 may include more or fewer components than those illustrated in FIGS. 1-4.

Figure 5:
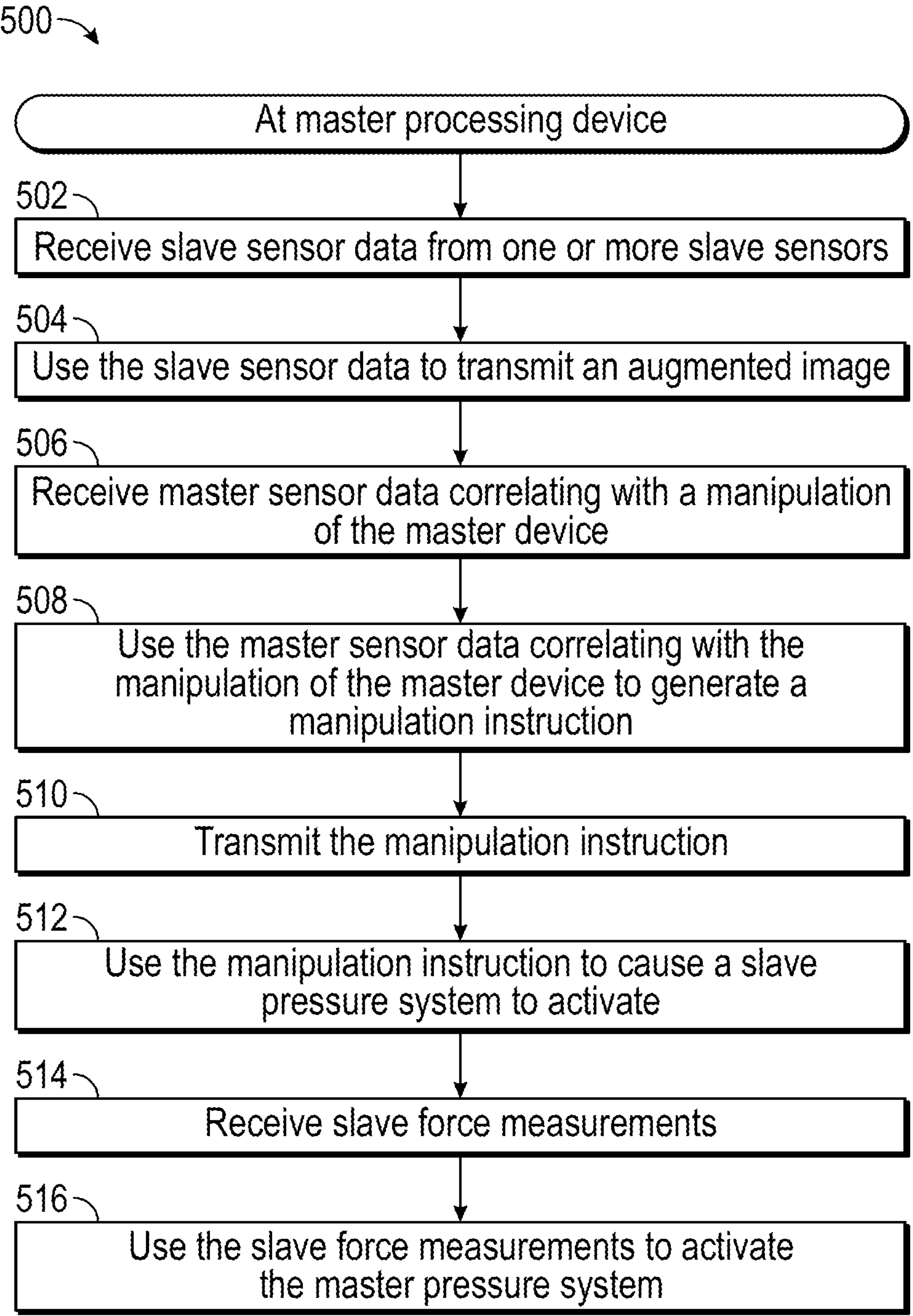
FIG. 5 generally illustrates an example method of operating a remote examination system according to certain aspects of this disclosure.

FIG. 5 illustrates a computer-implemented method 500 for remote examination. The method 500 may be performed by the remote examination system 100, such as at a master processing device. The processing device is described in more detail in FIG. 6. The steps of the method 500 may be stored in a non-transient computer-readable storage medium.

At step 502, the method 500 includes the master processing device receiving slave sensor data from one or more slave sensors 108. The master processing device may receive, via the network 104, the slave sensor data from a slave processing device.

At step 504, the master processing device can transmit an augmented image 400. The augmented image 400 may be based on the slave sensor data.

At step 506, the master processing device receives master sensor data associated with a manipulation of the master device 126. For example, the master sensor data may include a measured level of force that the user, such as a healthcare provider, applied to the master device 126.

At step 508, the master processing device can generate a manipulation instruction. The manipulation instruction is based on the master sensor data associated with the manipulation of the master device 126.

At step 510, the master processing device transmits the manipulation instruction. The master processing device may transmit, via the network 104, the manipulation instruction to the slave computing device 102.

At step 512, the master processing device causes the slave pressure system to activate. Using the manipulation instruction, the slave computing device 102 can cause the treatment device 106 to activate the slave pressure system 110. For example, responsive to the manipulation instruction (e.g., to increase and/or decrease one or more measured levels of force in one or more sections of the treatment device), the slave pressure system 110 can cause the slave controller 118 to activate the slave motor 112 to inflate and/or deflate the one or more sections 210 to one or more measured levels of force.

At step 514, the master processing device receives slave force measurements. The slave force measurements can include one or more measurements associated with one or more measured levels of force that the patient's body is applying to the treatment device 106.

At step 516, the master processing device uses the pressure slave measurements to activate the master pressure system 130. For example, the master pressure system 130 can cause the master device 126 to inflate and/or deflate one or more sections 310 of the master device 126 such that the measured levels of force of the one or more sections 310 directly correlate with the one or more measured levels of force that the patient's body is applying to the one or more sections 210 of the treatment device 106.

Figure 6:
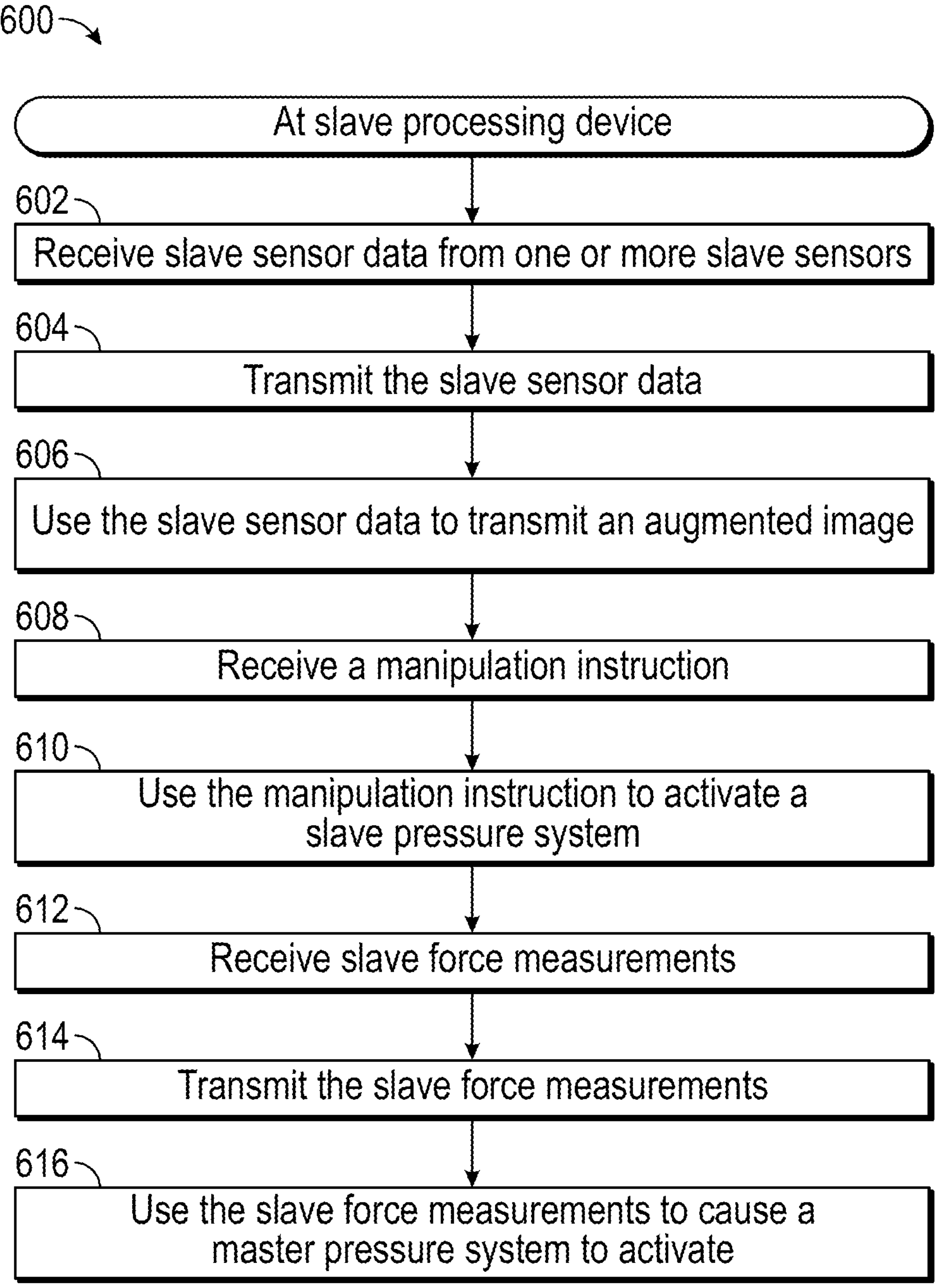
FIG. 6 generally illustrates an example method of operating a remote examination system according to certain aspects of this disclosure.

FIG. 6 illustrates a computer-implemented method 600 for remote examination. The method 600 may be performed by the remote examination system 100, such as at a slave processing device. The processing device is described in more detail in FIG. 6. The steps of the method 600 may be stored in a non-transient computer-readable storage medium.

At step 602, the method 600 includes the slave processing device receiving slave sensor data from one or more slave sensors 108. The one or more slave sensors 108 may include one or more measured levels of force that the patient's body is applying to the treatment device 106.

At step 604, the slave processing device transmits the slave sensor data. The slave processing device may transmit, via the network 104, the slave sensor data to the master computing device 122.

At step 606, the slave processing device may transmit an augmented image 400. The augmented image 400 is based on the slave sensor data. For example, the augmented image 400 may include a representation of the treatment device 106, one or more body parts of the patient, measured levels of force, measured levels of temperature, any other suitable information, or combination thereof.

At step 608, the slave processing device receives a manipulation instruction. The manipulation instruction can be generated based on the master sensor data.

At step 610, using the manipulation instruction, the slave processing device activates the slave pressure system 110. For example, the manipulation instruction may cause the slave pressure system 110 to inflate and/or deflate one or more sections 210 of the treatment device 106 to correlate with one or more levels of force applied to one or more sections 310 of the master device 126.

At step 612, the slave processing device receives slave force measurements. The slave force measurements can include one or more measured levels of force exerted by the patient's body to the treatment device 106.

At step 614, the slave processing device transmits the slave force measurements, such as to the master processing device.

At step 616, using the slave force measurements, the slave processing device causes a master pressure system 130 to activate. For example, the master pressure system 130 can cause the master device 126 to inflate and/or deflate one or more sections 310 of the master device 126 such that the measured levels of force of the one or more sections 310 correlate with the one or more measured levels of force that the patient's body is applying to the one or more sections 210 of the treatment device 106.

FIGS. 5-6 are not intended to be limiting: the methods 500, 600 can include more or fewer steps and/or processes than those illustrated in FIGS. 5-6. Further, the order of the steps of the methods 500, 600 is not intended to be limiting; the steps can be arranged in any suitable order. Any or all of the steps of methods 500,600 may be implemented during a telemedicine session or at any other desired time.

Figure 7:
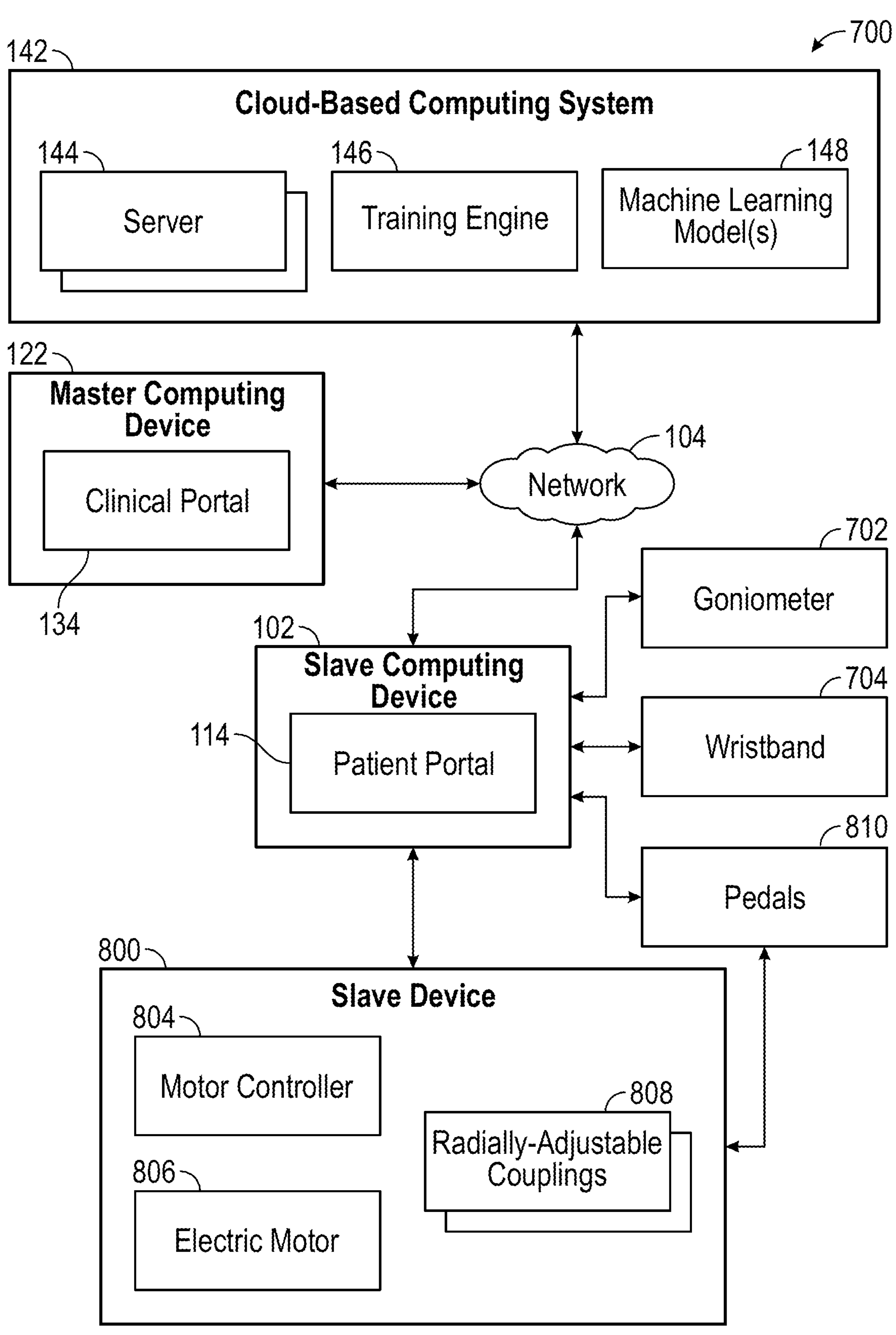
FIG. 7 generally illustrates a high-level component diagram of an illustrative system for a remote adjustment of a device according to certain aspects of this disclosure.

FIG. 7 illustrates a high-level component diagram of an illustrative architecture of system 700 for enabling remote adjustment of a device, such as during a telemedicine session, according to certain aspects of this disclosure. The system 700 may include one or more components of FIG. 1 that have been described above. Any component or combination of the components illustrated in the system 700 may be included in and/or used in connection with the examination system 100. The system 100 and/or the system 700 is not limited to use in the medical field.

In some embodiments, the system 700 may include a slave computing device 102 communicatively coupled to a treatment device 800, such as an electromechanical device 802, a goniometer 702, a wristband 810, and/or pedals 810 of the electromechanical device 802. Each of the computing device 102, the electromechanical device 802, the goniometer 702, the wristband 810, and the pedals 810 may include one or more processing devices, memory devices, and network interface cards. The network interface cards may enable communication via a wireless protocol for transmitting data over short distances, such as Bluetooth, ZigBee, etc. In some embodiments, the computing device 102 is communicatively coupled to the electromechanical device 802, goniometer 702, the wristband 810, and/or the pedals 810 via Bluetooth.

The patient portal 114 may present various screens to a user that enable the user to view a treatment plan, initiate a pedaling session of the treatment plan, control parameters of the electromechanical device 802, view progress of rehabilitation during the pedaling session, and so forth as described in more detail below. The computing device 102 may also include instructions stored on the one or more memory devices that, when executed by the one or more processing devices of the computing device 102, perform operations to control the electromechanical device 802.

The clinical portal 134 may present various screens to a healthcare provider, such as a physician that enable the physician to create a treatment plan for a patient, view progress of the user throughout the treatment plan, view measured properties (e.g., angles of bend/extension, force exerted on pedals 810, heart rate, steps taken, images of the affected body part) of the user during sessions of the treatment plan, view properties (e.g., modes completed, revolutions per minute, etc.) of the electromechanical device 802 during sessions of the treatment plan. The treatment plan specific to a patient may be transmitted via the network 104 to the cloud-based computing system 142 for storage and/or to the computing device 102 so the patient may begin the treatment plan. The healthcare provider can adjust the treatment plan during a session of the treatment plan in real-time or near real-time. For example, the healthcare provider may be monitoring the patient while the patient is using the electromechanical device 802 and, by using the measured properties, the healthcare provider may adjust the treatment plan and transmit the adjusted treatment plan to control at least one operation of the electromechanical device 802. The treatment plan and/or an adjusted treatment plan can include parameters for operation of the electromechanical device 802. If the patient is operating the electromechanical device 802 such that the operations are not within the parameters, a trigger condition may occur, and may be detected or enabled to be detected. In any of the forgoing cases, the one or more processors can control at least one operation of the electromechanical device 102. The automated control can function as a safety feature for the patient as the control mitigates the patient's risk of further injury.

The electromechanical device 802 may be an adjustable pedaling device for exercising, strengthening, and rehabilitating arms and/or legs of a user. The electromechanical device 802 may include at least one or more motor controllers 804, one or more electric motors 806, and one or more radially-adjustable couplings 808. Two pedals 810 may be coupled to two radially-adjustable couplings 808 via left and right pedal assemblies that each include respective stepper motors. The motor controller 804 may be operatively coupled to the electric motor 806 and configured to provide commands to the electric motor 806 to control operation of the electric motor 806. The motor controller 804 may include any suitable microcontroller including a circuit board having one or more processing devices, one or more memory devices (e.g., read-only memory (ROM) and/or random access memory (RAM)), one or more network interface cards, and/or programmable input/output peripherals. The motor controller 804 may provide control signals or commands to drive the electric motor 806. The electric motor 806 may be powered to drive one or more radially-adjustable couplings 808 of the electromechanical device 802 in a rotational manner. The electric motor 806 may provide the driving force to rotate the radially-adjustable couplings 808 at configurable speeds. The couplings 808 are radially-adjustable in that a pedal 810 attached to the coupling 808 may be adjusted to a number of positions on the coupling 808 in a radial fashion. Further, the electromechanical device 802 may include current shunt to provide resistance to dissipate energy from the electric motor 806. As such, the electric motor 806 may be configured to provide resistance to rotation of the radially-adjustable couplings 808.

The computing device 102 may be communicatively connected to the electromechanical device 802 via the network interface card on the motor controller 804. The computing device 102 may transmit commands to the motor controller 804 to control the electric motor 806. The network interface card of the motor controller 804 may receive the commands and transmit the commands to the electric motor 806 to drive the electric motor 806. In this way, the computing device 102 is operatively coupled to the electric motor 806.

The computing device 102 and/or the motor controller 804 may be referred to as a control system herein. The patient portal 114 may be referred to as a user interface of the control system herein. The control system may control the electric motor 806 to operate in a number of modes: passive, active-assisted, resistive, and active. The passive mode may refer to the electric motor 806 independently driving the one or more radially-adjustable couplings 808 rotationally coupled to the one or more pedals 810. In the passive mode, the electric motor 806 may be the only source of driving force on the radially-adjustable couplings. That is, the user may engage the pedals 810 with their hands or their feet and the electric motor 806 may rotate the radially-adjustable couplings 808 for the user. This may enable moving the affected body part and stretching the affected body part without the user exerting excessive force.

The active-assisted mode may refer to the electric motor 806 receiving measurements of revolutions per minute of the one or more radially-adjustable couplings 808, and causing the electric motor 806 to drive the one or more radially-adjustable couplings 808 rotationally coupled to the one or more pedals 810 when the measured revolutions per minute satisfy a parameter (e.g., a threshold condition). The threshold condition may be configurable by the user and/or the physician. The electric motor 806 may be powered off while the user provides the driving force to the radially-adjustable couplings 808 as long as the revolutions per minute are above a revolutions per minute threshold and the threshold condition is not satisfied. When the revolutions per minute are less than the revolutions per minute threshold then the threshold condition is satisfied and the electric motor 806 may be controlled to drive the radially-adjustable couplings 808 to maintain the revolutions per minute threshold.

The resistive mode may refer to the electric motor 806 providing resistance to rotation of the one or more radially-adjustable couplings 808 coupled to the one or more pedals 810. The resistive mode may increase the strength of the body part being rehabilitated by causing the muscle to exert force to move the pedals against the resistance provided by the electric motor 806.

The active mode may refer to the electric motor 806 powering off to provide no driving force assistance to the radially-adjustable couplings 808. Instead, in this mode, the user provides the sole driving force of the radially-adjustable couplings using their hands or feet, for example.

During one or more of the modes, each of the pedals 810 may measure force exerted by a part of the body of the user on the pedal 810. For example, the pedals 810 may each contain any suitable sensor (e.g., strain gauge load cell, piezoelectric crystal, hydraulic load cell, etc.) for measuring force exerted on the pedal 810. Further, the pedals 810 may each contain any suitable sensor for detecting whether the body part of the user separates from contact with the pedals 810. In some embodiments, the measured force may be used to detect whether the body part has separated from the pedals 810. The force detected may be transmitted via the network interface card of the pedal 810 to the control system (e.g., computing device 102 and/or motor controller 804). As described further below, the control system may modify a parameter of operating the electric motor 806 based on the measured force. Further, the control system may perform one or more preventative actions (e.g., locking the electric motor 120 to stop the radially-adjustable couplings 808 from moving, slowing down the electric motor 806, presenting a notification to the user, etc.) when the body part is detected as separated from the pedals 810, among other things.

The goniometer 702 may be configured to measure angles of extension and/or bend of body parts and transmit the measured angles to the computing device 102 and/or the computing device 134. The goniometer 702 may be included in an electronic device that includes the one or more processing devices, memory devices, and/or network interface cards. The goniometer 702 may be disposed in a cavity of a mechanical brace. The cavity of the mechanical brace may be located near a center of the mechanical brace where the mechanical brace affords to bend and extend. The mechanical brace may be configured to secure to an upper body part (e.g., arm, etc.) and a lower body part (e.g., leg, etc.) to measure the angles of bend as the body parts are extended away from one another or retracted closer to one another.

The wristband 810 may include a 3-axis accelerometer to track motion in the X, Y, and Z directions, an altimeter for measuring altitude, and/or a gyroscope to measure orientation and rotation. The accelerometer, altimeter, and/or gyroscope may be operatively coupled to a processing device in the wristband 810 and may transmit data to the processing device. The processing device may cause a network interface card to transmit the data to the computing device 102 and the computing device 102 may use the data representing acceleration, frequency, duration, intensity, and patterns of movement to track steps taken by the user over certain time periods (e.g., days, weeks, etc.). The computing device 102 may transmit the steps to the master computing device 134 executing a clinical portal 134. Additionally, in some embodiments, the processing device of the wristband 810 may determine the steps taken and transmit the steps to the computing device 102. In some embodiments, the wristband 810 may use photoplethysmography (PPG) to measure heart rate that detects an amount of red light or green light on the skin of the wrist. For example, blood may absorb green light so when the heart beats, the blood flow may absorb more green light, thereby enabling detecting heart rate. The heart rate may be sent to the computing device 102 and/or the computing device 134.

The computing device 102 may present the steps taken by the user and/or the heart rate via respective graphical element on the patient portal 114, as discussed further below. The computing device may also use the steps taken and/or the heart rate to control a parameter of operating the electromechanical device 802. For example, if the heart rate exceeds a target heart rate for a pedaling session, the computing device 102 may control the electric motor 806 to reduce resistance being applied to rotation of the radially-adjustable couplings 808. In another example, if the steps taken are below a step threshold for a day, the treatment plan may increase the amount of time for one or more modes in which the user is to operate the electromechanical device 802 to ensure the affected body part is getting sufficient movement.

In some embodiments, the cloud-based computing system 142 may include one or more servers 144 that form a distributed computing architecture. Each of the servers 144 may include one or more processing devices, memory devices, data storage, and/or network interface cards. The servers 144 may be in communication with one another via any suitable communication protocol. The servers 144 may store profiles for each of the users that use the electromechanical device 802. The profiles may include information about the users such as a treatment plan, the affected body part, any procedure the user had performed on the affected body part, health, age, race, measured data from the goniometer 702, measured data from the wristband 810, measured data from the pedals 810, user input received at the patient portal 114 during operation of any of the modes of the treatment plan, a level of discomfort, comfort, or general patient satisfaction that the user experiences before and after any of the modes, before and after session images of the affected body part, and so forth.

In some embodiments the cloud-based computing system 142 may include a training engine 130 that is capable of generating one or more machine learning models 132. The one or more machine learning models 132 may be generated by the training engine 130 and may be implemented in computer instructions that are executable by one or more processing device of the training engine 130 and/or the servers 144. To generate the one or more machine learning models 132, the training engine 130 may train the one or more machine learning models 132. The training engine 130 may use a base data set of patient characteristics, treatment plans followed by the patient, and results of the treatment plan followed by the patients. The results may include information indicating whether the treatment plan led to full recovery of the affected body part, partial recovery of the affected body part, or lack of recovery of the affected body part. The one or more machine learning models 132 may refer to model artifacts that are created by the training engine 130 using training data that includes training inputs and corresponding target outputs. The training engine 130 may find patterns in the training data that map the training input to the target output, and generate the machine learning models 132 that capture these patterns. Although depicted separately from the computing device 102, in some embodiments, the training engine 130 and/or the machine learning models 132 may reside on the computing device 102 and/or the computing device 134.

Figure 8:
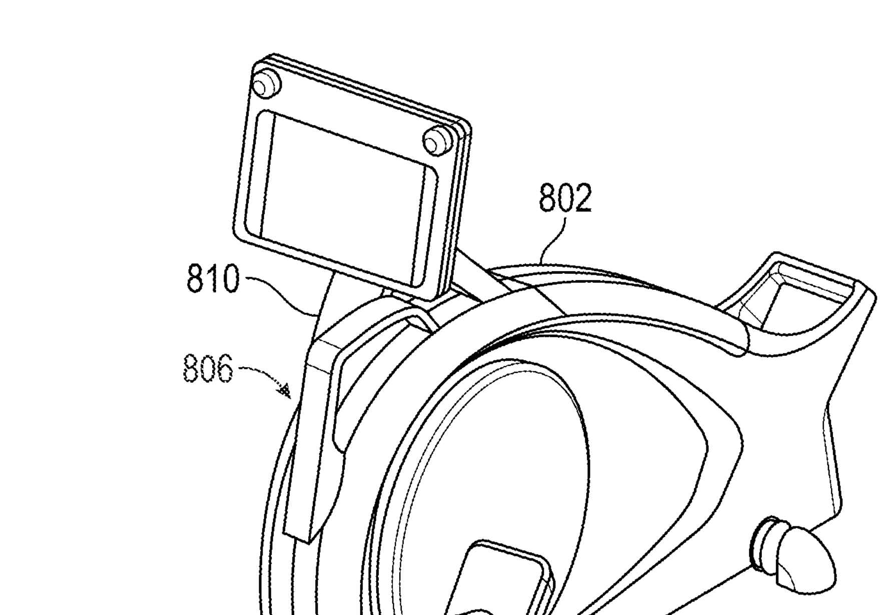
FIG. 8 generally illustrates a perspective view of an example of the device according to certain aspects of this disclosure.
Figure 11:
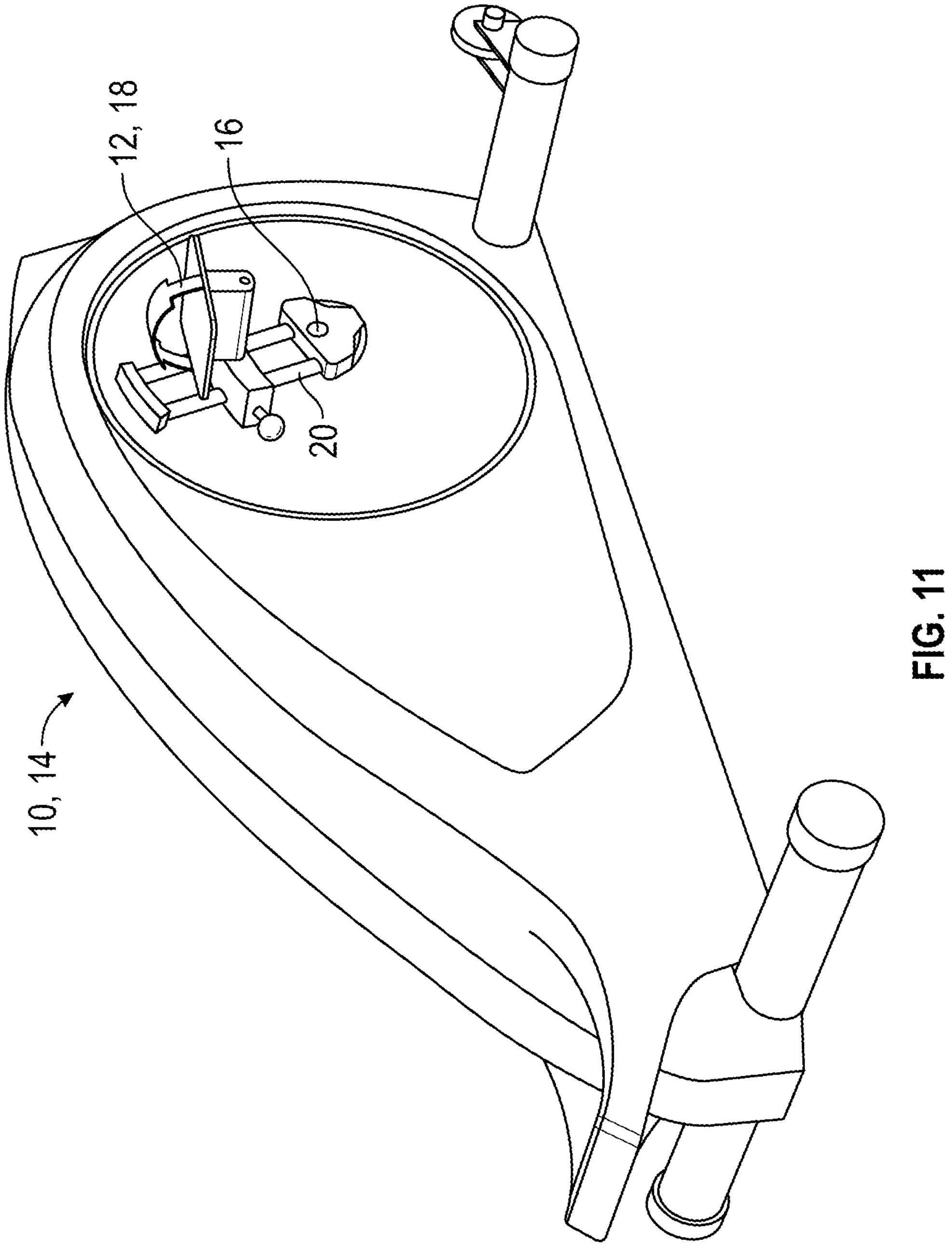
FIG. 11 generally illustrates a perspective view of an embodiment of the device, such as a treatment device according to certain aspects of this disclosure.
Figure 12:
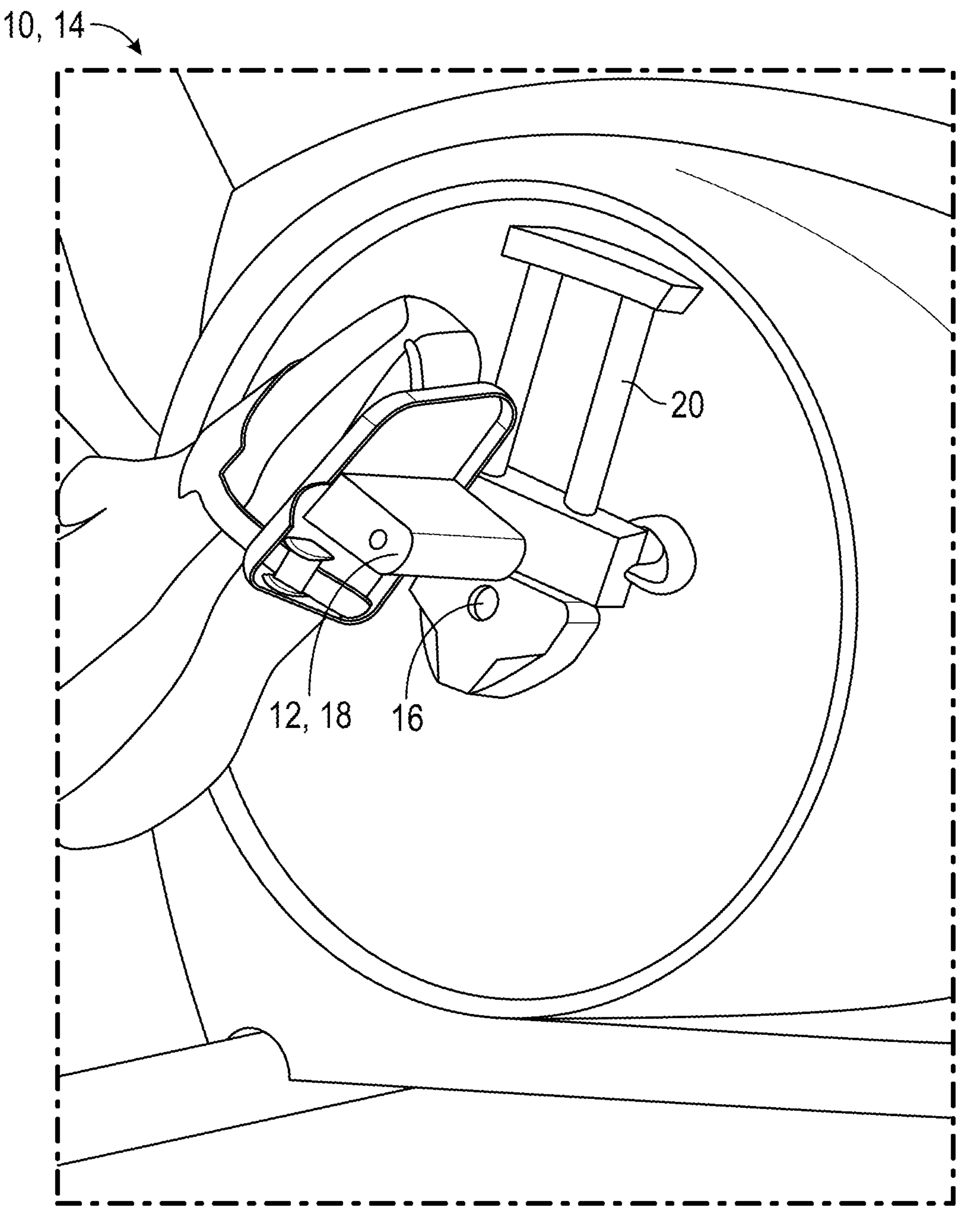
FIG. 12 generally illustrates a perspective view of a pedal of the treatment device of FIG. 11 according to certain aspects of this disclosure.

As illustrated in FIGS. 8 and 11-12, the treatment device 106 may comprise an electromechanical device, such as a physical therapy device. FIG. 8 illustrates a perspective view of an example of a treatment device 800 according to certain aspects of this disclosure. Specifically, the treatment device 800 illustrated is an electromechanical device 802, such as an exercise and rehabilitation device (e.g., a physical therapy device or the like). The electromechanical device 802 is shown having pedal 810 on opposite sides that are adjustably positionable relative to one another on respective radially-adjustable couplings 808. The depicted electromechanical device 802 is configured as a small and portable unit so that it is easily transported to different locations at which rehabilitation or treatment is to be provided, such as at patients' homes, alternative care facilities, or the like. The patient may sit in a chair proximate the electromechanical device 802 to engage the electromechanical device 802 with the patient's feet, for example. The electromechanical device 802 includes a rotary device such as radially-adjustable couplings 808 or flywheel or the like rotatably mounted such as by a central hub to a frame or other support. The pedals 810 are configured for interacting with a patient to be rehabilitated and may be configured for use with lower body extremities such as the feet, legs, or upper body extremities, such as the hands, arms, and the like. For example, the pedal 810 may be a bicycle pedal of the type having a foot support rotatably mounted onto an axle with bearings. The axle may or may not have exposed end threads for engaging a mount on the radially-adjustable coupling 808 to locate the pedal on the radially-adjustable coupling 808. The radially-adjustable coupling 808 may include an actuator configured to radially adjust the location of the pedal to various positions on the radially-adjustable coupling 808.

Alternatively, the radially-adjustable coupling 808 may be configured to have both pedals 810 on opposite sides of a single coupling 808. In some embodiments, as depicted, a pair of radially-adjustable couplings 808 may be spaced apart from one another but interconnected to the electric motor 806. In the depicted example, the computing device 102 may be mounted on the frame of the electromechanical device 802 and may be detachable and held by the user while the user operates the electromechanical device 802. The computing device 102 may present the patient portal 114 and control the operation of the electric motor 806, as described herein.

In some embodiments, as described in U.S. Pat. No. 10,173,094 (U.S. application Ser. No. 15/700,293), which is incorporated by reference herein in its entirety for all purposes, the treatment device 106 may take the form of a traditional exercise/rehabilitation device which is more or less non-portable and remains in a fixed location, such as a rehabilitation clinic or medical practice. The treatment device 106 may include a seat and is less portable than the treatment device 106 shown in FIG. 8. FIG. 8 is not intended to be limiting: the treatment device 800 may include more or fewer components than those illustrated in FIG. 8.

FIGS. 11-12 generally illustrate an embodiment of a treatment device, such as a treatment device 10. More specifically, FIG. 11 generally illustrates a treatment device 10 in the form of an electromechanical device, such as a stationary cycling machine 14, which may be called a stationary bike, for short. The stationary cycling machine 14 includes a set of pedals 12 each attached to a pedal arm 20 for rotation about an axle 16. In some embodiments, and as generally illustrated in FIG. 11, the pedals 12 are movable on the pedal arm 20 in order to adjust a range of motion used by the patient in pedaling. For example, the pedals being located inwardly toward the axle 16 corresponds to a smaller range of motion than when the pedals are located outwardly away from the axle 16. A pressure sensor 18 is attached to or embedded within one of the pedals 12 for measuring an amount of force applied by the patient on the pedal 102. The pressure sensor 18 may communicate wirelessly to the treatment device 10 and/or to the patient interface 26. FIGS. 11-12 are not intended to be limiting: the treatment device 10 may include more or fewer components than those illustrated in FIGS. 11-12.

Figure 13:
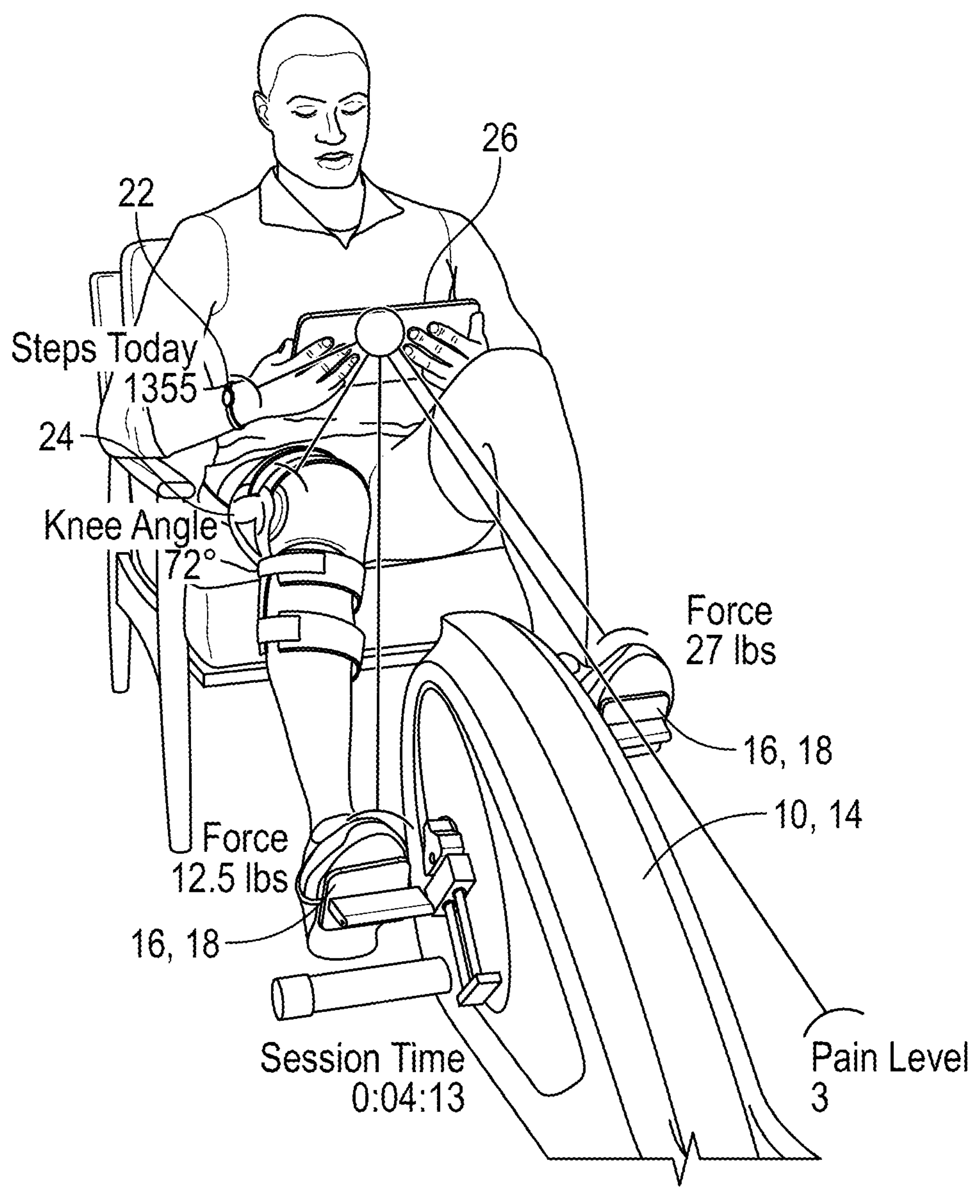
FIG. 13 generally illustrates a perspective view of a person using the treatment device of FIG. 11 according to certain aspects of this disclosure.

FIG. 13 generally illustrates a person (a patient) using the treatment device of FIG. 11, wherein sensors and various data parameters are connected to a patient interface 26. The example patient interface 26 is a tablet computer or smartphone, or a phablet, such as an iPad, an iPhone, an Android device, or a Windows device such as a Surface tablet, any of which may be held manually by the patient. In some other embodiments, the patient interface 26 may be embedded within or attached to the treatment device 10. FIG. 13 generally illustrates the patient wearing the ambulation sensor 22 on his wrist, with a note showing "STEPS TODAY 1355", indicating that the ambulation sensor 22 has recorded and transmitted that step count to the patient interface 26. FIG. 13 also generally illustrates the patient wearing the goniometer 24 on his right knee, with a note showing "KNEE ANGLE 72°", indicating that the goniometer 24 is measuring and transmitting that knee angle to the patient interface 26. FIG. 13 generally illustrates a right side of one of the pedals 12 with a pressure sensor 18 showing "FORCE 12.5 lbs.", indicating that the right pedal pressure sensor 18 is measuring and transmitting that force measurement to the patient interface 26. FIG. 13 also generally illustrates a left side of one of the pedals 12 with a pressure sensor 18 showing "FORCE 27 lbs.", indicating that the left pedal pressure sensor 18 is measuring and transmitting that force measurement to the patient interface 26. FIG. 13 also generally illustrates other patient data, such as an indicator of "SESSION TIME 0:04:13", indicating that the patient has been using the treatment device 10 for 4 minutes and 13 seconds. This session time may be determined by the patient interface 26 based on information received from the treatment device 10. FIG. 13 also generally illustrates an indicator showing "PAIN LEVEL 3". Such a pain level may be obtained from the patient in response to a solicitation, such as a question, presented upon the patient interface 26.

Figure 9:
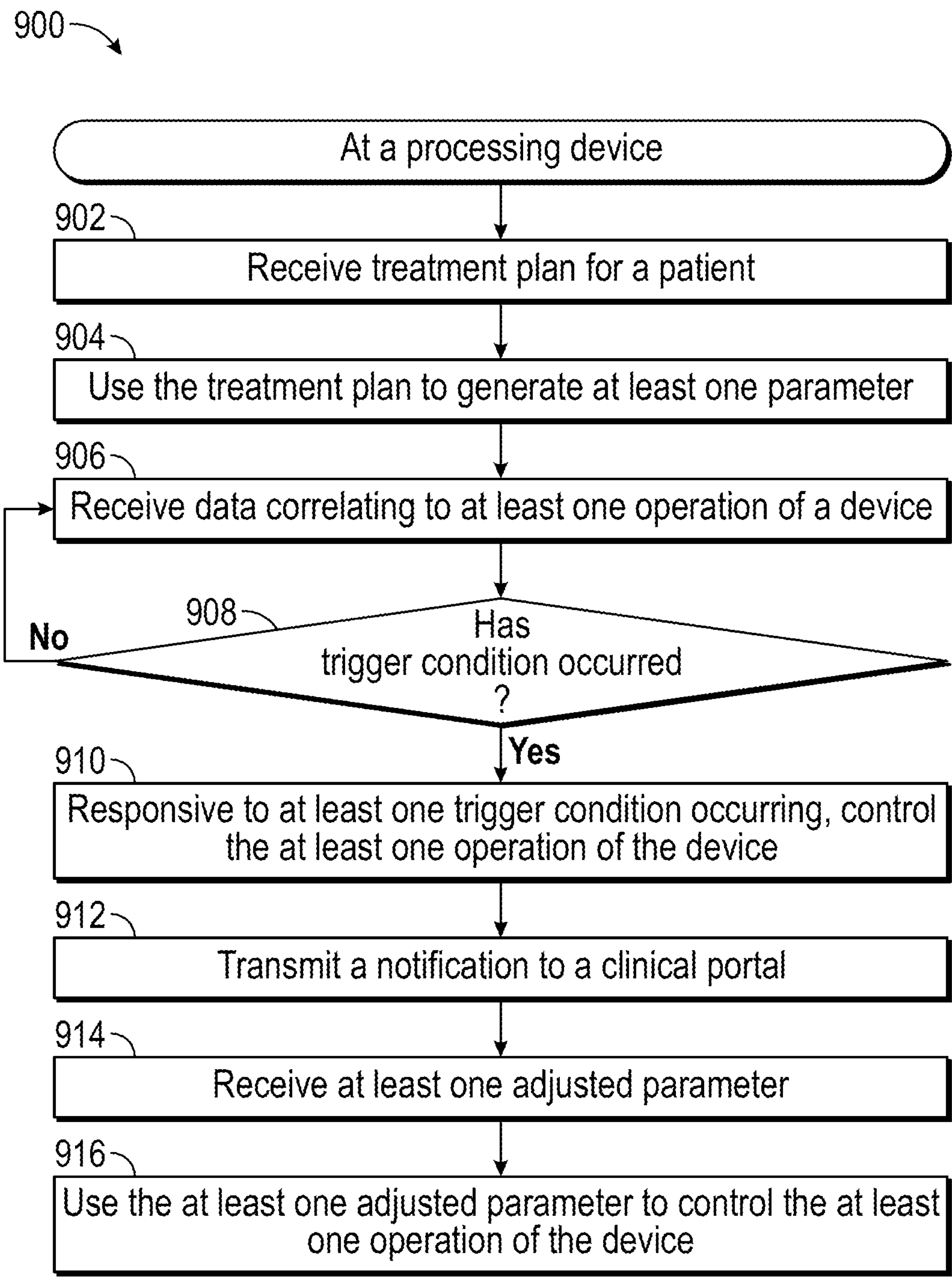
FIG. 9 generally illustrates an example method of enabling a remote adjustment of a device according to certain aspects of this disclosure.

FIG. 9 illustrates a computer-implemented method 900 for enabling a remote adjustment of a device. The device may be a treatment device, such as the treatment device 800, the device 10, or any other desired device. The device may comprise at least one of a physical therapy device (e.g., the rehabilitation device 802), a brace (e.g., the brace 202), a cap (e.g., the cap 204), a mat (e.g., the mat 206), a wrap (e.g., the wrap 208), a treatment device (e.g., the treatment device 10, the treatment device 106, the stationary cycling machine 14, or the like), any other suitable device, or combination thereof. The device may be configured to be manipulated by a user while the user performs a treatment plan. The method 900 may be performed at a processing device operatively coupled to the remote examination system 100, the system 800, or any combination thereof. For example, the method may be performed using a patient interface comprising an output device configured to present telemedicine information associated with a telemedicine session. The steps of the method 900 may be stored in a non-transient computer-readable storage medium.

A healthcare provider can use information obtained from an examination of a patient to determine a proper treatment plan for the patient. Using the systems 100, 800, the healthcare provider can conduct a remote physical examination of the one or more body parts of the patient and/or view results of an exercise, rehabilitation, or other session to provide a treatment plan for the patient. For example, the healthcare provider can conduct the remote physical examination during a telemedicine session.

At step 902, the method 900 includes receiving a treatment plan for a patient. The treatment plan can be received from a clinical portal 134. For example, the healthcare provider may input a treatment plan into the clinical portal 134, which in turn can transmit the treatment plan to the slave computing device 102 and the treatment device 106, 800. For example, the transmission of the treatment plan can be transmitted during a telemedicine session or at another desired time.

At step 904, the method 900 includes using the treatment plan to generate at least one parameter. The at least one parameter may be generated during a telemedicine session or at another desired time. The treatment plan may include a plan to treat a patient (e.g., prehabilitation, rehabilitation, or the like). The plan may include patient information (e.g., patient health history, characteristics of an injury, etc.), one or more types of exercises, a schedule of when and for how long to perform the exercises, at least one threshold that the patient should meet and/or not exceed, any other suitable information, or combination thereof. The processing device can use the information in the treatment plan to generate the at least one parameter. For example, the at least one parameter may be a measurable threshold or threshold ranges of data to be detected by the sensor(s) relating to the patient (e.g., pain level, vital signs, etc.) or to the operation of the treatment device 106, 800 (e.g., volume of sections 210, revolutions per minute, angle of the pedals 810, etc.). The at least one parameter can be at least one of a force parameter, a resistance parameter, a range of motion parameter, a temperature parameter, a pain level parameter, an exercise session parameter, a vital sign parameter, a time parameter, any other suitable parameter, or combination thereof. In one example, the force parameter may be based on characteristics of the injury, the patient, the treatment plan, the recovery results, the examination results, the pain level, any other suitable factors, or combination thereof. The force parameter may pertain to the pain level of the patient and include a measured level of force for the patient to exert on the pedals 810. The resistance parameter may be a parameter pertaining to a measured amount of resistance that the motor 806 applies to the pedals 810 during a cycling session. The range of motion parameter may be a parameter pertaining to a measured range of motion of a patient's body part (e.g., a knee). The temperature parameter may be a parameter pertaining to a measured temperature of the patient or the patient's body part. The pain level parameter may be a parameter pertaining to a level of pain that the patient reports or experiences before, during, or after the patient uses the treatment device 800. The exercise session parameter may be a parameter pertaining to a type of exercise, a number of steps that the patient has taken during the day and/or during an exercise session, or any other suitable exercise information. The exercise session can include a session for any purpose, including rehabilitation, prehabilitation, exercise, strength training, endurance training, any other type of exercise, or combination thereof. The vital sign parameter may be a parameter pertaining to a measurement of the patient's heart rate, pulse rate, blood pressure, respiration rate, or any other vital sign. The time parameter may be a parameter pertaining to an amount of time (e.g., minutes) for which the patient should engage in an exercise session, an amount of time (e.g., hours) between exercise sessions, any other suitable time measurements, or combination thereof.

At step 906, the method 900 includes receiving data correlating with at least one operation of the device. The data may be received during a telemedicine session or at another desired time. The device may comprise one or more sensors for detecting data correlating with the at least one operation. Examples of the measured properties may include, but are not limited to, angles of bend/extension, pressure exerted on the device, the speed of rotating the device (e.g., pedaling speed), the amount of resistance (e.g., pedal resistance), the distance the patient has traveled (e.g., cycled, walked, etc.), the number of steps the patient has taken, images of the examined/treated body part, and vital signs of the patient, such as heart rate and temperature. The data can be received from the one or more sensors in real-time or near real-time.

At step 908, the method 900 includes determining if a trigger condition has occurred. The trigger may be determined during a telemedicine session or at another desired time. A trigger condition is a condition that occurs when at least one of the data, the at least one parameter, a patient input, any other suitable information, or combination thereof is outside of the at least one parameter. Patient input may include a pain level, a pain tolerance, a weight, or any other suitable information from the patient. In one embodiment, the processing device may use the measured heart rate to determine if the heart rate is outside of the vital sign parameter (e.g., above and/or below a heart rate threshold). In another example, the processing device may use the counted number of steps taken to determine if the number of steps taken is outside of the exercise session parameter (e.g., above and/or below a step threshold). If one or more measurements are outside of the respective parameters (e.g., if the patient's heart rate is above the heart rate threshold, if the number of steps the patient has taken during the day is below the step threshold), a trigger condition has occurred. Patient input may be received during a telemedicine session or at another desired time.

At step 910, responsive to at least one trigger condition occurring, the method 900 proceeds with controlling at least one operation of the device. The processing device may control the operation of the device (e.g., the treatment device 106, 800). The processing device may control the operation of the device during a telemedicine session or at another desired time. The controlling of the at least one operation of the device can include causing the device to modify at least one of a volume, a pressure, a resistance, an angle, a speed, an angular or rotational velocity, and a time period. The modification may include not just a value but also a constraint, limitation, maximum, minimum, etc. For example, if the heart rate of the patient exceeds a vital sign parameter for a pedaling session, the computing device 102 may control the electric motor 806 to reduce the resistance being applied to the rotation of the radially-adjustable couplings 808. The motor controller 804 may be operatively coupled to the electric motor 806 and configured to provide commands to the electric motor 806 to control operation of the electric motor 806. In another example, if a volume of a section 210 of the treatment device 106 exceeds the volume parameter, the processing device may control the treatment device 106 to deflate the section 210 to a volume within the volume parameter. In this example, if the measured level of volume exceeds the volume parameter, the excess pressure that the treatment device 106 may be exerting on the patient may cause the patient pain or discomfort, and thus, the processing device is configured to adjust the volume (e.g., decrease the volume) to decrease the pressure exerted on the patient.

At step 912, the method 900 proceeds with transmitting a notification to a clinical portal. The notification may be transmitted during a telemedicine session or at another desired time. The notification may include results of an exercise session, the patient's recovery results, the vital sign(s), the pain level, input from the patient, any other suitable information, or combination thereof. The notification can be transmitted to the clinical portal 134 in real-time, in near real-time, before or after an exercise session, at any other suitable time, or combination thereof. The notification can assist the healthcare provider in assessing the patient's treatment plan and making any adjustments to the treatment plan that may optimize the patient's treatment (i.e., to decrease the patient's recovery time; to increase the patient's strength, range of motion, and flexibility, etc.).

At step 914, the method 900 proceeds with receiving at least one adjusted parameter. The parameter may be received during a telemedicine session or at another desired time. The healthcare provider may input the at least one adjusted parameter to the clinical portal 134 for transmitting to the patient portal 114, the treatment device 106, 800, the slave computing device 102, or any combination thereof. For example, while using the rehabilitation device 802 over the course of a few days, if the patient is not within the time parameter (e.g., not exercising for a long enough period of time) and if the patient's pain level exceeds a pain level parameter, the healthcare provider may adjust the time parameter (e.g., to decrease the amount of time for the exercise) and adjust the force parameter (e.g., to increase the level of motor assistance for a cycling exercise). Such adjustments may result in improved patient compliance with the treatment plan and decrease the patient's recovery time. The at least one adjusted parameter can be received in real-time, in near real-time, prior to an exercise session, at any other suitable time, or any combination thereof. For example, the healthcare provider may be remotely reviewing the notification(s) in real-time or near real-time while a patient is engaging in an exercise session and/or after the patient has finished the exercise session. As an example, the healthcare provider may upload the treatment plan, the adjusted treatment plan, and/or the adjusted parameter one day and the patient may use the device at a later time, such as later in the day, the following morning, the following day, or the following week, etc.

In another embodiment, the method 900 receives an adjusted treatment plan, such as from the clinical portal 134. The adjusted treatment plan may be received during a telemedicine session or at another desired time. The adjusted treatment plan may include at least some different information from the treatment plan. For example, the doctor may have used the notification, client input, results from the exercise session, any other suitable information, or combination thereof to make a change to the treatment plan. The processing device may use the adjusted treatment plan to generate an adjusted parameter.

At step 916, the method 900 proceeds with using the at least one adjusted parameter to control the at least one operation of the device. The at least one adjusted parameter may be used to control the at least one operation of the device during a telemedicine session or at another desired time. In one example, if the steps taken by a patient are below an exercise session parameter (e.g., a step threshold for a day), the exercise session parameter may be adjusted to increase the amount of time for one or more modes in which the patient is to operate the electromechanical device 802 to ensure the affected body part is getting sufficient movement. The at least one adjusted parameter can be used in real-time or near real-time to control the at least one operation of the device. For example, if the healthcare provider is remotely observing the patient during the exercise session (e.g., reviewing the results of the exercise session, notifications, etc.) and provides an adjusted parameter while the patient is using the device, the at least one operation of the electromechanical device 802 can be adjusted in real-time or near real-time (e.g., providing motor assist while the patient is cycling). The at least one adjusted parameter can be received prior to the patient operating the device to control the at least one operation of the device at a time subsequent to receiving the at least one adjusted parameter. For example, the healthcare provider may determine that the patient is recovering and adjust one or more parameters (e.g., increase motor resistance on the pedals 810) to increase the intensity of the workout so that the patient can rebuild muscle strength and recover more quickly.

FIG. 9 is not intended to be limiting: the method 900 can include more or fewer steps and/or processes than those illustrated in FIG. 9. Further, the order of the steps of the method 900 is not intended to be limiting; the steps can be arranged in any suitable order.

Figure 10:
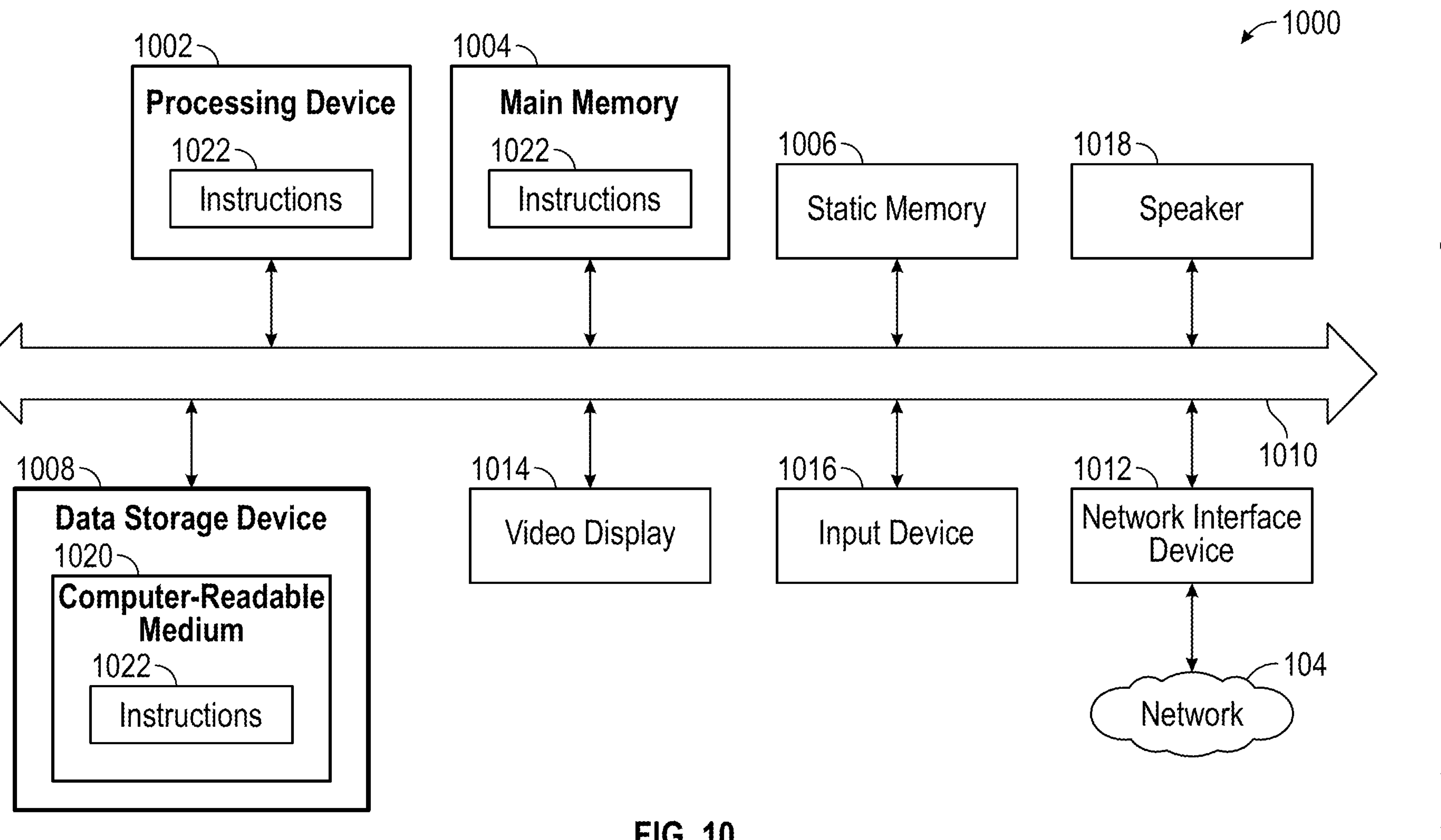
FIG. 10 generally illustrates an example computer system according to certain to certain aspects of this disclosure.

FIG. 10 illustrates, in accordance with one or more aspects of the present disclosure, an example computer system 1000 which can perform any one or more of the methods described herein. The computer system 1000 may correspond to the slave computing device 102 (e.g., a patient's computing device), the master computing device 122 (e.g., a healthcare provider's computing device), one or more servers of the cloud-based computing system 142, the training engine 146, the server 144, the slave pressure system 110, the master pressure system 130, the slave controller 118, the master controller 138, the imaging device 116, the master display 136, the treatment device 106, the master device 126, the master console 124, the treatment device 800, the motor controller 804, the electric motor 806, the radially-adjustable couplings 808, the pedals 810, the goniometer 702, and/or the wristband 704 illustrated in FIGS. 1 and/or 7. The computer system 1000 may be capable of executing the patient portal 114 and/or clinical portal 134 of FIGS. 1 and 7. The computer system 1000 may be connected (e.g., networked) to other computer systems in a LAN, an intranet, an extranet, or the Internet. The computer system 1000 may operate in the capacity of a server in a client-server network environment. The computer system may be a personal computer (PC), a tablet computer, a motor controller, a goniometer (e.g., the goniometer 702), a wearable (e.g., the wristband 704), a set-top box (STB), a personal Digital Assistant (PDA), a mobile phone, a camera, a video camera, or any device capable of executing a set of instructions (sequential or otherwise) that specify actions to be taken by that device. Further, while only a single computer system is illustrated, the term "computer" shall also be taken to include any collection of computers that individually or jointly execute a set (or multiple sets) of instructions to perform any one or more of the methods discussed herein.

The computer system 1000 includes a processing device 1002 (e.g., the slave processing device, the master processing device), a main memory 1004 (e.g., read-only memory (ROM), flash memory, dynamic random access memory (DRAM) such as synchronous DRAM (SDRAM)), a static memory 1006 (e.g., flash memory, static random access memory (SRAM)), and a data storage device 1008, which communicate with each other via a bus 1010.

The processing device 1002 represents one or more general-purpose processing devices such as a microprocessor, central processing unit, or the like. More particularly, the processing device 1002 may be a complex instruction set computing (CISC) microprocessor, reduced instruction set computing (RISC) microprocessor, very long instruction word (VLIW) microprocessor, or a processor implementing other instruction sets or processors implementing a combination of instruction sets. The processing device 1002 may also be one or more special-purpose processing devices such as an application specific integrated circuit (ASIC), a field programmable gate array (FPGA), a digital signal processor (DSP), network processor, or the like. The processing device 1002 is configured to execute instructions for performing any of the operations and steps discussed herein.

The computer system 1000 may further include a network interface device 1012. The computer system 1000 also may include a video display 1014 (e.g., a liquid crystal display (LCD), a light-emitting diode (LED), an organic light-emitting diode (OLED or Organic LED), or a cathode ray tube (CRT)). The video display 1014 can represent the master display 136 or any other suitable display. The computer system 1000 may include one or more input devices 1016 (e.g., a keyboard, a mouse, the goniometer 702, the wristband 704, the imaging device 116, or any other suitable input). The computer system 1000 may include one or more output devices (e.g., a speaker 1018). In one illustrative example, the video display 1014, the input device(s) 1016, and/or the speaker 1018 may be combined into a single component or device (e.g., an LCD touch screen).

The data storage device 1008 may include a computer-readable medium 1020 on which the instructions 1022 (e.g., implementing the control system, the patient portal 114, the clinical portal 134, and/or any functions performed by any device and/or component depicted in the FIGS. and described herein) embodying any one or more of the methodologies or functions described herein are stored. The instructions 1022 may also reside, completely or at least partially, within the main memory 1004 and/or within the processing device 1002 during execution thereof by the computer system 1000. As such, the main memory 1004 and the processing device 1002 also constitute computer-readable media. The instructions 1022 may further be transmitted or received over a network via the network interface device 1012.

While the computer-readable storage medium 1020 is shown in the illustrative examples to be a single medium, the term "computer-readable storage medium" should be taken to include a single medium or multiple media (e.g., a centralized or distributed database, and/or associated caches and servers) that store the one or more sets of instructions. The term "computer-readable storage medium" shall also be taken to include any medium capable of storing, encoding or carrying a set of instructions for execution by the machine and that cause the machine to perform any one or more of the methodologies of the present disclosure. The term "computer-readable storage medium" shall accordingly be taken to include, but not be limited to, solid-state memories, optical media, and magnetic media.

In one exemplary embodiment, the computer system 1000 includes the input device 1016 (e.g., the master console 124 comprising the master device 126) and the control system comprising the processing devices 1002 (e.g., the master processing device) operatively coupled to the input device 1016 and the treatment device 106. The system 1000 may comprise one or more memory devices (e.g., main memory 1004, data storage device 1008, etc.) operatively coupled to the processing device 1002. The one or more memory devices can be configured to store instructions 1022. The processing device 1002 can be configured to execute the instructions 1022 to receive the slave sensor data from the one or more slave sensors 108, to use a manipulation of the master device 126 to generate a manipulation instruction, to transmit the manipulation instruction, and to use the manipulation instruction to cause the slave pressure system 110 to activate. The instructions can be executed in real-time or near real-time.

The processing device 1002 can be further configured to use the slave sensor data to transmit an augmented image 400 to the video display (e.g., the master display 136). The healthcare provider may view the augmented image 400 and/or virtually touch the augmented image using the video display 1014. In other words, the augmented image 400 may comprise a representation of the treatment device 106 and one or more body parts of the patient. The representation may be displayed in 2D, 3D, or any other suitable dimension. As the healthcare provider conducts the remote examination during a telemedicine session, the augmented image 400 may change to reflect the manipulations of the treatment device 106 and/or of any movement of the patient's one or more body parts.

The augmented image 400 can comprise one or more pressure indicators, temperature indicators, any other suitable indicator, or combination thereof. Each pressure indicator can represent a measured level of force (i.e., based on the slave force measurements). Each temperature indicator can represent a measured level of temperature (i.e., based on the slave temperature measurements). For example, the pressure indicators and/or the temperature indicators may be different colors, each color associated with one of the measured levels of force and temperature, respectively. The indicators may be displayed as a map. The map may be a gradient map displaying the pressure indicators and/or temperature indicators. The map may be overlaid over the augmented image. The map may be transmitted to the clinical portal, the master display, the patient portal, any other suitable display, or combination thereof.

The processing device 1002 can be further configured to use the slave sensor data (e.g., the slave force measurements) to provide a corresponding level of measured force to the master device 126. In other words, while using the master device 126, the healthcare provider can essentially feel the measured levels of force exerted by the patient's one or more body parts during the remote examination.

As the healthcare provider is virtually examining the patient, the processing device 1002 can use the master sensor data to generate and transmit the manipulation instruction (e.g., a measured level of force) to manipulate the treatment device 106. In other words, as the healthcare provider applies more force pressure) to the master device 126, the master sensors 128 can detect the measured level of force and instruct the treatment device 106 to apply a correlated measured level of force. In some embodiments, the measured level of force can be based on a proximity of the master device 126 to the representation. In other words, as the healthcare provider manipulates the master device 126 closer to the representation and/or within the representation of the treatment device 126 and/or the patient's one or more body parts, the master sensors 128 can detect that the measured force has increased. In some embodiments, the input device 1016 can comprise a pressure gradient. Using the pressure gradient, the processing device 1002 can be configured to cause the slave pressure system 110 to apply one or more measured levels of force to one or more sections 210 of the treatment device 106.

In another exemplary embodiment, the computer system 1000 may include the input device 1016 (e.g., the treatment device 106) and the control system comprising the processing device 1002 (e.g., the slave processing device) operatively coupled to the input device 1016 and the master device 126. The system 1000 may comprise one or more memory devices (e.g., main memory 1004, data storage device 1008, etc.) operatively coupled to the processing device 1002. The one or more memory devices can be configured to store instructions 1022. The processing device 1002 can be configured to execute the instructions 1022 to receive the slave sensor data from the one or more slave sensors 108, to transmit the slave sensor data, to receive the manipulation instruction, and to use the manipulation instruction to activate the slave pressure system 110. The instructions can be executed in real-time or near real-time.

In yet another embodiment, the computer system 1000 may include one or more input devices 1016 (e.g., the master console 124 comprising the master device 126, the treatment device 106, etc.) and the control system comprising one or more processing devices 1002 (e.g., the master processing device, the slave processing device) operatively coupled to the input devices 1016. For example, the master processing device may be operatively coupled to the master console 124 and the slave processing device may be operatively coupled to the treatment device 106. The system 1000 may comprise one or more memory devices (e.g., master memory coupled to the master processing device, slave memory coupled to the slave processing device, etc.) operatively coupled to the one or more processing devices 1002. The one or more memory devices can be configured to store instructions 1022 (e.g., master instructions, slave instructions, etc.). The one or more processing devices 1002 (e.g., the master processing device) can be configured to execute the master instructions 1022 to receive the slave sensor data from the slave processing device, use a manipulation of the master device 126 to generate a manipulation instruction, and transmit the manipulation instruction to the slave processing device. The one or more processing devices 1002 (e.g., the slave processing device) can be configured to execute the slave instructions 1022 to receive the slave sensor data from the one or more slave sensors, to transmit the slave sensor data to the master processing device, to receive the manipulation instruction from the master processing device, and to use the manipulation instruction to activate the slave pressure system. The instructions can be executed in real-time or near real-time.

In another exemplary embodiment, the computer system 1000 may include the input device 1016 (e.g., the treatment device 800) and the control system comprising the processing device 1002 (e.g., the slave processing device) operatively coupled to the input device 1016 and the master computing device 122. The system 1000 may comprise one or more memory devices (e.g., main memory 1004, data storage device 1008, etc.) operatively coupled to the processing device 1002. The one or more memory devices can be configured to store instructions 1022. The processing device 1002 can be configured to execute the instructions 1022 to receive a treatment plan (e.g., from a clinical portal 134) for a patient and to use the treatment plan to generate at least one parameter. The at least one parameter can be at least one of a force parameter, a resistance parameter, a range of motion parameter, a temperature parameter, a pain level parameter, an exercise session parameter, a vital sign parameter, and a time parameter. Responsive to the at least one trigger condition occurring, the instructions can further cause the processing device 1002 to control at least one operation of the treatment device 800. The controlling of the at least one operation of the device can comprise causing the treatment device 800 to modify at least one of a volume, a pressure, a resistance, an angle, a speed, an angular or rotational velocity, and a time period. The processing device 1002 can be further configured to execute the instructions 1022 to receive the slave sensor data (e.g., data associated with the at least one operation) from the one or more slave sensors 108. To determine the at least one trigger condition, the instructions 1022 can further cause the processing device 1002 to use at least one of the data, the at least one parameter, and a patient input. The instructions 1022 can be executed in real-time or near real-time. For example, a notification can be transmitted to the clinical portal 134 in real-time or near real-time, the at least one adjusted parameter can be received in real-time or near real-time, and, using the at least one adjusted parameter, the at least one operation of the treatment device 800 can be controlled in real-time or near real-time. The instructions 1022 can be executed at any other suitable time. For example, the notification can be transmitted to a clinical portal 134 at a first time, the at least one adjusted parameter can be received by the treatment device 800 at a second time, and, using the at least one adjusted parameter, the at least one operation of the treatment device 800 can be controlled at a third time subsequent to the first and second times (i.e., subsequent to transmitting the notification and receiving the at least one adjusted parameter).

FIG. 10 is not intended to be limiting: the system 1000 may include more or fewer components than those illustrated in FIG. 10.

Any of the systems and methods described in this disclosure may be used in connection with rehabilitation. Unless expressly stated otherwise, is to be understood that rehabilitation includes prehabilitation (also referred to as "pre-habilitation" or "prehab"). Prehabilitation may be used as a preventative procedure or as a pre-surgical or pre-treatment procedure. Prehabilitation may include any action performed by or on a patient (or directed to be performed by or on a patient, including, without limitation, remotely or distally through telemedicine) to, without limitation, prevent or reduce a likelihood of injury (e.g., prior to the occurrence of the injury); improve recovery time subsequent to surgery; improve strength subsequent to surgery; or any of the foregoing with respect to any non-surgical clinical treatment plan to be undertaken for the purpose of ameliorating or mitigating injury, dysfunction, or other negative consequence of surgical or non-surgical treatment on any external or internal part of a patient's body. For example, a mastectomy may require prehabilitation to strengthen muscles or muscle groups affected directly or indirectly by the mastectomy. As a further non-limiting example, the removal of an intestinal tumor, the repair of a hernia, open-heart surgery or other procedures performed on internal organs or structures, whether to repair those organs or structures, to excise them or parts of them, to treat them, etc., can require cutting through and harming numerous muscles and muscle groups in or about, without limitation, the abdomen, the ribs and/or the thoracic cavity. Prehabilitation can improve a patient's speed of recovery, measure of quality of life, level of pain, etc. in all the foregoing procedures. In one embodiment of prehabilitation, a pre-surgical procedure or a pre-non-surgical-treatment may include one or more sets of exercises for a patient to perform prior to such procedure or treatment. The patient may prepare an area of his or her body for the surgical procedure by performing the one or more sets of exercises, thereby strengthening muscle groups, improving existing and/or establishing new muscle memory, enhancing mobility, improving blood flow, and/or the like.

In some embodiments, the systems and methods described herein may use artificial intelligence and/or machine learning to generate a prehabilitation treatment plan for a user. Additionally, or alternatively, the systems and methods described herein may use artificial intelligence and/or machine learning to recommend an optimal exercise machine configuration for a user. For example, a data model may be trained on historical data such that the data model may be provided with input data relating to the user and may generate output data indicative of a recommended exercise machine configuration for a specific user. Additionally, or alternatively, the systems and methods described herein may use machine learning and/or artificial intelligence to generate other types of recommendations relating to prehabilitation, such as recommended reading material to educate the patient, a recommended health professional specialist to contact, and/or the like.

Consistent with the above disclosure, the examples of systems and methods enumerated in the following clauses are specifically contemplated and are intended as a non-limiting set of examples.

Clause 1. A computer-implemented system, comprising:

- a treatment device configured to be manipulated by a user while the user performs a treatment plan;
- a patient interface comprising an output device configured to present telemedicine information associated with a telemedicine session; and
- a processing device configured to:
  - receive a treatment plan for a patient;
  - during the telemedicine session, use the treatment plan to generate at least one parameter; and
  - responsive to at least one trigger condition occurring, control at least one operation of the treatment device.

Clause 2. The computer-implemented system of any clause herein, wherein the treatment device comprises a sensor for detecting data associated with the at least one operation.

Clause 3. The computer-implemented system of any clause herein, wherein the processing device is configured to receive the data from the sensor in real-time or near real-time.

Clause 4. The computer-implemented system of any clause herein, wherein, to determine the at least one trigger condition, the one or more processing devices are configured to use at least one of the data, the at least one parameter, and a patient input.

Clause 5. The computer-implemented system of any clause herein, wherein the controlling of the at least one operation of the device comprises causing the device to modify at least one of a volume, a pressure, a resistance, an angle, a speed, an angular or rotational velocity, and a time period.

Clause 6. The computer-implemented system of any clause herein, wherein the at least one parameter is at least one of a force parameter, a resistance parameter, a range of motion parameter, a temperature parameter, a pain level parameter, an exercise session parameter, a vital sign parameter, and a time parameter.

Clause 7. A system for a remote examination of a patient, comprising:

- a master console comprising a master device;
- a treatment device comprising one or more slave sensors and a slave pressure system; and
- a control system comprising one or more processing devices operatively coupled to the master console and the treatment device, wherein the one or more processing devices are configured to:
  - receive slave sensor data from the one or more slave sensors;
  - use a manipulation of the master device to generate a manipulation instruction;
  - transmit the manipulation instruction; and
  - use the manipulation instruction to cause the slave pressure system to activate.

Clause 8. The system of any clause herein, wherein the master device comprises master sensors for detecting master sensor data associated with the manipulation; and wherein the manipulation instruction is based on the master sensor data.

Clause 9. The system of any clause herein, wherein the slave sensor data comprises slave force measurements;

wherein the master device comprises a master pressure system; and wherein, using the slave force measurements, the one or more processing devices are further configured to activate the master pressure system.

Clause 10. The system of any clause herein, further comprising:

a second master device comprising a second master pressure system;

wherein the slave sensor data comprises slave force measurements; and wherein, using the slave force measurements, the one or more processing devices are further configured to activate the second master pressure system.

Clause 11. The system of any clause herein, wherein the one or more processing devices are further configured to:

use the slave sensor data to transmit an augmented image to a master display.

Clause 12. The system of any clause herein, wherein the slave sensor data comprises slave force measurements;

wherein the augmented image comprises one or more pressure indicators; and wherein the one or more pressure indicators are based on the slave force measurements.

Clause 13. The system of any clause herein, wherein the slave sensor data comprises slave temperature measurements;

wherein the augmented image comprises one or more temperature indicators; and wherein the one or more temperature indicators are based on the slave temperature measurements.

Clause 14. The system of any clause herein, wherein the master device comprises a pressure gradient; and wherein, using the pressure gradient, the one or more processing devices are configured to cause the slave pressure system to apply one or more measured levels of force to one or more sections of the treatment device.

Clause 15. The system of any clause herein, wherein the augmented image comprises a representation of at least one of the treatment device and a body part of the patient, and wherein the representation is in 2D or 3D.

Clause 16. The system of any clause herein, wherein the manipulation instruction comprises a measured level of force; and wherein the measured level of force is based on a proximity of the master device to the representation.

Clause 17. The system of any clause herein, wherein the one or more processing devices are further configured to:

transmit the manipulation instruction in real-time or near real-time; and cause the slave pressure system to activate in real-time or near real-time.

Clause 18. The system of any clause herein, wherein the master device comprises at least one of a glove device, a joystick, and a model of the treatment device.

Clause 19. The system of any clause herein, wherein the treatment device comprises at least one of a brace, a cap, a mat, and a wrap.

Clause 20. The system of any clause herein, further comprising one or more memory devices operatively coupled to the one or more processing devices, wherein the one or more memory devices stores instructions, and wherein the one or more processing devices are configured to execute the instructions.

Clause 21. A method for operating a system for remote examination of a patient, comprising:

receiving slave sensor data from one or more slave sensors;

based on a manipulation of a master device, generating a manipulation instruction;

transmitting the manipulation instruction; and based on the manipulation instruction, causing a slave pressure system to activate.

Clause 22. The method of any clause herein, wherein the master device comprises master sensors for detecting master sensor data associated with the manipulation; and wherein the manipulation instruction is based on the master sensor data.

Clause 23. The method of any clause herein, wherein the slave sensor data comprises slave force measurements;

wherein the master device comprises a master pressure system; and wherein, based on the slave force measurements, activating the master pressure system.

Clause 24. The method of any clause herein, further comprising:

a second master device comprising a second master pressure system;

wherein the slave sensor data comprises slave force measurements; and wherein, using the slave force measurements, the one or more processing devices are further configured to activate the second master pressure system.

Clause 25. The method of any clause herein, further comprising:

use the slave sensor data to transmitting an augmented image.

Clause 26. The method of any clause herein, wherein the slave sensor data comprises slave force measurements;

wherein the augmented image comprises one or more pressure indicators; and wherein the one or more pressure indicators are based on the slave force measurements.

Clause 27. The method of any clause herein, wherein the slave sensor data comprises slave temperature measurements;

wherein the augmented image comprises one or more temperature indicators; and wherein the one or more temperature indicators are based on the slave temperature measurements.

Clause 28. The method of any clause herein, wherein the master device comprises a pressure gradient; and wherein, using the pressure gradient, causing the slave pressure system to apply one or more measured levels of force to one or more sections of the treatment device.

Clause 29. The method of any clause herein, wherein the augmented image comprises a representation of at least one of the treatment device and a body part of the patient, and wherein the representation is in 2D or 3D.

Clause 30. The method of any clause herein, wherein the manipulation instruction comprises a measured level of force; and wherein the measured level of force is based on a proximity of the master device to the representation.

Clause 31. The method of any clause herein, further comprising:

transmitting the manipulation instruction in real-time or near real-time; and causing the slave pressure system to activate in real-time or near real-time.

Clause 32. The method of any clause herein, wherein the master device comprises at least one of a glove device, a joystick, and a model of the treatment device.

Clause 33. The method of any clause herein, wherein the treatment device comprises at least one of a brace, a cap, a mat, and a wrap.

Clause 34. A tangible, non-transitory computer-readable storage medium storing instructions that, when executed, cause a processing device to:

receive slave sensor data from one or more slave sensors;

based on a manipulation of a master device, generate a manipulation instruction;

transmit the manipulation instruction; and use the manipulation instruction to cause a slave pressure system to activate.

Clause 35. The tangible, non-transitory computer-readable storage medium of any clause herein, wherein the master device comprises master sensors for detecting master sensor data associated with the manipulation; and wherein the manipulation instruction is based on the master sensor data.

Clause 36. The tangible, non-transitory computer-readable storage medium of any clause herein, wherein the slave sensor data comprises slave force measurements;

wherein the master device comprises a master pressure system; and wherein, based on the slave force measurements, activate the master pressure system.

Clause 37. The tangible, non-transitory computer-readable storage medium of any clause herein, further comprising:

a second master device comprising a second master pressure system;

wherein the slave sensor data comprises slave force measurements; and wherein, using the slave force measurements, the one or more processing devices are further configured to activate the second master pressure system.

Clause 38. The tangible, non-transitory computer-readable storage medium of any clause herein, wherein the instructions further cause the processing device to:

use the slave sensor data to transmit an augmented image.

Clause 39. The tangible, non-transitory computer-readable storage medium of any clause herein, wherein the slave sensor data comprises slave force measurements;

wherein the augmented image comprises one or more pressure indicators; and wherein the one or more pressure indicators are based on the slave force measurements.

Clause 40. The tangible, non-transitory computer-readable storage medium of any clause herein, wherein the slave sensor data comprises slave temperature measurements;

wherein the augmented image comprises one or more temperature indicators; and wherein the one or more temperature indicators are based on the slave temperature measurements.

Clause 41. The tangible, non-transitory computer-readable storage medium of any clause herein, wherein the master device comprises a pressure gradient; and wherein, using the pressure gradient, cause the slave pressure system to apply one or more measured levels of force to one or more sections of the treatment device.

Clause 42. The tangible, non-transitory computer-readable storage medium of any clause herein, wherein the augmented image comprises a representation of at least one of the treatment device and a body part of the patient, and wherein the representation is in 2D or 3D.

Clause 43. The tangible, non-transitory computer-readable storage medium of any clause herein, wherein the manipulation instruction comprises a measured level of force; and wherein the measured level of force is based on a proximity of the master device to the representation.

Clause 44. The tangible, non-transitory computer-readable storage medium of any clause herein, wherein the instructions further cause the processing device to:

transmit the manipulation instruction in real-time or near real-time; and cause the slave pressure system to activate in real-time or near real-time.

Clause 45. The tangible, non-transitory computer-readable storage medium of any clause herein, wherein the master device comprises at least one of a glove device, a joystick, and a model of the treatment device.

Clause 46. The tangible, non-transitory computer-readable storage medium of any clause herein, wherein the treatment device comprises at least one of a brace, a cap, a mat, and a wrap.

Clause 47. A system for a remote examination of a patient, comprising:

a master console comprising a master device;

a treatment device comprising one or more slave sensors and a slave pressure system; and a control system comprising one or more processing devices operatively coupled to the master console and the treatment device, wherein the one or more processing devices are configured to:

receive slave sensor data from the one or more slave sensors;

transmit the slave sensor data;

receive a manipulation instruction; and use the manipulation instruction to activate the slave pressure system.

Clause 48. The system of any clause herein, wherein the manipulation instruction is based on a manipulation of the master device.

Clause 49. The system of any clause herein, wherein the master device comprises master sensors for detecting master sensor data associated with the manipulation; and wherein the manipulation instruction is based on the master sensor data.

Clause 50. The system of any clause herein, further comprising:

a second master device comprising a second master pressure system;

wherein the slave sensor data comprises slave force measurements; and wherein, using the slave force measurements, the one or more processing devices are further configured to activate the second master pressure system.

Clause 51. The system of any clause herein, wherein the one or more processing devices are further configured to:

use the slave sensor data to transmit an augmented image to the master console.

Clause 52. The system of any clause herein, wherein the slave sensor data comprises slave force measurements;

wherein the master device comprises a master pressure system; and wherein, using the slave force measurements, the one or more processing devices are further configured to cause the master pressure system to activate.

Clause 53. The system of any clause herein, wherein the slave sensor data comprises slave force measurements;

wherein the augmented image comprises one or more pressure indicators; and wherein the one or more pressure indicators are based on the slave force measurements.

Clause 54. The system of any clause herein, wherein the slave sensor data comprises slave temperature measurements;

wherein the augmented image comprises one or more temperature indicators; and wherein the one or more temperature indicators are based on the slave temperature measurements.

Clause 55. The system of any clause herein, wherein the master device comprises a pressure gradient; and wherein, using the pressure gradient, activating the slave pressure system comprises applying one or more measured levels of force to one or more sections of the treatment device.

Clause 56. The system of any clause herein, wherein the augmented image comprises a representation of at least one of the treatment device and a body part of the patient, and wherein the representation is in 2D or 3D.

Clause 57. The system of any clause herein, wherein the manipulation instruction comprises a measured level of force; and wherein the measured level of force is based on a proximity of the master device to the representation.

Clause 58. The system of any clause herein, wherein the one or more processing devices are further configured to:

receive the manipulation instruction in real-time or near real-time; and activate the slave pressure system in real-time or near real-time.

Clause 59. The system of any clause herein, wherein the master device comprises at least one of a glove device, a joystick, and a model of the treatment device.

Clause 60. The system of any clause herein, wherein the treatment device comprises at least one of a brace, a cap, a mat, and a wrap.

Clause 61. The system of any clause herein, further comprising one or more memory devices operatively coupled to the one or more processing devices, wherein the one or more memory devices stores instructions, and wherein the one or more processing devices are configured to execute the instructions.

Clause 62. A method for operating a system for remote examination of a patient, comprising:

receiving slave sensor data from one or more slave sensors;

transmitting the slave sensor data;

receiving a manipulation instruction; and based on the manipulation instruction, activating a slave pressure system.

Clause 63. The method of any clause herein, wherein the manipulation instruction is based on a manipulation of a master device.

Clause 64. The method of any clause herein, wherein the master device comprises master sensors for detecting master sensor data associated with the manipulation; and wherein the manipulation instruction is based on the master sensor data.

Clause 65. The method of any clause herein, further comprising:

a second master device comprising a second master pressure system;

wherein the slave sensor data comprises slave force measurements; and wherein, using the slave force measurements, the one or more processing devices are further configured to activate the second master pressure system.

Clause 66. The method of any clause herein, further comprising:

use the slave sensor data to transmitting an augmented image to the master console.

Clause 67. The method of any clause herein, wherein the slave sensor data comprises slave force measurements;

wherein the master device comprises a master pressure system; and wherein, based on the slave force measurements, causing the master pressure system to activate.

Clause 68. The method of any clause herein, wherein the slave sensor data comprises slave force measurements;

wherein the augmented image comprises one or more pressure indicators; and wherein the one or more pressure indicators are based on the slave force measurements.

Clause 69. The method of any clause herein, wherein the slave sensor data comprises slave temperature measurements;

wherein the augmented image comprises one or more temperature indicators; and wherein the one or more temperature indicators are based on the slave temperature measurements.

Clause 70. The method of any clause herein, wherein the master device comprises a pressure gradient; and wherein, using the pressure gradient, activating the slave pressure system comprises applying one or more measured levels of force to one or more sections of the treatment device.

Clause 71. The method of any clause herein, wherein the augmented image comprises a representation of at least one of the treatment device and a body part of the patient, and wherein the representation is in 2D or 3D.

Clause 72. The method of any clause herein, wherein the manipulation instruction comprises a measured level of force; and wherein the measured level of force is based on a proximity of the master device to the representation.

Clause 73. The method of any clause herein, further comprising:

receiving the manipulation instruction in real-time or near real-time; and activating the slave pressure system in real-time or near real-time.

Clause 74. The method of any clause herein, wherein the master device comprises at least one of a glove device, a joystick, and a model of the treatment device.

Clause 75. The method of any clause herein, wherein the treatment device comprises at least one of a brace, a cap, a mat, and a wrap.

Clause 76. A tangible, non-transitory computer-readable storage medium storing instructions that, when executed, cause a processing device to:

receive slave sensor data from one or more slave sensors;

transmit the slave sensor data;

receive a manipulation instruction; and use the manipulation instruction to activate a slave pressure system.

Clause 77. The tangible, non-transitory computer-readable storage medium of any clause herein, wherein the manipulation instruction is based on a manipulation of a master device.

Clause 78. The tangible, non-transitory computer-readable storage medium of any clause herein, wherein the master device comprises master sensors for detecting master sensor data associated with the manipulation; and wherein the manipulation instruction is based on the master sensor data.

Clause 79. The tangible, non-transitory computer-readable storage medium of any clause herein, further comprising:

a second master device comprising a second master pressure system;

wherein the slave sensor data comprises slave force measurements; and wherein, using the slave force measurements, the one or more processing devices are further configured to activate the second master pressure system.

Clause 80. The tangible, non-transitory computer-readable storage medium of any clause herein, wherein the instructions further cause the processing device to:

use the slave sensor data to transmit an augmented image to the master console.

Clause 81. The tangible, non-transitory computer-readable storage medium of any clause herein, wherein the slave sensor data comprises slave force measurements;

wherein the master device comprises a master pressure system; and wherein, based on the slave force measurements, cause the master pressure system to activate.

Clause 82. The tangible, non-transitory computer-readable storage medium of any clause herein, wherein the slave sensor data comprises slave force measurements;

wherein the augmented image comprises one or more pressure indicators; and wherein the one or more pressure indicators are based on the slave force measurements.

Clause 83. The method of any clause herein, wherein the slave sensor data comprises slave temperature measurements;

wherein the augmented image comprises one or more temperature indicators; and wherein the one or more temperature indicators are based on the slave temperature measurements.

Clause 84. The method of any clause herein, wherein the master device comprises a pressure gradient; and wherein, using the pressure gradient, activating the slave pressure system comprises applying one or more measured levels of force to one or more sections of the treatment device.

Clause 85. The method of any clause herein, wherein the augmented image comprises a representation of at least one of the treatment device and a body part of the patient, and wherein the representation is in 2D or 3D.

Clause 86. The tangible, non-transitory computer-readable storage medium of any clause herein, wherein the manipulation instruction comprises a measured level of force; and wherein the measured level of force is based on a proximity of the master device to the representation.

Clause 87. The tangible, non-transitory computer-readable storage medium of any clause herein, wherein the instructions further cause the processing device to:

receive the manipulation instruction in real-time or near real-time; and activate the slave pressure system in real-time or near real-time.

Clause 88. The tangible, non-transitory computer-readable storage medium of any clause herein, wherein the master device comprises at least one of a glove device, a joystick, and a model of the treatment device.

Clause 89. The tangible, non-transitory computer-readable storage medium of any clause herein, wherein the treatment device comprises at least one of a brace, a cap, a mat, and a wrap.

Clause 90. A system for a remote examination of a patient, comprising:

a master console comprising a master device;

a treatment device comprising one or more slave sensors and a slave pressure system; and a control system comprising a master processing device and a slave processing device, wherein the master processing device is operatively coupled to the master console and the slave processing device is operatively coupled to the treatment device;

wherein the master processing device is configured to:

receive slave sensor data from the slave processing device;

use a manipulation of the master device to generate a manipulation instruction; and transmit the manipulation instruction to the slave processing device; and wherein the slave processing device is configured to:

receive the slave sensor data from the one or more slave sensors;

transmit the slave sensor data to the master processing device;

receive the manipulation instruction from the master processing device; and use the manipulation instruction to activate the slave pressure system.

Clause 91. The system of any clause herein, wherein the master device comprises master sensors for detecting master sensor data associated with the manipulation; and wherein the manipulation instruction is based on the master sensor data.

Clause 92. The system of any clause herein, wherein the slave sensor data comprises slave force measurements;

wherein the master device comprises a master pressure system; and wherein, using the slave force measurements, the master processing device is further configured to activate the master pressure system.

Clause 93. The system of any clause herein, further comprising:

a second master device comprising a second master pressure system;

wherein the slave sensor data comprises slave force measurements; and wherein, using the slave force measurements, the master processing device is further configured to activate the second master pressure system.

Clause 94. The system of any clause herein, wherein the master processing device is further configured to:

use the slave sensor data to transmit an augmented image to a master display.

Clause 95. The system of any clause herein, wherein the slave sensor data comprises slave force measurements;

wherein the augmented image comprises one or more pressure indicators; and wherein the one or more pressure indicators are based on the slave force measurements.

Clause 96. The system of any clause herein, wherein the slave sensor data comprises slave temperature measurements;

wherein the augmented image comprises one or more temperature indicators; and wherein the one or more temperature indicators are based on the slave temperature measurements.

Clause 97. The system of any clause herein, wherein the master device comprises a pressure gradient; and wherein, using the pressure gradient, activating the slave pressure system comprises applying one or more measured levels of force to one or more sections of the treatment device.

Clause 98. The system of any clause herein, wherein the augmented image comprises a representation of at least one of the treatment device and a body part of the patient, and wherein the representation is in 2D or 3D.

Clause 99. The system of any clause herein, wherein the manipulation instruction comprises a measured level of force; and wherein the measured level of force is based on a proximity of the master device to the representation.

Clause 100. The system of any clause herein, wherein the manipulation instruction is transmitted in real-time or near real-time; and wherein the slave pressure system is activated in real-time or near real-time.

Clause 101. The system of any clause herein, wherein the master device comprises at least one of a glove device, a joystick, and a model of the treatment device.

Clause 102. The system of any clause herein, wherein the treatment device comprises at least one of a brace, a cap, a mat, and a wrap.

Clause 103. The system of any clause herein, further comprising:

a master memory device operatively coupled to the master processing device, wherein the master memory device stores master instructions, and wherein the master processing device is configured to execute the master instructions; and a slave memory device operatively coupled to the slave processing device, wherein the slave memory device stores slave instructions, and wherein the slave processing device is configured to execute the slave instructions.

Clause 104. A method for operating a remote examination of a patient, comprising:

causing a master processing device to:

receive slave sensor data from the slave processing device;

use a manipulation of a master device to generate a manipulation instruction; and transmit the manipulation instruction to the slave processing device; and causing a slave processing device to:

receive the slave sensor data from the one or more slave sensors;

transmit the slave sensor data to the master processing device;

receive the manipulation instruction from the master processing device; and use the manipulation instruction to activate the slave pressure system.

Clause 105. The method of any clause herein, wherein the master device comprises master sensors for detecting master sensor data associated with the manipulation; and wherein the manipulation instruction is based on the master sensor data.

Clause 106. The method of any clause herein, wherein the slave sensor data comprises slave force measurements;

wherein the master device comprises a master pressure system; and causing the master processing device, based on the slave force measurements, to activate the master pressure system.

Clause 107. The method of any clause herein, further comprising:

a second master device comprising a second master pressure system;

wherein the slave sensor data comprises slave force measurements; and wherein, using the slave force measurements, the master processing device is further configured to activate the second master pressure system.

Clause 108. The method of any clause herein, further causing the master processing device to:

use the slave sensor data to transmit an augmented image to a master display.

Clause 109. The method of any clause herein, wherein the slave sensor data comprises slave force measurements;

wherein the augmented image comprises one or more pressure indicators; and wherein the one or more pressure indicators are based on the slave force measurements.

Clause 110. The method of any clause herein, wherein the slave sensor data comprises slave temperature measurements;

wherein the augmented image comprises one or more temperature indicators; and wherein the one or more temperature indicators are based on the slave temperature measurements.

Clause 111. The method of any clause herein, wherein the master device comprises a pressure gradient; and wherein, using the pressure gradient, activating the slave pressure system comprises applying one or more measured levels of force to one or more sections of the treatment device.

Clause 112. The method of any clause herein, wherein the augmented image comprises a representation of at least one of the treatment device and a body part of the patient, and wherein the representation is in 2D or 3D.

Clause 113. The method of any clause herein, wherein the manipulation instruction comprises a measured level of force; and wherein the measured level of force is based on a proximity of the master device to the representation.

Clause 114. The method of any clause herein, wherein the manipulation instruction is transmitted in real-time or near real-time; and wherein the slave pressure system is activated in real-time or near real-time.

Clause 115. The method of any clause herein, wherein the master device comprises at least one of a glove device, a joystick, and a model of the treatment device.

Clause 116. The method of any clause herein, wherein the treatment device comprises at least one of a brace, a cap, a mat, and a wrap.

Clause 117. A tangible, non-transitory computer-readable storage medium storing instructions that, when executed, cause a master processing device to:

receive slave sensor data from the slave processing device;

use a manipulation of a master device to generate a manipulation instruction; and transmit the manipulation instruction to the slave processing device; and cause a slave processing device to:

receive the slave sensor data from the one or more slave sensors;

transmit the slave sensor data to the master processing device;

receive the manipulation instruction from the master processing device; and use the manipulation instruction to activate the slave pressure system.

Clause 118. The tangible, non-transitory computer-readable storage medium of any clause herein, wherein the master device comprises master sensors for detecting master sensor data associated with the manipulation; and wherein the manipulation instruction is based on the master sensor data.

Clause 119. The tangible, non-transitory computer-readable storage medium of any clause herein, wherein the slave sensor data comprises slave force measurements;

wherein the master device comprises a master pressure system; and wherein, using the slave force measurements, the master processing device is further configured to activate the master pressure system.

Clause 120. The tangible, non-transitory computer-readable storage medium of any clause herein, further comprising:

a second master device comprising a second master pressure system;

wherein the slave sensor data comprises slave force measurements; and wherein, using the slave force measurements, the master processing device is further configured to activate the second master pressure system.

Clause 121. The tangible, non-transitory computer-readable storage medium of any clause herein, wherein instructions further cause the master processing device to:

use the slave sensor data to transmit an augmented image to a master display.

Clause 122. The tangible, non-transitory computer-readable storage medium of any clause herein, wherein the slave sensor data comprises slave force measurements;

wherein the augmented image comprises one or more pressure indicators; and wherein the one or more pressure indicators are based on the slave force measurements.

Clause 123. The tangible, non-transitory computer-readable storage medium of any clause herein, wherein the slave sensor data comprises slave temperature measurements;

wherein the augmented image comprises one or more temperature indicators; and wherein the one or more temperature indicators are based on the slave temperature measurements.

Clause 124. The tangible, non-transitory computer-readable storage medium of any clause herein, wherein the master device comprises a pressure gradient; and wherein, using the pressure gradient, activating the slave pressure system comprises applying one or more measured levels of force to one or more sections of the treatment device.

Clause 125. The tangible, non-transitory computer-readable storage medium of any clause herein, wherein the augmented image comprises a representation of at least one of the treatment device and a body part of the patient, and wherein the representation is in 2D or 3D.

Clause 126. The tangible, non-transitory computer-readable storage medium of any clause herein, wherein the manipulation instruction comprises a measured level of force; and wherein the measured level of force is based on a proximity of the master device to the representation.

Clause 127. The tangible, non-transitory computer-readable storage medium of any clause herein, wherein the manipulation instruction is transmitted in real-time or near real-time; and wherein the slave pressure system is activated in real-time or near real-time.

Clause 128. The tangible, non-transitory computer-readable storage medium of any clause herein, wherein the master device comprises at least one of a glove device, a joystick, and a model of the treatment device.

Clause 129. The tangible, non-transitory computer-readable storage medium of any clause herein, wherein the treatment device comprises at least one of a brace, a cap, a mat, and a wrap.

Clause 130. The tangible, non-transitory computer-readable storage medium of any clause herein, further comprising:

a master memory device operatively coupled to the master processing device, wherein the master memory device stores master instructions, and wherein the master processing device is configured to execute the master instructions; and a slave memory device operatively coupled to the slave processing device, wherein the slave memory device stores slave instructions, and wherein the slave processing device is configured to execute the slave instructions.

Clause 131. A system for enabling a remote adjustment of a device, comprising:

a control system comprising one or more processing devices operatively coupled to the device, wherein the one or more processing devices are configured to:

receive a treatment plan for a patient;

use the treatment plan to generate at least one parameter; and responsive to at least one trigger condition occurring, control at least one operation of the device.

Clause 132. The system of any clause herein, wherein the device comprises a sensor for detecting data associated with the at least one operation.

Clause 133. The system of any clause herein, wherein the one or more processing devices are configured to receive the data from the sensor in real-time or near real-time.

Clause 134. The system of any clause herein, wherein, to determine the at least one trigger condition, the one or more processing devices are configured to use at least one of the data, the at least one parameter, and a patient input.

Clause 135. The system of any clause herein, wherein the controlling of the at least one operation of the device comprises causing the device to modify at least one of a volume, a pressure, a resistance, an angle, a speed, an angular or rotational velocity, and a time period.

Clause 136. The system of any clause herein, wherein the at least one parameter is at least one of a force parameter, a resistance parameter, a range of motion parameter, a temperature parameter, a pain level parameter, an exercise session parameter, a vital sign parameter, and a time parameter.

Clause 137. The system of any clause herein, wherein the one or more processing devices are configured to receive the treatment plan from a clinical portal.

Clause 138. The system of any clause herein, wherein the one or more processing devices are further configured to:

transmit a notification to a clinical portal in real-time or near real-time;

receive at least one adjusted parameter in real-time or near real-time; and using the at least one adjusted parameter, control the at least one operation of the device in real-time or near real-time.

Clause 139. The system of any clause herein, wherein the one or more processing devices are further configured to:

transmit a notification to a clinical portal;

receive at least one adjusted parameter; and using the at least one adjusted parameter, control the at least one operation of the device at a time subsequent to receiving the at least one adjusted parameter.

Clause 140. The system of any clause herein, wherein the device comprises at least one of a physical therapy device, a brace, a cap, a mat, and a wrap.

Clause 141. A method for enabling a remote adjustment of a device, comprising:

receiving a treatment plan for a patient;

using the treatment plan to generate at least one parameter; and responsive to at least one trigger condition occurring, controlling at least one operation of the device.

Clause 142. The method of any clause herein, wherein the device comprises a sensor for detecting data associated with the at least one operation.

Clause 143. The method of any clause herein, wherein the data is received from the sensor in real-time or near real-time.

Clause 144. The method of any clause herein, further comprising:

to determine the at least one trigger condition, using at least one of the data, the at least one parameter, and a patient input.

Clause 145. The method of any clause herein, wherein the controlling of the at least one operation of the device comprises causing the device to modify at least one of a volume, a pressure, a resistance, an angle, a speed, an angular or rotational velocity, and a time period.

Clause 146. The method of any clause herein, wherein the at least one parameter is at least one of a force parameter, a resistance parameter, a range of motion parameter, a temperature parameter, a pain level parameter, an exercise session parameter, a vital sign parameter, and a time parameter.

Clause 147. The method of any clause herein, wherein the treatment plan is received from a clinical portal.

Clause 148. The method of any clause herein, further comprising:

transmitting a notification to a clinical portal in real-time or near real-time;

receiving at least one adjusted parameter in real-time or near real-time; and using the at least one adjusted parameter to control the at least one operation of the device in real-time or near real-time.

Clause 149. The method of any clause herein, further comprising:

transmitting a notification to a clinical portal;

receiving at least one adjusted parameter; and using the at least one adjusted parameter to control the at least one operation of the device at a time subsequent to receiving the at least one adjusted parameter.

Clause 150. The method of any clause herein, wherein the device comprises at least one of a physical therapy device, a brace, a cap, a mat, and a wrap.

Clause 151. A tangible, non-transitory computer-readable storage medium storing instructions that, when executed, cause a processor to:

receive a treatment plan for a patient;

use the treatment plan to generate at least one parameter; and responsive to at least one trigger condition occurring, control at least one operation of a device.

Clause 152. The tangible, non-transitory computer-readable storage medium of any clause herein, wherein the device comprises a sensor for detecting data associated with the at least one operation.

Clause 153. The tangible, non-transitory computer-readable storage medium of any clause herein, wherein the instructions further cause the processor to receive the data from the sensor in real-time or near real-time.

Clause 154. The tangible, non-transitory computer-readable storage medium of any clause herein, wherein, to determine the at least one trigger condition, the instructions further cause the processor to use at least one of the data, the at least one parameter, and a patient input.

Clause 155. The tangible, non-transitory computer-readable storage medium of any clause herein, wherein the controlling of the at least one operation of the device comprises causing the device to modify at least one of a volume, a pressure, a resistance, an angle, a speed, an angular or rotational velocity, and a time period.

Clause 156. The tangible, non-transitory computer-readable storage medium of any clause herein, wherein the at least one parameter is at least one of a force parameter, a resistance parameter, a range of motion parameter, a temperature parameter, a pain level parameter, an exercise session parameter, a vital sign parameter, and a time parameter.

Clause 157. The tangible, non-transitory computer-readable storage medium of any clause herein, wherein the treatment plan is received from a clinical portal.

Clause 158. The tangible, non-transitory computer-readable storage medium of any clause herein, wherein the instructions further cause the processor to:

transmit a notification to a clinical portal in real-time or near real-time;

receive at least one adjusted parameter in real-time or near real-time; and using the at least one adjusted parameter, control the at least one operation of the device in real-time or near real-time.

Clause 159. The tangible, non-transitory computer-readable storage medium of any clause herein, wherein the instructions further cause the processor to:

transmit a notification to a clinical portal;

receive at least one adjusted parameter; and using the at least one adjusted parameter, control the at least one operation of the device at a time subsequent to receiving the at least one adjusted parameter.

Clause 160. The tangible, non-transitory computer-readable storage medium of any clause herein, wherein the device comprises at least one of a physical therapy device, a brace, a cap, a mat, and a wrap.

Consistent with the above disclosure, the examples of assemblies enumerated in the following clauses are specifically contemplated and are intended as a non-limiting set of examples.

No part of the description in this application should be read as implying that any particular element, step, or function is an essential element that must be included in the claim scope. The scope of patented subject matter is defined only by the claims. Moreover, none of the claims is intended to invoke 25 U.S.C. § 104(f) unless the exact words "means for" are followed by a participle.

The foregoing description, for purposes of explanation, use specific nomenclature to provide a thorough understanding of the described embodiments. However, it should be apparent to one skilled in the art that the specific details are not required to practice the described embodiments. Thus, the foregoing descriptions of specific embodiments are presented for purposes of illustration and description. They are not intended to be exhaustive or to limit the described embodiments to the precise forms disclosed. It should be apparent to one of ordinary skill in the art that many modifications and variations are possible in view of the above teachings.

The above discussion is meant to be illustrative of the principles and various embodiments of the present invention. Once the above disclosure is fully appreciated, numerous variations and modifications will become apparent to those skilled in the art. It is intended that the following claims be interpreted to embrace all such variations and modifications.

What is claimed is:

1. A computer-implemented system, comprising:

a treatment device configured to be manipulated by a user while a patient performs a treatment plan, wherein, based on one or more characteristics of the patient and one or more desired results, an artificial intelligence engine generates the treatment plan and a guide map, wherein the guide map comprises a plurality of indicators and a pressure gradient map positioned over one or more sections of an augmented image of the treatment device, the treatment device comprises a plurality of sections and at least one sensor configured to detect a change in at least one parameter associated with performance of the treatment plan by the patient, and the manipulation of the treatment device by the user includes manipulating the plurality of sections of the treatment device to inflate or deflate at least one of the plurality of sections while the patient performs one or more exercises of the treatment plan;

a patient interface comprising an output device configured to present telemedicine information associated with a telemedicine session while the user performs the treatment plan; and one or more processing devices configured to:

receive the treatment plan for the patient;

during the telemedicine session, use the treatment plan to inflate the at least one of the plurality of sections; and responsive to at least one trigger condition occurring, control at least one operation of the at least one of the plurality of sections of the treatment device in one of a standby mode, inflate mode, or deflate mode, wherein the one or more processing devices are configured to determine the trigger condition occurring in response to a change in the at least one parameter as detected by the at least one sensor.

2. The system of claim 1, wherein the at least one parameter comprises a heartrate.

3. The system of claim 2, wherein the one or more processing devices are configured to receive data from the at least one sensor in real-time or near real-time.

4. The system of claim 3, wherein, to determine the at least one trigger condition, the one or more processing devices are configured to use at least one of the data, the at least one parameter, and a patient input.

5. The system of claim 1, wherein the controlling of the at least one operation of the at least one of the plurality of sections comprises causing the at least one of the plurality of sections to modify at least one of a volume, a pressure and a time period.

6. The system of claim 1, wherein the at least one parameter is at least one of a force parameter, a resistance parameter, a range of motion parameter, a temperature parameter, a pain level parameter, an exercise session parameter, a vital sign parameter, and a time parameter.

7. The system of claim 1, wherein the one or more processing devices are configured to receive the treatment plan from a clinical portal.

8. The system of claim 1, wherein the one or more processing devices are further configured to:

transmit a notification to a clinical portal in real-time or near real-time;

receive at least one adjusted parameter in real-time or near real-time; and using the at least one adjusted parameter, control the at least one operation of the treatment device in real-time or near real-time.

9. The system of claim 1, wherein the one or more processing devices are further configured to:

transmit a notification to a clinical portal;

receive at least one adjusted parameter; and using the at least one adjusted parameter, control the at least one operation of the treatment device at a time subsequent to receiving the at least one adjusted parameter.

10. The system of claim 1, wherein the treatment device further comprises at least one of a physical therapy device, a brace, a cap, a mat, and a wrap.

11. The system of claim 1, wherein the at least one parameter comprises a force parameter as detected by the at least one sensor, and wherein controlling the at least one operation of the at least one of the plurality of sections of the treatment device in one of a standby mode, inflate mode, or deflate mode comprises, responsive to the force parameter exceeding a target level, controlling the at least one operation of the at least one of the plurality of sections of the treatment device in deflate mode to reduce the force parameter.

12. The system of claim 11, wherein the artificial intelligence engine modifies, based on the force parameter exceeding a target level, the treatment plan.

13. A method for enabling a remote adjustment of a treatment device configured to be manipulated by a user while a patient performs a treatment plan, wherein an artificial intelligence engine generates, based on one or more characteristics of the patient and one or more desired results, the treatment plan and a guide map, wherein the guide map comprises a plurality of indicators and a pressure gradient map positioned over one or more sections of an augmented image of the treatment device, the treatment device comprising a plurality of sections and at least one sensor configured to detect a change in at least one parameter associated with performance of the treatment plan by the patient, and the manipulation of the treatment device by the user includes manipulating the plurality of sections of the treatment device to inflate or deflate at least one of the plurality of sections while the patient performs one or more exercises of the treatment plan, the method comprising, at a computing device configured to conduct a telemedicine session via a patient interface associated with the treatment device:

receiving the treatment plan for the user patient;

using the treatment plan to inflate the at least one of the plurality of sections; and responsive to at least one trigger condition occurring regarding a change in the at least one parameter, controlling at least one operation of the at least one of the plurality of sections of the treatment device in one of a standby mode, inflate mode, or deflate mode.

14. The method of claim 13, wherein data is received from the sensor in real-time or near real-time.

15. The method of claim 14, further comprising:

to determine the at least one trigger condition, using at least one of the data, the at least one parameter, and a patient input.

16. The method of claim 13, wherein the at least one parameter is at least one of a force parameter, a resistance parameter, a range of motion parameter, a temperature parameter, a pain level parameter, an exercise session parameter, a vital sign parameter, and a time parameter.

17. The method of claim 13, wherein the treatment plan is received from a clinical portal.

18. The method of claim 13, further comprising:

transmitting a notification to a clinical portal in real-time or near real-time;

receiving at least one adjusted parameter in real-time or near real-time; and using the adjusted parameter to control the at least one operation of the device in real-time or near real-time.

19. The method of claim 13, further comprising:

transmitting a notification to a clinical portal;

receiving at least one adjusted parameter; and using the at least one adjusted parameter to control the at least one operation of the treatment device at a time subsequent to receiving the at least one adjusted parameter.

20. The method of claim 13, wherein the treatment device further comprises at least one of a physical therapy device, a brace, a cap, a mat, and a wrap.

21. A non-transitory computer-readable medium storing instructions that, when executed, cause a processor to enable remote adjustment of a treatment device configured to be manipulated by a user while a patient performs a treatment plan, wherein an artificial intelligence engine generates, based on one or more characteristics of the patient and one or more desired results, the treatment plan and a guide map, wherein the guide map comprises a plurality of indicators and a pressure gradient map positioned over one or more sections of an augmented image of the treatment device, the treatment device comprising a plurality of sections and at least one sensor configured to detect a change in at least one parameter associated with performance of the treatment plan by the patient, and the manipulation of the treatment device by the user includes manipulating the plurality of sections of the treatment device to inflate or deflate at least one of the plurality of sections while the patient performs one or more exercises of the treatment plan, the instructions include:

receiving, at a computing device configured to conduct a telemedicine session via a patient interface associated with the treatment device, a treatment plan for the patient;

at the computing device, using the treatment plan to inflate the at least one of the plurality of sections; and at the computing device, responsive to at least one trigger condition occurring, controlling at least one operation of the at least one of the plurality of sections of the treatment device in one of a standby mode, inflate mode, or deflate mode.

22. The non-transitory computer-readable medium of claim 21, wherein the treatment plan is received from a clinical portal.

23. The non-transitory computer-readable medium of claim 21, wherein the instructions further cause the processor to:

transmit a notification to a clinical portal in real-time or near real-time;

receive at least one adjusted parameter in real-time or near real-time; and using the at least one adjusted parameter, control the at least one operation of the treatment device in real-time or near real-time.

24. The non-transitory computer-readable medium of claim 21, wherein the instructions further cause the processor to:

transmit a notification to a clinical portal;

receive at least one adjusted parameter; and using the at least one adjusted parameter, control the at least one operation of the treatment device at a time subsequent to receiving the at least one adjusted parameter.

* * * * *